(12) United States Patent
Bernate et al.

(10) Patent No.: US 11,597,921 B2
(45) Date of Patent: *Mar. 7, 2023

(54) AUTOMATED CELL PROCESSING METHODS, MODULES, INSTRUMENTS, AND SYSTEMS

(71) Applicant: Inscripta, Inc., Boulder, CO (US)

(72) Inventors: Jorge Bernate, Boulder, CO (US); Kevin Ness, Boulder, CO (US); Phillip Belgrader, Pleasanton, CA (US); Don Masquelier, Boulder, CO (US); Ryan Gill, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,233

(22) Filed: Mar. 11, 2022

(65) Prior Publication Data

US 2022/0195512 A1    Jun. 23, 2022

Related U.S. Application Data

(63) Continuation of application No. 17/538,166, filed on Nov. 30, 2021, which is a continuation of application
(Continued)

(51) Int. Cl.
*C12M 3/00* (2006.01)
*C12M 1/00* (2006.01)
(Continued)

(52) U.S. Cl.
CPC ......... *C12N 15/1082* (2013.01); *C12M 23/44* (2013.01); *C12M 33/14* (2013.01); *C12M 35/00* (2013.01); *C12M 37/04* (2013.01); *C12M 41/36* (2013.01); *C12M 41/48* (2013.01); *C12M 43/00* (2013.01); *C12N 9/22* (2013.01); *C12N 15/11* (2013.01); *C12Q 1/6865* (2013.01);
(Continued)

(58) Field of Classification Search
CPC ....... C12M 35/00; C12M 35/02; C12M 35/04
See application file for complete search history.

(56) References Cited

U.S. PATENT DOCUMENTS 6,391,582 B2    5/2002    Ying et al.
6,837,995 B1    1/2005    Vassarotti et al.
(Continued)

FOREIGN PATENT DOCUMENTS

EP    2395087    12/2011
EP    3199632    8/2017
(Continued)

OTHER PUBLICATIONS

International Search Report and Written Opinion for International Application No. PCT/US20/19379, dated Jul. 22, 2020, p. 1-10.
(Continued)

*Primary Examiner* — Nathan A Bowers
(74) *Attorney, Agent, or Firm* — Bookoff McAndrews, PLLC

(57) ABSTRACT

In an illustrative embodiment, automated multi-module cell editing instruments are provided to automate multiple edits into nucleic acid sequences inside one or more cells.

30 Claims, 26 Drawing Sheets

Related U.S. Application Data

No. 17/336,244, filed on Jun. 1, 2021, now Pat. No. 11,203,751, which is a continuation of application No. 17/200,443, filed on Mar. 12, 2021, which is a continuation of application No. 17/131,582, filed on Dec. 22, 2020, now Pat. No. 10,954,512, which is a continuation of application No. 16/988,694, filed on Aug. 9, 2020, now Pat. No. 10,894,958, which is a continuation of application No. 16/837,985, filed on Apr. 1, 2020, now Pat. No. 10,738,301, which is a continuation of application No. 16/822,249, filed on Mar. 18, 2020, now Pat. No. 10,689,645, which is a continuation of application No. 16/750,369, filed on Jan. 23, 2020, now Pat. No. 10,647,982, which is a continuation of application No. 16/680,643, filed on Nov. 12, 2019, now Pat. No. 10,584,334, which is a continuation of application No. 16/666,964, filed on Oct. 29, 2019, now Pat. No. 10,584,333, which is a continuation of application No. 16/571,091, filed on Sep. 14, 2019, now Pat. No. 10,519,437, which is a continuation of application No. 16/423,289, filed on May 28, 2019, now Pat. No. 10,465,185, which is a continuation of application No. 16/269,655, filed on Feb. 7, 2019, now Pat. No. 10,329,559, which is a continuation of application No. 16/024,816, filed on Jun. 30, 2018, now Pat. No. 10,253,316.

(60) Provisional application No. 62/689,068, filed on Jun. 23, 2018, provisional application No. 62/671,385, filed on May 14, 2018, provisional application No. 62/657,651, filed on Apr. 13, 2018, provisional application No. 62/657,654, filed on Apr. 13, 2018, provisional application No. 62/649,731, filed on Mar. 29, 2018, provisional application No. 62/648,130, filed on Mar. 26, 2018, provisional application No. 62/620,370, filed on Jan. 22, 2018, provisional application No. 62/567,697, filed on Oct. 3, 2017, provisional application No. 62/566,688, filed on Oct. 2, 2017, provisional application No. 62/566,375, filed on Sep. 30, 2017, provisional application No. 62/566,374, filed on Sep. 30, 2017, provisional application No. 62/551,069, filed on Aug. 28, 2017, provisional application No. 62/527,339, filed on Jun. 30, 2017.

(51) Int. Cl.
*C12N 15/10* (2006.01)
*C40B 40/02* (2006.01)
*C12M 1/26* (2006.01)
*C12M 1/42* (2006.01)
*C12M 1/34* (2006.01)
*C12Q 1/6865* (2018.01)
*C12M 1/12* (2006.01)
*C12M 1/36* (2006.01)
*C12N 9/22* (2006.01)
*C12N 15/11* (2006.01)

(52) U.S. Cl.
CPC .......... *C40B 40/02* (2013.01); *C12N 2310/20* (2017.05); *C12N 2800/80* (2013.01)

(56) References Cited

U.S. PATENT DOCUMENTS

| | | |
|---|---|---|
| 7,166,443 B2 | 1/2007 | Walker et al. |
| 8,332,160 B1 | 12/2012 | Platt et al. |
| 8,697,359 B1 | 4/2014 | Zhang et al. |
| 8,926,977 B2 | 1/2015 | Milier et al. |
| 9,260,505 B2 | 2/2016 | Weir et al. |
| 9,361,427 B2 | 6/2016 | Hillson |
| 9,499,855 B2 | 11/2016 | Hyde et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 9,988,624 B2 | 6/2018 | Serber et al. |
| 10,011,849 B1 | 7/2018 | Gill et al. |
| 10,017,760 B2 | 7/2018 | Gill et al. |
| 10,227,576 B1 | 3/2019 | Cameron et al. |
| 10,266,851 B2 | 4/2019 | Chen |
| 10,704,033 B1 | 7/2020 | Kim et al. |
| 10,724,021 B1 | 7/2020 | Kim et al. |
| 10,745,678 B1 | 8/2020 | Kim et al. |
| 10,767,169 B1 | 9/2020 | Kim et al. |
| 10,837,021 B1 | 11/2020 | Tian et al. |
| 10,927,385 B2 | 2/2021 | Kannan et al. |
| 2002/0139741 A1 | 10/2002 | Kopf |
| 2004/0110253 A1 | 6/2004 | Kappler et al. |
| 2006/0014137 A1 | 1/2006 | Ghosh et al. |
| 2007/0020761 A1 | 1/2007 | Yu et al. |
| 2009/0042281 A1* | 2/2009 | Chang ................. G01N 35/0099 435/287.1 |
| 2010/0076057 A1 | 3/2010 | Sontheimer et al. |
| 2011/0294217 A1 | 12/2011 | McConnell-Smith et al. |
| 2013/0005025 A1 | 1/2013 | Church et al. |
| 2013/0236970 A1 | 9/2013 | Anneren et al. |
| 2014/0068797 A1 | 3/2014 | Doudna et al. |
| 2014/0199767 A1 | 7/2014 | Barrangou et al. |
| 2014/0242033 A1 | 8/2014 | Gruber et al. |
| 2014/0273226 A1 | 9/2014 | Wu et al. |
| 2015/0024464 A1 | 1/2015 | Lippow et al. |
| 2015/0071898 A1 | 3/2015 | Liu et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0285786 A1* | 10/2015 | Hahn ................. B01L 3/502753 435/320.1 |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2016/0367991 A1 | 12/2016 | Petersen et al. |
| 2017/0002339 A1 | 1/2017 | Barrngou et al. |
| 2017/0022499 A1 | 1/2017 | Lu et al. |
| 2017/0029805 A1* | 2/2017 | Li ........................... A61P 31/00 |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0051243 A1* | 2/2018 | Hogan ..................... C12M 47/12 |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0147576 A1* | 5/2018 | Lavieu ..................... C12M 23/16 |
| 2018/0169148 A1* | 6/2018 | Adair ........................ C12Q 1/68 |
| 2018/0187149 A1 | 7/2018 | Ma et al. |
| 2018/0200342 A1 | 7/2018 | Bikard et al. |
| 2018/0203017 A1 | 7/2018 | Ting et al. |
| 2018/0230460 A1 | 8/2018 | Gill et al. |
| 2018/0230461 A1 | 8/2018 | Gill et al. |

(56) References Cited

U.S. PATENT DOCUMENTS

| | | |
|---|---|---|
| 2018/0284125 A1 | 10/2018 | Gordon et al. |
| 2018/0327761 A1 | 11/2018 | Duchateau et al. |
| 2018/0371498 A1 | 12/2018 | Gill et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0109398 A1 | 4/2020 | Rubens et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |

FOREIGN PATENT DOCUMENTS

| | | |
|---|---|---|
| JP | 2015506673 A | 3/2015 |
| RU | 95663 U1 | 7/2010 |
| WO | WO2002/010183 | 2/2002 |
| WO | WO 2003/087341 | 10/2003 |
| WO | WO 2010/079430 | 7/2010 |
| WO | WO 2011/072246 | 6/2011 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO2014/143381 | 9/2014 |
| WO | WO 2014/144495 | 9/2014 |
| WO | WO 2016/110453 | 7/2016 |
| WO | WO 2017/053902 | 3/2017 |
| WO | WO2017/075265 | 5/2017 |
| WO | WO 2017/078631 | 5/2017 |
| WO | WO 2017/083722 | 5/2017 |
| WO | 2017100377 A1 | 6/2017 |
| WO | WO 2017/106414 | 6/2017 |
| WO | WO2017/106414 | 6/2017 |
| WO | WO 2017/161371 | 9/2017 |
| WO | WO 2017/174329 | 10/2017 |
| WO | WO 2017/186718 | 11/2017 |
| WO | WO2017/212400 | 12/2017 |
| WO | WO 2017/216392 | 12/2017 |
| WO | WO 2017/223330 | 12/2017 |
| WO | WO 2018/031950 | 2/2018 |
| WO | WO 2018/071672 | 4/2018 |
| WO | WO2018/073391 | 4/2018 |
| WO | WO 2018/083339 | 5/2018 |
| WO | WO2018/152325 | 8/2018 |
| WO | WO2018/172556 | 9/2018 |
| WO | WO 2018/191715 | 10/2018 |
| WO | WO2019/006436 | 1/2019 |
| WO | WO2019/055878 | 3/2019 |
| WO | WO2019/200004 | 10/2019 |
| WO | WO2019/209926 | 10/2019 |
| WO | WO2020/005383 | 1/2020 |
| WO | WO2020/021045 | 1/2020 |
| WO | WO2020/074906 | 4/2020 |
| WO | WO2020/191102 | 9/2020 |
| WO | WO2020/191153 | 9/2020 |
| WO | WO2020/217057 | 10/2020 |
| WO | WO2021/207541 | 10/2021 |

OTHER PUBLICATIONS

International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).
Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864. ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.

(56) References Cited

OTHER PUBLICATIONS

Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechnology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS ONE, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/A0A_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Anzalone, et al., "Programmable large DNA deletion, replacement, integration, and inversion with twin prime editing and site-specific recombinases", bioRxiv, Nov. 2, 2021, doi:10.1101/2021.11.01.466790, p. 1-51.
Horwitz, et al., "Efficient Multiplexed Integration of Synergistic Alleles and Metabolic Pathways in Yeasts via CRISPR-Cas", Cell Systems 1, Jul. 29, 2015, doi:10.1016/j.cels.2015.02.001, p. 88-96.
Jillette, et al., "Split Selectable Markers", Nature Communications, Oct. 31, 2019, doi:10.1038/s41467-019-12891-2, p. 1-8.
Pavankumar, "Inteins: Localized Distribution, Gene Regulation, and Protein Engineering for Biological Applications", Microorganisms, Feb. 28, 2018, doi:10.3390/microorganisms6010019, p. 1-15.
Choi, et al., "Precise genomic deletions using paired prime editing", bioRxiv, Jan. 2, 2021, doi:10.1101/2020.12.30.424891, p. 1-32.
Lin, et al., "High-efficiency prime editing with optimized, paired pegRNAs in plants", Nature Biotechnology, Mar. 25, 2021, doi:10.1038/s41587-021-00868-w, p. 1-12.
Bolukbasi, et al., "Orthogonal Cas9-Cas9 chimeras provide a versatile platform for genome editing", Nature Communications, Nov. 19, 2018, doi:10.1038/s41467-018-07310-x, p. 1-12.
Kweon, et al., "Fusion guide RNAs for orthogonal gene manipulation with Cas9 and Cpf1", Nature Communications, Nov. 23, 2017, doi:10.1038/s41467-017-01650-w, p. 1-6.
International Search Report and Written Opinion for International Application No. PCT/US21/48578, dated Feb. 15, 2022, p. 1-12.
International Search Report and Written Opinion for International Application No. PCT/US21/61156, dated Mar. 3, 2022, p. 1-13.
International Search Report and Written Opinion for International Application No. PCT/US20/53873, dated Jan. 14, 2021, p. 1-16.
Bao, et al., "Genome-scale engineering of *Saccharomyces cerevisiae* with single-nucleotide precision", Nature Biotechnology, doi:10.1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).
Garst, et al., "Genome-wide mapping of mutations at single-nucleotide resolution for protein, metabolic and genome engineering", Nature Biotechnology, 35(1):48-59 (2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Verwaal, et al., "CRISPR/Cpfl enables fast and simple genome editing of *Saccharamyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Dong, "Establishment of a highly efficient virus-inducible CRISPR/Cas9 system in insect cells," Antiviral Res., 130:50-7(2016).
Epinat et al., "A novel engineered meganuclease induces homologous recombination in eukaryotic cells, e.g., yeast and mammalian cells", Nucleic Acids Research, 31(11): 2952-2962.
Farasat et al., "A Biophysical Model of CRISPR/Cas9 Activity for Rational Design of Genome Editing and Gene Regulation," PLoS Comput Biol., 29:12(1):e1004724 (2016).
Liu et al., "A chemical-inducible CRISPR-Cas9 system for rapid control of genome editing", Nature Chemical Biology, 12:980-987(2016).
Eklund, et al., "Altered target site specificity variants of the I-Ppol His-Cys bis homing endonuclease" Nucleic Acids Research, 35(17):5839-50 (2007).
Boles, et al., "Digital-to-biological converter for on-demand production of biologies", Nature Biotechnology, doi:10.1038/nbt.3859 (May 29, 2017).
Pines, et al., "Codon Compression Algorithms for Saturation Mutagenesis", ACS Synthetic Biology, 4:604-14 (2015).

(56) References Cited

OTHER PUBLICATIONS

Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Durai et al., "Zinc finger nucleases: custom-designed molecular scissors for genome engineering of plant and mammalian cells", Nucleic Acids Res., 33(18):5978-90 (2005).
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1): 81-9 (2009).
Miller et al., "A TALE nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.

\* cited by examiner

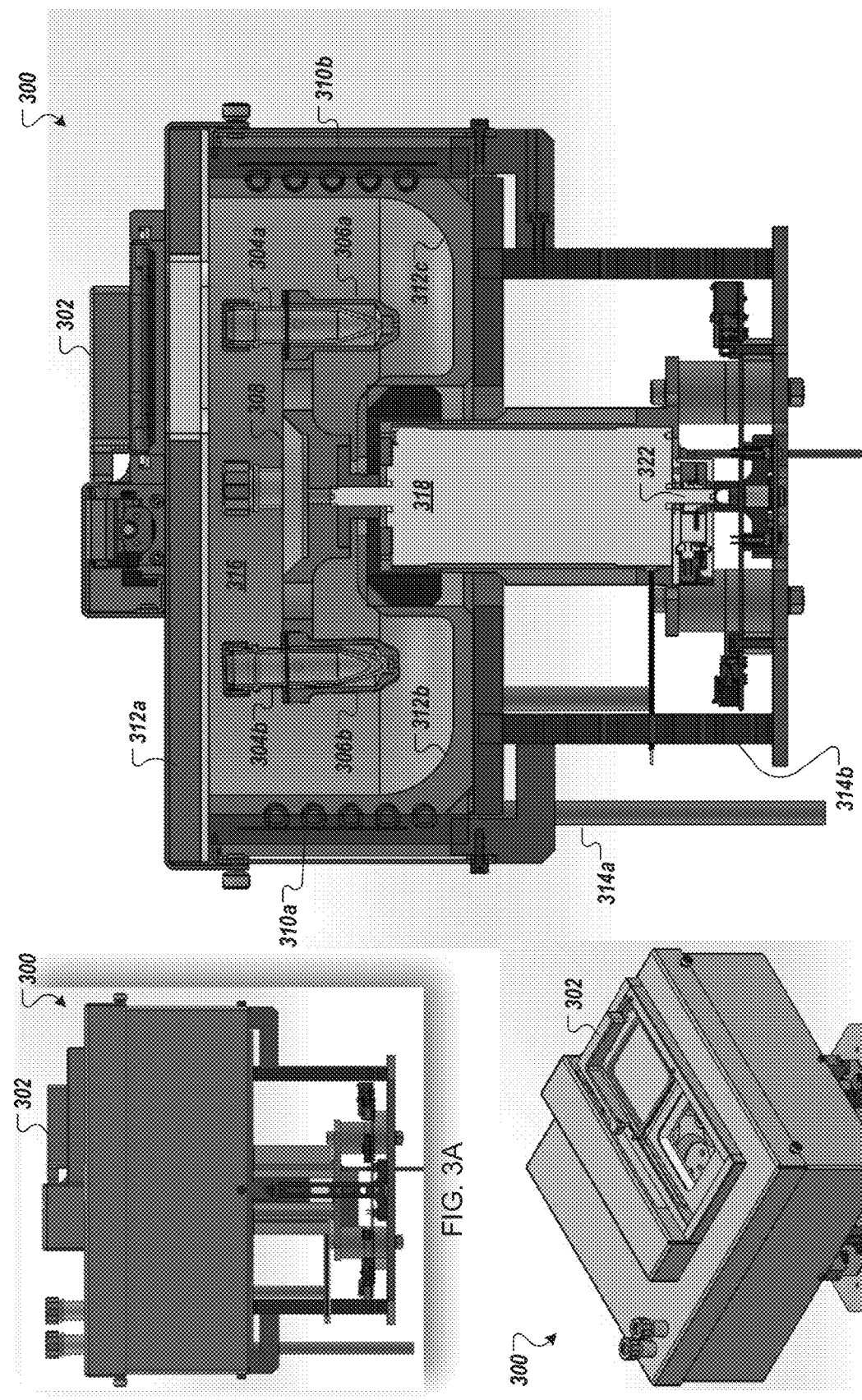

1. FILTER CARTRIDGE

AUTOMATED CELL PROCESSING METHODS, MODULES, INSTRUMENTS, AND SYSTEMS

RELATED APPLICATIONS

This application is a Continuation of U.S. Ser. No. 17/538,922, entitled "Automated Cell Processing Methods, Modules, Instruments, and Systems," filed 30 Nov. 2021, now U.S. Pat. No. 11,293,021; which is a Continuation of U.S. Ser. No. 17/336,244, entitled "Automated Cell Processing Methods, Modules, Instruments, and Systems," filed 1 Jun. 2021, now U.S. Pat. No. 11,203,751; which is a Continuation of U.S. Ser. No. 17/200,443, entitled "Automated Cell Processing Methods, Modules, Instruments, and Systems," filed 12 Mar. 2021; which is a Continuation of U.S. Ser. No. 17/131,582, entitled "Automated Cell Processing Methods, Modules, Instruments, and Systems," filed Dec. 22, 2020, now U.S. Pat. No. 10,954,512; which is a Continuation of U.S. Ser. No. 16/988,694, entitled "Automated Cell Processing Methods, Modules, Instruments, and Systems," filed Aug. 9, 2020, now U.S. Pat. No. 10,894,958; which is a Continuation of U.S. Ser. No. 16/837,985, entitled "Automated Cell Processing Methods, Modules, Instruments, and Systems," filed Apr. 1, 2020, now U.S. Pat. No. 10,738,301; which is a Continuation Patent Application of U.S. Ser. No. 16/822,249, entitled "Automated Cell Processing Methods, Modules, Instruments, and Systems," filed Mar. 18, 2020, now U.S. Pat. No. 10,689,645; which is a Continuation Patent Application of U.S. Ser. No. 16/750,369, entitled "Automated Cell Processing Methods, Modules, Instruments, and Systems," filed Jan. 23, 2020, now U.S. Pat. No. 10,647,982; which is a Continuation Patent Application of U.S. Ser. No. 16/680,643, entitled "Automated Cell Processing Methods, Modules, Instruments, and Systems," filed Nov. 12, 2019, now U.S. Pat. No. 10,584,334; which is a Continuation Patent Application of U.S. Ser. No. 16/666,964, entitled "Automated Cell Processing Methods, Modules, Instruments, and Systems," filed Oct. 29, 2019, now U.S. Pat. No. 10,584,333; which is a Continuation Patent Application of U.S. Ser. No. 16/571,091, entitled "Automated Cell Processing Methods, Modules, Instruments, and Systems," filed Sep. 14, 2019, now U.S. Pat. No. 10,519,437; which is a Continuation Patent Application of U.S. Ser. No. 16/423,289, entitled "Automated Cell Processing Methods, Modules, Instruments, and Systems," filed May 28, 2019, now U.S. Pat. No. 10,465,185; which is a Continuation Patent Application of U.S. Ser. No. 16/269,655, entitled "Automated Cell Processing Methods, Modules, Instruments, and Systems," filed Feb. 7, 2019, now U.S. Pat. No. 10,329,559; which is a continuation of U.S. Ser. No. 16/024,816, entitled "Automated Cell Processing Methods, Modules, Instruments, and Systems," filed Jun. 30, 2018 now U.S. Pat. No. 10,253,316; all of which claim priority to U.S. Patent Application Ser. No. 62/527,339, entitled "Automated Editing of Nucleic Acids Within a Cell," filed Jun. 30, 2017; U.S. Patent Application Ser. No. 62/551,069, entitled "Electroporation Cuvettes for Automation," filed Aug. 28, 2017; U.S. Patent Application Ser. No. 62/566,374, entitled "Electroporation Device," filed Sep. 30, 2017; U.S. Patent Application Ser. No. 62/566,375, entitled "Electroporation Device," filed Sep. 30, 2017; U.S. Patent Application Ser. No. 62/566,688, entitled "Introduction of Exogenous Materials into Cells," filed Oct. 2, 2017; U.S. Patent Application Ser. No. 62/567,697, entitled "Automated Nucleic Acid Assembly and Introduction of Nucleic Acids into Cells," filed Oct. 3, 2017; U.S. Patent Application Ser. No. 62/620,370, entitled "Automated Filtration and Manipulation of Viable Cells," filed Jan. 22, 2018; U.S. Patent Application Ser. No. 62/649,731, entitled "Automated Control of Cell Growth Rates for Induction and Transformation," filed Mar. 29, 2018; U.S. Patent Application Ser. No. 62/671,385, entitled "Automated Control of Cell Growth Rates for Induction and Transformation," filed May 14, 2018; U.S. Patent Application Ser. No. 62/648,130, entitled "Genomic Editing in Automated Systems," filed Mar. 26, 2018; U.S. Patent Application Ser. No. 62/657,651, entitled "Combination Reagent Cartridge and Electroporation Device," filed Apr. 13, 2018; U.S. Patent Application Ser. No. 62/657,654, entitled "Automated Cell Processing Systems Comprising Cartridges," filed Apr. 13, 2018; and U.S. Patent Application Ser. No. 62/689,068, entitled "Nucleic Acid Purification Protocol for Use in Automated Cell Processing Systems," filed Jun. 23, 2018. All above identified applications are hereby incorporated by reference in their entireties for all purposes.

BACKGROUND

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genome editing with engineered nucleases is a method in which changes to nucleic acids are made in the genome of a living organism. Certain nucleases create site-specific double-strand breaks at target regions in the genome, which can be repaired by nonhomologous end-joining or homologous recombination, resulting in targeted edits. These methods, however, have not been compatible with automation due to low efficiencies and challenges with cell transformation, growth measurement, and cell selection. Moreover, traditional benchtop devices do not necessarily scale and integrate well into an automated, modular system. Methods and systems to create edited cell populations thus remain cumbersome, and the challenges of introducing multiple rounds of edits using recursive techniques has limited the nature and complexity of cell populations that can be created.

There is thus a need for automated instruments, systems and methods for introducing assembled nucleic acids and other biological molecules into living cells in an automated fashion where the edited cells may be used for further experimentation outside of the automated instrument.

SUMMARY OF ILLUSTRATIVE EMBODIMENTS

In certain embodiments, automated methods are used for nuclease-directed genome editing of one or more target genomic regions in multiple cells, the methods being performed in automated multi-module cell editing instruments. These methods can be used to generate libraries of living cells of interest with desired genomic changes. The automated methods carried out using the automated multi-module cell editing instruments described herein can be used with a variety of nuclease-directed genome editing techniques, and can be used with or without use of one or more selectable markers.

The present disclosure thus provides, in selected embodiments, modules, instruments, and systems for automated multi-module cell editing, including nuclease-directed genome editing. Other specific embodiments of the automated multi-module cell editing instruments of the disclosure are designed for recursive genome editing, e.g., sequentially introducing multiple edits into genomes inside one or more cells of a cell population through two or more editing operations within the instruments.

Thus, provided herein are embodiments of an automated multi-module cell editing instrument comprising: a housing configured to contain all or some of the modules; a receptacle configured to receive cells; one or more receptacles configured to receive nucleic acids; a transformation module configured to introduce the nucleic acids into the cells; a recovery module configured to allow the cells to recover after cell transformation in the transformation module; an editing module configured to allow the nucleic acids transformed into the cells to edit nucleic acids in the cells; and a processor configured to operate the automated multi-module cell editing instrument based on user input and/or selection of an appropriate controller script.

In some aspects, the nucleic acids in the one or more receptacles comprise a backbone and an editing cassette, and the automated multi-module cell editing instrument further comprises a nucleic acid assembly module. In some aspects, the nucleic acid assembly module comprises a magnet, and in some aspects, the nucleic acid assembly module is configured to perform assembly using a single, isothermal reaction. In other aspects, the nucleic acid assembly module is configured to perform an amplification and/or ligation method.

In some aspects of the automated multi-module cell editing instrument, the editing module and the recovery module are combined.

In some aspects, the automated multi-module cell editing instrument may further comprise a growth module configured to grow the cells, and in some implementations, the growth module measures optical density of the growing cells, either continuously or at intervals. In some implementations, the processor is configured to adjust growth conditions in the growth module such that the cells reach a target optical density at a time requested by a user. Further, in some embodiments, the user may be updated regarding growth process.

In some aspects, the automated multi-module cell editing instrument comprises a reagent cartridge where the receptacle configured to receive cells and the one or more receptacles configured to receive nucleic acids are contained within a reagent cartridge. Further, the reagent cartridge may also contain some or all reagents required for cell editing. In some implementations, the reagents contained within the reagent cartridge are locatable by a script read by the processor, and in some implementations, the reagent cartridge includes reagents and is provided in a kit.

In some aspects, the transformation module of the automated multi-module cell editing instrument comprises an electroporation device; and in some implementations, the electroporation device is a flow-through electroporation device.

Some aspects of the automated multi-module cell editing instrument further comprise a filtration module configured to exchange liquids and/or concentrate the cells. In specific aspects, the filtration system can also be used to render the cells electrocompetent.

In other embodiments, an automated multi-module cell editing instrument is provided, where the automated multi-module cell editing instrument comprises a housing configured to house some or all of the modules; a receptacle configured to receive cells; at least one receptacle configured to receive a nucleic acid backbone and an editing cassette; a nucleic acid assembly module configured to a) assemble the backbone and editing cassette, and b) de-salt assembled nucleic acids after assembly; a growth module configured to grow the cells and measure optical density (OD) of the cells; a filtration module configured to concentrate the cells and render the cells electrocompetent; a transformation module comprising a flow-through electroporator to introduce the assembled nucleic acids into the cells; a combination recovery and editing module configured to allow the cells to recover after electroporation in the transformation module and to allow the assembled nucleic acids to edit nucleic acids in the cells; and a processor configured to operate the automated multi-module cell editing instrument based on user input and/or selection of an appropriate controller script.

In some implementations, the automated multi-module cell editing instrument provides a reagent cartridge comprising a plurality of reagent reservoirs, a flow-through electroporation device, and a script readable by a processor for dispensing reagents located in the plurality of reagent reservoirs and controlling the flow-through electroporation device.

In some aspects, the growth module includes a temperature-controlled rotating growth vial, a motor assembly to spin the vial, a spectrophotometer for measuring, e.g., OD in the vial, and a processor to accept input from a user and control the growth rate of the cells. The growth module may automatically measure the OD of the growing cells in the rotating growth vial continuously or at set intervals, and control the growth of the cells to a target OD and a target time as specified by the user. That is, the methods and devices described herein provide a feedback loop that monitors cell growth in real time, and adjusts the temperature of the rotating growth vial in real time to reach the target OD at a target time specified by a user.

In some aspects of the automated multi-module cell editing instrument, the transformation module comprises a flow-through electroporation device, where the flow-through electroporation device comprises an inlet and inlet channel for introduction of the cell sample and assembled nucleic acids into the flow-through electroporation device; an outlet and outlet channel for exit of the electroporated cell sample from the flow-through electroporation device; a flow channel intersecting and positioned between the inlet channel and outlet channel; and two or more electrodes, where the two or more electrodes are positioned in the flow channel between the intersection of the flow channel with the first inlet channel and the intersection of the flow channel with the outlet channel, in fluid communication with the cell sample in the flow channel, and configured to apply an electric pulse or electric pulses to the cell sample. In specific aspects, the flow through electroporation device can comprise two or more flow channels in parallel.

Systems for using the automated multi-module cell editing instrument to implement genomic editing operations within cells are also provided. These systems may optionally include one or more interfaces between the instrument and other devices or receptacles for cell preparation, nucleic acid preparation, selection of edited cell populations, functional analysis of edited cell populations, storage of edited cell populations, and the like.

In addition, methods for using the automated multi-module cell editing instrument are provided. In some methods, electrocompetent cells are provided directly to the instrument, preferably at a desired optical density, and transferred to a transformation module. In some methods, cells are transferred to a growth module, where they are grown to a desired optical density. The cells are then transferred from the growth vial to a filtration module where they are concentrated and optionally rendered electrocompetent. The cells are then transferred to a transformation module.

In some aspects, assembled nucleic acid cassettes are provided directly to the instrument, and transferred to a transformation module. In some aspects, nucleic acids, such as a vector backbone and one or more oligonucleotide editing cassettes are transferred to a nucleic acid assembly module either simultaneously or sequentially with the cell introduction or preparation. In this aspect, nucleic acids are assembled, de-salted (e.g., through a liquid exchange or osmosis), and transferred to the transformation module to be electroporated into the electrocompetent cells. Electroporation or transfection takes place in the transformation module, then the cells are transferred to a recovery/editing module that optionally includes selection of the cells containing the one or more genomic edits. After recovery/editing/selection, the cells may be retrieved and used directly for research or stored for further research, or another round (or multiple rounds) of genomic editing can be performed by repeating the editing steps within the instrument.

Also provided are cell libraries created using an automated multi-module cell editing instrument for nuclease-directed genome editing, where the instrument comprises: a housing; a receptacle configured to receive cells and one or more rationally designed nucleic acids comprising sequences to facilitate nuclease-directed genome editing events in the cells; a transformation module for introduction of the nucleic acid(s) into the cells; an editing module for allowing the nuclease-directed genome editing events to occur in the cells, and a processor configured to operate the automated multi-module cell editing instrument based on user input, wherein the nuclease-directed genome editing events created by the automated instrument result in a cell library comprising individual cells with rationally designed edits.

In some aspects, the cell library comprises a saturation mutagenesis cell library. In some aspects, the cell library comprises a promoter swap cell library. In other aspects, the cell library comprises a terminator swap cell library. In yet other aspects, the cell library comprises a single nucleotide polymorphism (SNP) swap cell library. In yet other aspects, the cell library comprises a promoter swap cell library.

In some implementations, the library comprises at least 100,000 edited cells, and in yet other implementations, the library comprises at least 1,000,000 edited cells.

In some implementations, the nuclease-directed genome editing is RGN-directed genome editing. In a preferred aspect, the instrument is configured for the use of an inducible nuclease. The nuclease may be, e.g., chemically induced, virally induced, light induced, temperature induced, or heat induced.

In some implementations, the instrument provides multiplexed genome editing of multiple cells in a single cycle. In some aspects, the instrument has the ability to edit the genome of at least 5 cells in a single cycle. In other aspects, the instrument has the ability to edit the genome of at least 100 cells in a single cycle. In yet other aspects, the instrument has the ability to edit the genome of at least 1000 cells in a single cycle. In still other aspects, the instrument has the ability to edit the genome of at least 10,000 cells in a single cycle. In specific aspects, the automated multi-module cell editing instruments have the ability to edit the genome of at least $10^4$, $10^5$, $10^6$ $10^7$, $10^8$, $10^9$, $10^{10}$, $10^{11}$, $10^{12}$, $10^{13}$, $10^{14}$ or more cells in a single cycle.

The number of genomic sites in a cell population that can be targeted for editing in a single cycle can be between 2-10,000,000.

In some embodiments that involve recursive editing, the automated multi-module cell editing instrument provides introducing two or more genome edits into cells, with a single genome edit added to the genomes of the cell population for each cycle. Accordingly, some aspects the automated multi-module cell editing instruments of the present disclosure are useful for sequentially providing two or more edits per cell in a cell population per cycle, three or more edits per cell in a cell population, five or more edits per cell in a population, or 10 or more edits per cell in a single cycle for a cell population.

In specific embodiments, the automated multi-module cell editing instrument is able to provide an editing efficiency of at least 10% of the cells introduced to the editing module per cycle, preferably an editing efficiency of at least 20% of the cells introduced to the editing module per cycle, more preferably an editing efficiency of at least 25% of the cells introduced to the editing module per cycle, still more preferably an editing efficiency of at least 30% of the cells introduced to the editing module automated multi-module cell editing instrument per cycle, yet more preferably an editing efficiency of at least 40% of the cells introduced to the editing module per cycle and even more preferably 50%, 60%, 70%, 80%, 90% or more of the cells introduced to the editing module per cycle.

Other features, advantages, and aspects will be described below in more detail.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIGS. 3A-3C depict side, cut-away and perspective views of an example cell wash and/or concentration module for use in an automated multi-module cell processing instrument.

DETAILED DESCRIPTION OF ILLUSTRATIVE EMBODIMENTS

Figure 1A:
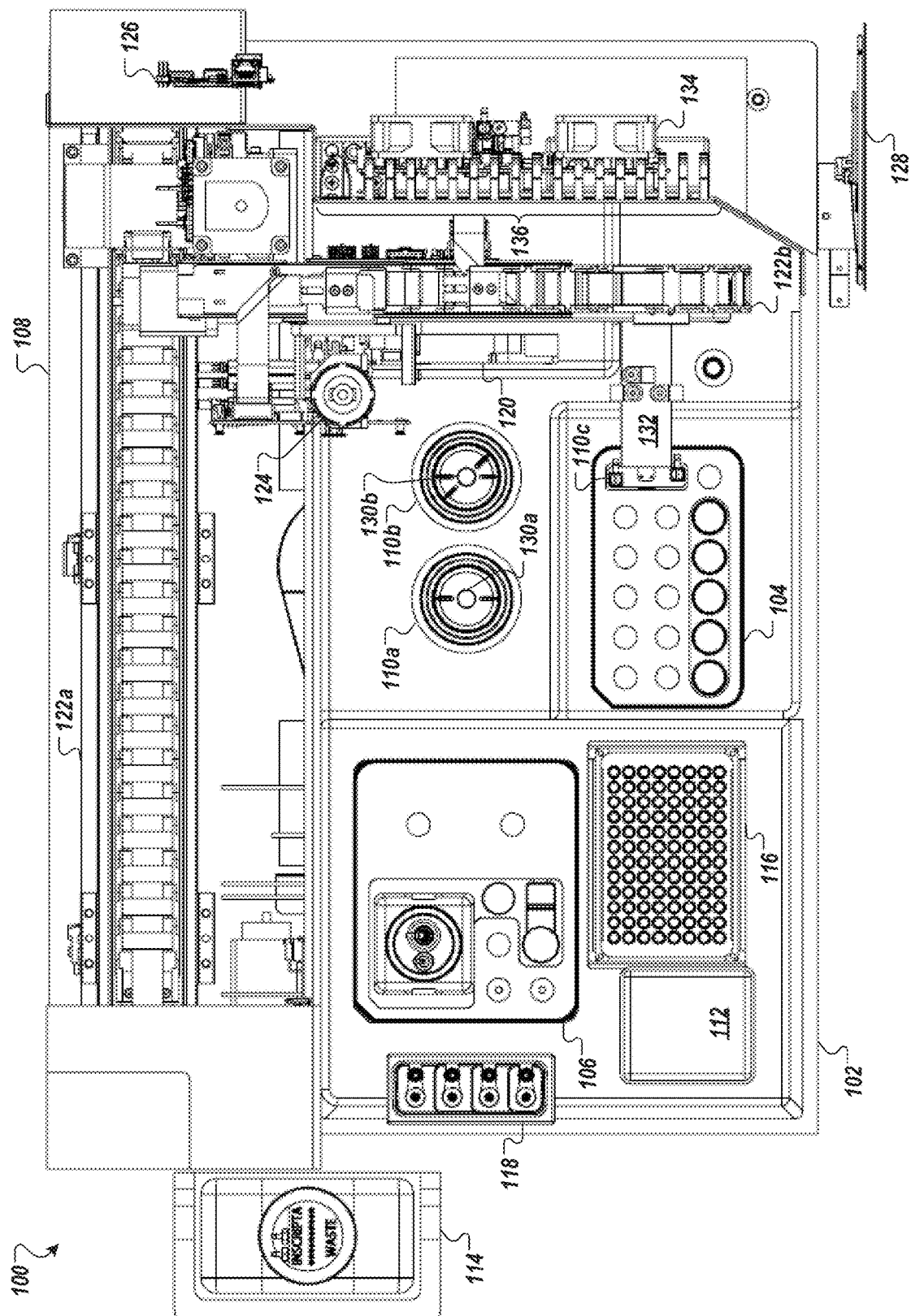
FIGS. 1A and 1B depict plan and perspective views of an example embodiment of an automated multi-module cell processing instrument for the multiplexed genome editing of multiple cells using a replaceable cartridge(s) as a part of the instrument.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

The practice of the techniques described herein may employ the techniques set forth in Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach, Dveksler, Eds. (2003), PCR Primer: A Laboratory Manual; Bowtell and Sambrook (2003), Bioinformatics: Sequence and Genome Analysis; Sambrook and Russell (2006), Condensed Protocols from Molecular Cloning: A Laboratory Manual; and Green and Sambrook, (Molecular Cloning: A Laboratory Manual. 4th, ed., Cold Spring Harbor Laboratory Press, Cold Spring Harbor, N.Y., 2014); Stryer, L. (1995) Biochemistry (4th Ed.) W. H. Freeman, New York N. Y.; Gait, "Oligonucleotide Synthesis: A Practical Approach" 1984, IRL Press, London; Nelson and Cox (2000), Lehninger, Principles of Biochemistry $3^{rd}$ Ed., W. H. Freeman Pub., New York, N.Y.; and Berg et al. (2002) Biochemistry, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an oligo" refers to one or more oligos that serve the same function, to "the methods" includes reference to equivalent steps and methods known to those skilled in the art, and so forth. That is, unless expressly specified otherwise, as used herein the words "a," "an," "the" carry the meaning of "one or more." Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Unless defined otherwise, all technical and scientific terms used herein have the same meaning as commonly understood by one of ordinary skill in the art to which this disclosure belongs.

All publications (including patents, published applications, and non-patent literature) mentioned herein are incorporated by reference for all purposes, including but not limited to the purpose of describing and disclosing devices, systems, and methods that may be used or modified in connection with the presently described methods, modules, instruments, and systems.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment.

Further, the particular features, structures or characteristics may be combined in any suitable manner in one or more embodiments. Further, it is intended that embodiments of the disclosed subject matter cover modifications and variations thereof.

Introduction and Overview

In selected embodiments, the automated multi-module cell editing instruments, systems and methods described herein can be used in multiplexed genome editing in living cells, as well as in methods for constructing libraries of edited cell populations. The automated multi-module cell editing instruments disclosed herein can be used with a variety of genome editing techniques, and in particular with nuclease-directed genome editing. The automated multi-module cell editing instruments of the disclosure provide novel methods for introducing nucleic acid sequences targeting genomic sites for editing the genome of living cells, including methods for constructing libraries comprising various classes of genomic edits to coding regions, non-coding regions, or both. The automated multi-module cell editing instruments are particularly suited to introduction of genome edits to multiple cells in a single cycle, thereby generating libraries of cells having one or more genome edits in an automated, multiplexed fashion. The automated multi-module cell editing instruments are also suited to introduce two or more edits, e.g., edits to different target genomic sites in individual cells of a cell population. Whether one or many, these genome edits are preferably rationally-designed edits; that is, nucleic acids that are designed and created to introduce specific edits to target regions within a cell's genome. The sequences used to facilitate genome-editing events include sequences that assist in guiding nuclease cleavage, the introduction of a genome edit to a region of interest, and/or both. These sequences may also include an edit to a region of the cell's genome to allow the specific rationally designed edit in the cell's genome to be tracked. Such methods of introducing edits into cells are taught, e.g., in U.S. Pat. No. 9,982,278, entitled "CRISPR enabled multiplexed genome engineering," by Gill et al., and U.S. Pat. No. 10,017,760, application Ser. No. 15/632,222, entitled "Methods for generating barcoded combinatorial libraries," to Gill et al.

Such nucleic acids and oligonucleotides (or "oligos") are intended to include, but are not limited to, a polymeric form of nucleotides that may have various lengths, including either deoxyribonucleotides or ribonucleotides, or analogs thereof. The nucleic acids and oligonucleotides for use in the illustrative embodiments can be modified at one or more positions to enhance stability introduced during chemical synthesis or subsequent enzymatic modification or polymerase copying. These modifications include, but are not limited to, the inclusion of one or more alkylated nucleic acids, locked nucleic acids (LNAs), peptide nucleic acids (PNAs), phosphonates, phosphothioates in the oligomer. Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Nucleic acid molecules may also be modified at the base moiety, sugar moiety or phosphate backbone.

Nuclease-Directed Genome Editing

In selected embodiments, the automated multi-module cell editing instruments described herein utilize a nuclease-directed genome editing system. Multiple different nuclease-based systems exist for providing edits into an organism's genome, and each can be used in either single editing systems, sequential editing systems (e.g., using different nuclease-directed systems sequentially to provide two or more genome edits in a cell) and/or recursive editing systems, (e.g. utilizing a single nuclease-directed system to introduce two or more genome edits in a cell). Exemplary nuclease-directed genome editing systems are described herein, although a person of skill in the art would recognize upon reading the present disclosure that other enzyme-directed editing systems are also useful in the automated multi-module cell editing instruments of the illustrative embodiments.

It should be noted that the automated systems as set forth herein can use the nucleases for cleavage of the genome and introduction of an edit into a target genomic region using an instrument of the disclosure.

In particular aspects of the illustrative embodiments, the nuclease editing system is an inducible system that allows control of the timing of the editing. The inducible system may include inducible expression of the nuclease, inducible expression of the editing nucleic acids, or both. The ability to modulate nuclease activity can reduce off-target cleavage and facilitate precise genome engineering. Numerous different inducible systems can be used with the automated multi-module cell editing instruments of the disclosure, as will be apparent to one skilled in the art upon reading the present disclosure.

In certain aspects, cleavage by a nuclease can be also be used with the automated multi-module cell editing instruments of the illustrative embodiments to select cells with a genomic edit at a target region. For example, cells that have been subjected to a genomic edit that removes a particular nuclease recognition site (e.g., via homologous recombination) can be selected using the automated multi-module cell editing instruments and systems of the illustrative embodiments by exposing the cells to the nuclease following such edit. The DNA in the cells without the genome edit will be cleaved and subsequently will have limited growth and/or perish, whereas the cells that received the genome edit removing the nuclease recognition site will not be affected by the subsequent exposure to the nuclease.

If the cell or population of cells includes a nucleic acid-guided nuclease encoding DNA that is induced by an inducer molecule, the nuclease will be expressed only in the presence of the inducer molecule. Alternatively, if the cell or population of cells includes a nucleic acid-guided nuclease encoding DNA that is repressed by a repressor molecule, the nuclease will be expressed only in the absence of the repressor molecule.

For example, inducible systems for editing using RNA-guided nuclease have been described, which use chemical induction to limit the temporal exposure of the cells to the RNA-guided nuclease. (US Patent Application Publication 2015/0291966 A1 to Zhang et al., entitled "Inducible DNA Binding Proteins and Genome Perturbation Tools and Applications Thereof," filed Jan. 23, 2015; see also inducible lentiviral expression vectors available at Horizon/Dharmacon, Lafayette, Colo. For additional techniques, see e.g., Campbell, Targeting protein function: the expanding toolkit for conditional disruption, Biochem J., 473(17): 2573-2589 (2016).

In other examples, a virus-inducible nuclease can be used to induce gene editing in cells. See, e.g., Dong, Establishment of a highly efficient virus-inducible CRISPR/Cas9 system in insect cells, Antiviral Res., 130:50-7 (2016). In another example, for inducible expression of nucleic acid directed nucleases, variants can be switched on and oft in mammalian cells with 4-hydroxytamoxifen (4-HT) by fusing the nuclease with the hormone-binding domain of the estrogen receptor (ERT2). (Liu, et al. Nature chemical Biology, 12:980-987 (2016) and see International Patent Application Publication WO 2017/078631 A1 to Tan, entitled "Chemical-Inducible Genome Engineering Technology," filed Nov. 7, 2016.

In addition, a number of gene regulation control systems have been developed for the controlled expression of genes in cells, both prokaryotic and eukaryotic. These systems include the tetracycline-controlled transcriptional activation system (Tet-On/Tet-Off, Clontech, Inc. (Palo Alto, Calif.), the Lac Switch Inducible system (U.S. Pat. No. 4,833,080 to Brent et al., entitled "Regulation of eucaryotic gene expression"), the ecdysone-inducible gene expression system (No et al., Ecdysone-inducible gene expression in mammalian cells and transgenic mice, PNAS, 93(8):3346-3351 (1996)), and the cumate gene-switch system (Mullick, et al., The cumate gene-switch: a system for regulated expression in mammalian cells, BMC Biotechnology, 6:43 (2006)).

The cells that can be edited using the automated multi-module cell editing instruments of the illustrative embodiments include any prokaryotic, archaeal or eukaryotic cell. For example, prokaryotic cells for use with the present illustrative embodiments can be gram positive bacterial cells, e.g., *Bacillus subtilis*, or gram negative bacterial cells, e.g., *E. coli* cells. Eukaryotic cells for use with the automated multi-module cell editing instruments of the illustrative embodiments include any plant cells and any animal cells, e.g. fungal cells, insect cells, amphibian cells nematode cells, or mammalian cells.

Zinc-Finger Nuclease Genome Editing

In selected embodiments, the automated multi-module cell editing instruments described herein perform zinc-finger nuclease genome editing. Zinc-finger nucleases (ZFNs) are artificial restriction enzymes generated by fusing a zinc finger DNA-binding domain to a DNA-cleavage domain. Zinc finger domains can be engineered to target-specific regions in an organism's genome. (Urnov et al., Nature Reviews Genetics, 11:636-646 (2010); International Patent Application Publication WO 2003/087341 A2 to Carroll et al., entitled "Targeted Chromosomal Mutagenesis Using Zinc Finger Nucleases," filed Jan. 22, 2003). Using the endogenous DNA repair machinery of an organism, ZFNs can be used to precisely alter a target region of the genome. ZFNs can be used to disable dominant mutations in heterozygous individuals by producing double-strand breaks ("DSBs") in the DNA in the mutant allele, which will, in the absence of a homologous template, be repaired by non-homologous end-joining (NHEJ). NHEJ repairs DSBs by joining the two ends together and usually produces no mutations, provided that the cut is clean and uncomplicated. (Dural et al., Zinc finger nucleases: custom-designed molecular scissors for genome engineering of plant and mammalian cells, Nucleic Acids Res., 33(18):5978-90 (2005)). This repair mechanism can be used to induce errors in the genome via indels or chromosomal rearrangement, often rendering the gene products coded at that location non-functional.

Alternatively, DNA can be introduced into a genome in the presence of exogenous double-stranded DNA fragments using homology dependent repair (HDR). The dependency of HDR on a homologous sequence to repair DSBs can be exploited by inserting a desired sequence within a sequence that is homologous to the flanking sequences of a DSB which, when used as a template by HDR system, leads to the creation of the desired change within the genomic region of interest.

Multiple pairs of ZFNs can also be used to completely remove entire large segments of genomic sequence (Lee et al., Genome Res., 20 (1): 81-9 (2009); and US Patent Application Publication 2011/0082093 A1 to Gregory et al. entitled "Methods and Compositions for Treating Trinucleotide Repeat Disorders," filed Jul. 28, 2010). Expanded CAG/CTG repeat tracts are the genetic basis for more than a dozen inherited neurological disorders including Huntington's disease, myotonic dystrophy, and several spinocerebellar ataxias. It has been demonstrated in human cells that ZFNs can direct DSBs to CAG repeats and shrink the repeat from long pathological lengths to short, less toxic lengths (Mittelman, et al., Zinc-finger directed double-strand breaks within CAG repeat tracts promote repeat instability in human cells, PNAS USA, 106 (24): 9607-12 (2009); and US Patent Application Publication 2013/0253040 A1 to Miller et al. entitled "Methods and Compositions for Treating Huntington's Disease," filed Feb. 28, 2013).

Meganuclease Genome Editing

In selected embodiments, the automated multi-module cell editing, modules instruments and systems described herein perform meganuclease genome editing. Meganucleases were identified in the 1990s, and subsequent work has shown that they are particularly promising tools for genome editing, as they are able to efficiently induce homologous recombination, generate mutations in coding or non-coding regions of the genome, and alter reading frames of the coding regions of genomes. (See, e.g., Epinat, et al., A novel engineered meganuclease induces homologous recombination in eukaryotic cells, e.g., yeast and mammalian cells, Nucleic Acids Research, 31(11): 2952-2962; and U.S. Pat. No. 8,921,332 to Choulika et al. entitled "Chromosomal Modification Involving the Induction of Double-stranded DNA Cleavage and Homologous Recombination at the Cleavage Site," issued Dec. 30, 2014.) The high specificity of meganucleases gives them a high degree of precision and much lower cell toxicity than other naturally occurring restriction enzymes.

Transcription Activator-Like Effector Nuclease Editing

In selected embodiments, the automated multi-module cell editing modules, instruments and systems described herein perform transcription activator-like effector nuclease editing. Transcription activator-like effector nucleases (TALENs) are restriction enzymes that can be engineered to cut specific sequences of DNA. They are made by fusing a TAL effector DNA-binding domain to a DNA cleavage domain (a nuclease which cuts DNA strands). Transcription activator-like effector nucleases (TALENs) can be engineered to bind to practically any desired DNA sequence, so when combined with a nuclease, DNA can be cut at specific locations. (See, e.g., Miller, et al., A TALE nuclease architecture for efficient genome editing, Nature Biotechnology, 29 (2): 143-8 (2011); Boch, Nature Biotech., TALEs of genome targeting, 29(2): 135-6 (2011); International Patent Application Publication WO 2010/079430 A1 to Bonas et al. entitled "Modular DNA-binding Domains and Methods of Use," filed Jan. 12, 2010; International Patent Application Publication WO 2011/072246 A2 to Voytas et al. entitled "TAL Effector-Mediated DNA Modification," filed Dec. 10, 2010).

Like ZFNs, TALENs can edit genomes by inducing DSBs. The TALEN-created site-specific DSBs at target regions are repaired through NHEJ or HDR, resulting in targeted genome edits. TALENs can be used to introduce indels, rearrangements, or to introduce DNA into a genome through NHEJ in the presence of exogenous double-stranded DNA fragments.

RNA-Guided Nuclease (RGN) Editing

In certain aspects, the genome editing of the automated multi-module cell editing instruments of the illustrative embodiments utilize clustered regularly interspaced short palindromic repeats (CRISPR) techniques, in which RNA-guided nucleases (RGNs) are used to edit specific target regions in an organism's genome. By delivering the RGN complexed with a synthetic guide RNA (gRNA) into a cell, the cell's genome can be cut at a desired location, allowing edits to the target region of the genome. The guide RNA helps the RGN proteins recognize and cut the DNA of the target genome region. By manipulating the nucleotide sequence of the guide RNA, the RGN system could be programmed to target any DNA sequence for cleavage.

The RGN system used with the automated multi-module cell editing instruments of the illustrative embodiments can perform genome editing using any RNA-guided nuclease system with the ability to both cut and paste at a desired target genomic region. In certain aspects, the RNA-guided nuclease system may use two separate RNA molecules as a gRNA, e.g., a CRISPR RNA (crRNA) and trans-activating CRISPR RNA (tracrRNA). In other aspects, the gRNA may be a single gRNA that includes both the crRNA and tracrRNA sequences.

In certain aspects, the genome editing both introduces a desired DNA change to a target region and removes the proto-spacer motif (PAM) region from the target region, thus precluding any additional editing of the genome at that target region, e.g., upon exposure to a RNA-guided nuclease complexed with a synthetic gRNA complementary to the target region. In this aspect, a first editing event can be, e.g., an RGN-directed editing event or a homologous recombination event, and cells having the desired edit can be selected using an RGN complexed with a synthetic gRNA complementary to the target region. Cells that did not undergo the first editing event will be cut, and thus will not continue to be viable under appropriate selection criteria. The cells containing the desired mutation will not be cut, as they will no longer contain the necessary PAM site, and will continue to grow and propagate in the automated multi-module cell editing instrument.

When the RGN protein system is used for selection, it is primarily the cutting activity that is needed; thus the RNA-guided nuclease protein system can either be the same as used for editing, or may be a RGN protein system that is efficient in cutting using a particular PAM site, but not necessarily efficient in editing at the site. One important aspect of the nuclease used for selection is the recognition of the PAM site that is replaced using the editing approach of the previous genome editing operation.

Genome Editing by Homologous Recombination

In other aspects, the genome editing of the automated multi-module cell editing instruments of the illustrative embodiments can utilize homologous recombination methods including the cre-lox technique and the FRET technique. Site-specific homologous recombination differs from general homologous recombination in that short specific DNA sequences, which are required for the recombinase recognition, are the only sites at which recombination occurs. Site-specific recombination requires specialized recombinases to recognize the sites and catalyze the recombination at these sites. A number of bacteriophage- and yeast-derived site-specific recombination systems, each comprising a recombinase and specific cognate sites, have been shown to work in eukaryotic cells for the purpose of DNA integration and are therefore applicable for use in the present invention, and these include the bacteriophage P1 Cre/lox, yeast FLP-FRT system, and the Dre system of the tyrosine family of site-specific recombinases. Such systems and methods of use are described, for example, in U.S. Pat. Nos. 7,422,889; 7,112,715; 6,956,146; 6,774,279; 5,677,177; 5,885,836; 5,654,182; and 4,959,317, which are incorporated herein by reference to teach methods of using such recombinases. Other systems of the tyrosine family such as bacteriophage lambda Int integrase, HK2022 integrase, and in addition systems belonging to the separate serine family of recombinases such as bacteriophage phiC31, R4Tp901 integrases are known to work in mammalian cells using their respective recombination sites, and are also applicable for use in the present invention. Exemplary methodologies for homologous recombination are described in U.S. Pat. Nos. 6,689,610; 6,204,061; 5,631,153; 5,627,059; 5,487,992; and 5,464,764, each of which is incorporated by reference in its entirety.

Instrument Architecture

Figure 1B:
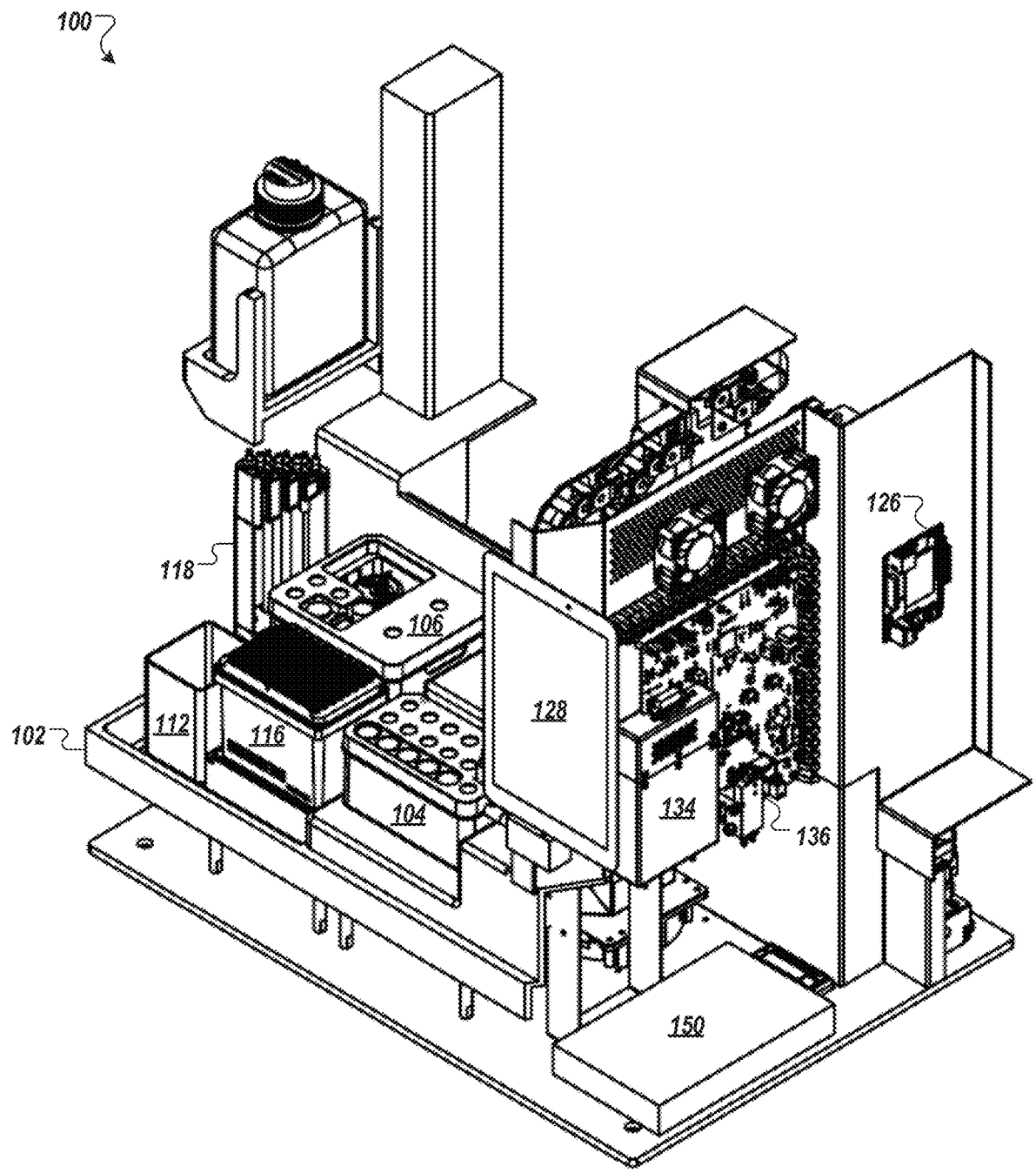

FIGS. 1A and 1B depict an example automated multi-module cell processing instrument 100 utilizing cartridge-based source materials (e.g., reagents, enzymes, nucleic acids, wash solutions, etc.). The instrument 100, for example, may be designed as a desktop instrument for use within a laboratory environment. The instrument 100 may incorporate a mixture of reusable and disposable elements for performing various staged operations in conducting automated genome cleavage and/or editing in cells. The cartridge-based source materials, for example, may be positioned in designated areas on a deck 102 of the instrument 100 for access by a robotic handling instrument 108. As illustrated in FIG. 1B, the deck 102 may include a protection sink such that contaminants spilling, dripping, or overflowing from any of the modules of the instrument 100 are contained within a lip of the protection sink.

Turning to FIG. 1A, the instrument 100, in some implementations, includes a reagent cartridge 104 for introducing DNA samples and other source materials to the instrument 100, a wash cartridge 106 for introducing eluent and other source materials to the instrument 100, and a robot handling system 108 for moving materials between modules (for example, modules 110a, 110b, and 110c) cartridge receptacles (for example, receptacles of cartridges 104 and 106), and storage units (e.g., units 112, 114, 116, and 118) of the instrument 100 to perform automated genome cleavage and/or editing. Upon completion of processing of the cell supply 106, in some embodiments, cell output may be transferred by the robot handling instrument 108 to a storage unit or receptacle placed in, e.g., reagent cartridge 104 or wash cartridge 106 for temporary storage and later retrieval.

The robotic handling system 108, for example, may include an air displacement pump 120 to transfer liquids from the various material sources of the cartridges 104, 106 to the various modules 110 and to the storage unit, which may be a receptacle in reagent cartridge 104 or wash cartridge 106. In other embodiments, the robotic handling system 108 may include a pick and place head (not illustrated) to transfer containers of source materials (e.g., tubes or vials) from the reagent cartridge 104 and/or the wash cartridge 106 to the various modules 110. In some embodiments, one or more cameras or other optical sensors (not shown) confirm proper movement and position of the robotic handling apparatus along a gantry 122.

In some embodiments, the robotic handling system 108 uses disposable transfer tips provided in a transfer tip supply 116 (e.g., pipette tip rack) to transfer source materials, reagents (e.g., nucleic acid assembly), and cells within the instrument 100. Used transfer tips 116, for example, may be discarded in a solid waste unit 112. In some implementations, the solid waste unit 112 contains a kicker to remove tubes, tips, vials, and/or filters from the pick and place head of robotic handling system 108. For example, as illustrated the robotic handling system 108 includes a filter pickup head 124.

In some embodiments, the instrument 100 includes electroporator cuvettes with sippers that connect to the air displacement pump 120. In some implementations, cells and reagent are aspirated into the electroporation cuvette through a sipper, and the cuvette is moved to one or more modules 110 of the instrument 100.

Figure 13:
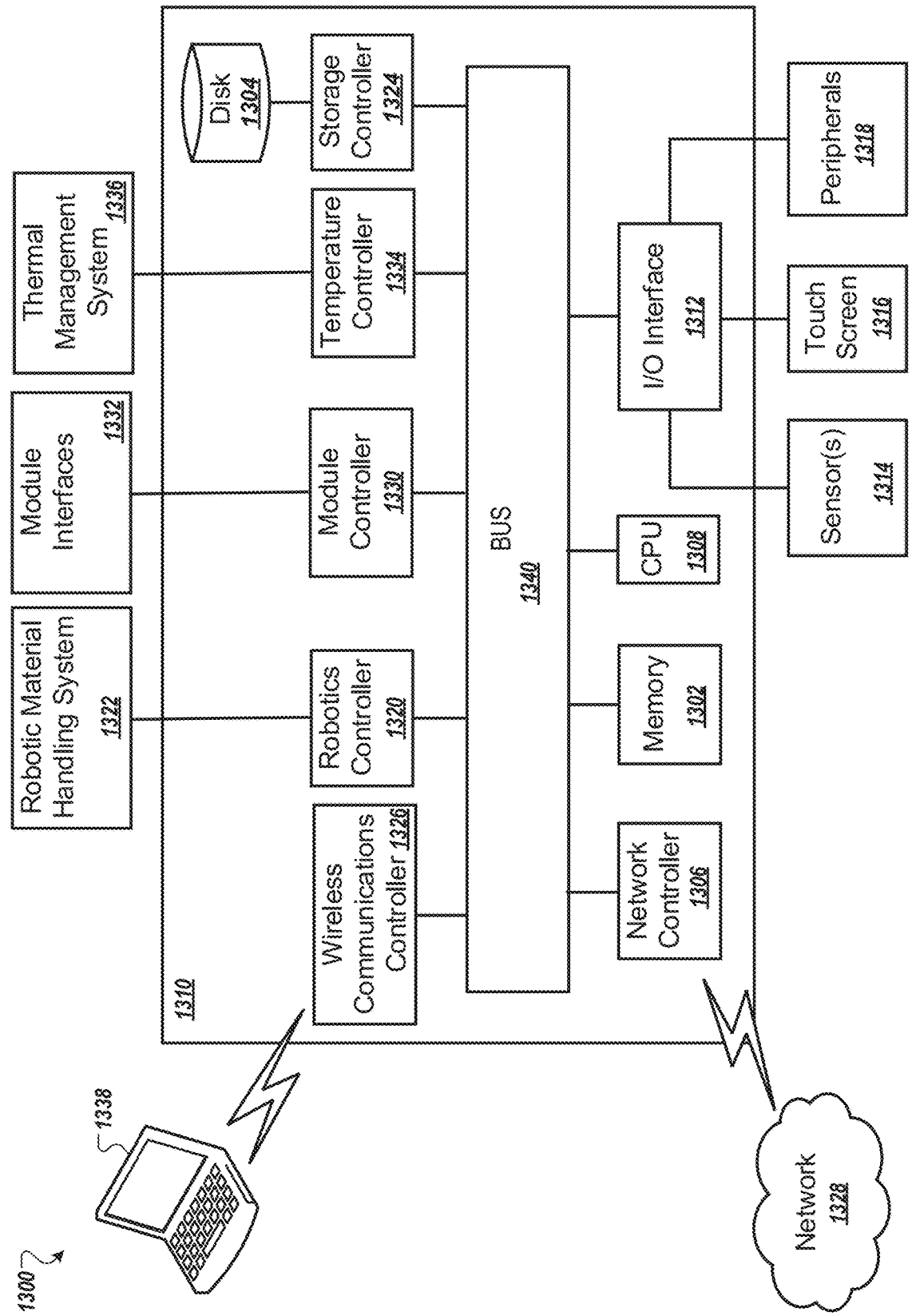
FIG. 13 is an example control system for use in an automated multi-mode cell processing instrument.

In some implementations, the instrument 100 is controlled by a processing system 126 such as the processing system 1310 of FIG. 13. The processing system 126 may be configured to operate the instrument 100 based on user input. For example, user input may be received by the instrument 100 through a touch screen control display 128. The processing system 126 may control the timing, duration, temperature and other operations of the various modules 110 of the instrument 100. Turning to FIG. 1B, the processing system 126 may be connected to a power source 150 for the operation of the instrument 100.

Returning to FIG. 1A, the reagent cartridge 104, as illustrated, includes sixteen reservoirs (a matrix of 5×3 reservoirs, plus an additional reservoir) and a flow-through transformation module (electroporation device) 110c. The wash cartridge 106 may be configured to accommodate large tubes or reservoirs to store, for example, wash solutions, or solutions that are used often throughout an iterative process. Further, in some embodiments, the wash cartridge 106 may include a number of smaller tubes, vials, or reservoirs to retain smaller volumes of, e.g., source media as well as a receptacle or repository for edited cells. For example, the wash cartridge 106 may be configured to remain in place when two or more reagent cartridges 104 are sequentially used and replaced. Although the reagent cartridge 104 and wash cartridge 106 are shown in FIG. 1A as separate cartridges, in other embodiments, the contents of the wash cartridge 106 may be incorporated into the reagent cartridge 104. In further embodiments, three or more cartridges may be loaded into the automated multi-module cell processing instrument 100. In certain embodiments, the reagent cartridge 104, wash cartridge 106, and other components of the modules 110 in the automated multi-module cell processing instrument 100 are packaged together in a kit.

The wash and reagent cartridges 104, 106, in some implementations, are disposable kits provided for use in the automated multi-module cell processing instrument 100. For example, the user may open and position each of the reagent cartridge 104 and the wash cartridge 106 within a chassis of the automated multi-module cell processing instrument prior to activating cell processing. Example chassis are discussed in further detail below in relation to FIGS. 2A through 2D.

Components of the cartridges 104, 106, in some implementations, are marked with machine-readable indicia, such as bar codes, for recognition by the robotic handling system 108. For example, the robotic handling system 108 may scan containers within each of the cartridges 104, 106 to confirm contents. In other implementations, machine-readable indicia may be marked upon each cartridge 104, 106, and the processing system of the automated multi-module cell processing instrument 100 may identify a stored materials map based upon the machine-readable indicia.

Figure 6B:
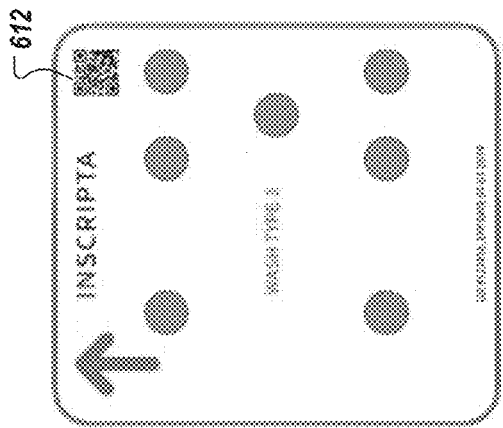
FIGS. 6A-6B depict an example wash cartridge for use in an automated multi-module cell processing instrument.
Figure 6A:
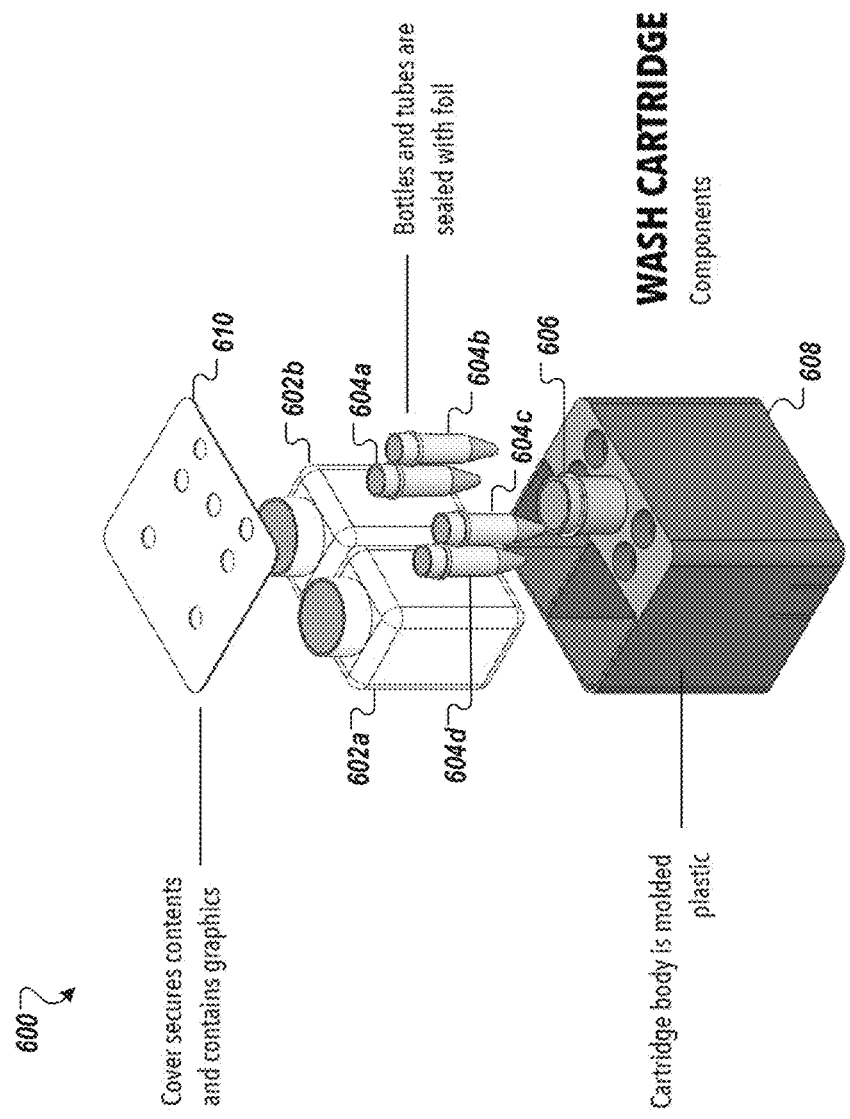

Turning to FIGS. 6A-6B, in some embodiments, the wash cartridge 106 is a wash cartridge 600 including a pair of large bottles 602, a set of four small tubes 604, and a large tube 606 held in a cartridge body 608. Each of the bottles 602 and tubes 604, 606, in some embodiments, is sealed with a pierceable foil for access by an automated liquid handling system, such as a sipper or pipettor. In other embodiments, each of the bottles 602 and tubes 604, 606 includes a sealable access gasket. The top of each of the bottles 602 and tubes 604, 606, in some embodiments, is marked with machine-readable indicia (not illustrated) for automated identification of the contents.

In some embodiments, the large bottles 602 each contain wash solution. The wash solution may be a same or different wash solutions. In some examples, wash solutions may contain, e.g., buffer, buffer and 10% glycerol, 80% ethanol.

In some implementations, a cover 610 secures the bottles 602 and tubes 604, 606 within the cartridge body 608. Turning to FIG. 6B, the cover 610 may include apertures for access to each of the bottles 602 and tubes 604, 606. Further, the cover 610 may include machine-readable indicia 612 for identifying the type of cartridge (e.g., accessing a map of the cartridge contents). Alternatively, each aperture may be marked separately with the individual contents.

Figure 6C:
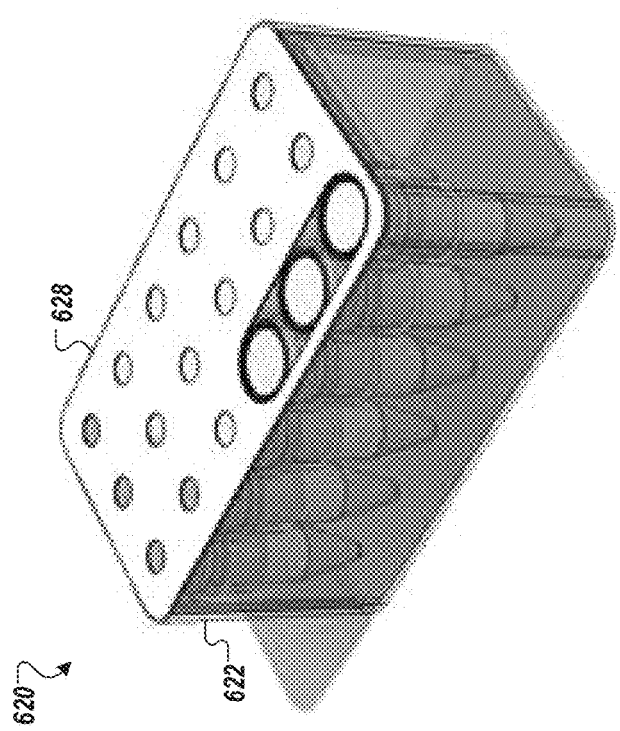
FIGS. 6C-6E depict an example reagent cartridge for use in an automated multi-module cell processing instrument.
Figure 6D:
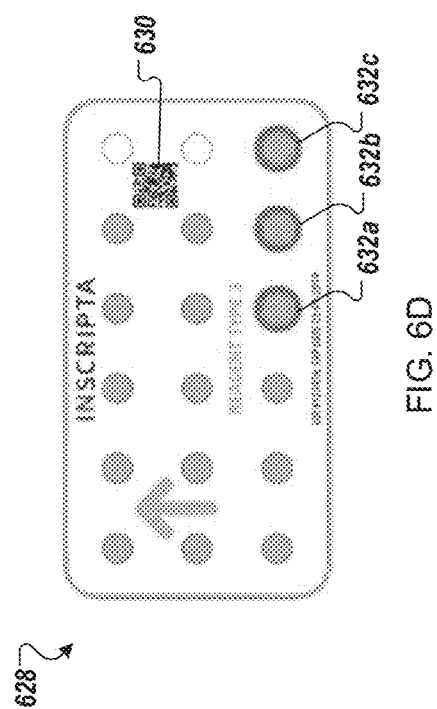
Figure 6E:
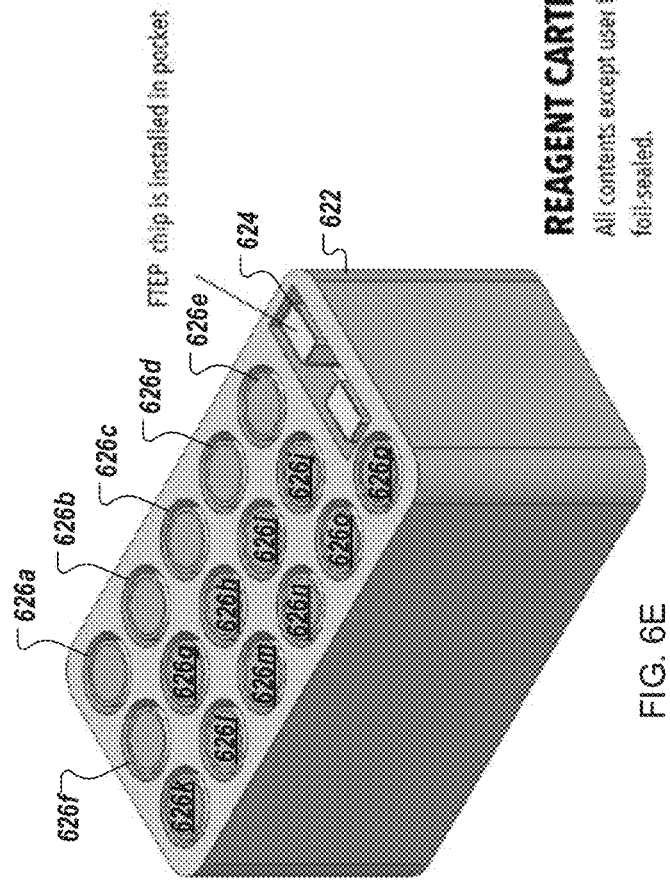

Turning to FIGS. 6C-E, in some implementations, the reagent cartridge 104 is a reagent cartridge 620 including a set of sixteen small tubes or vials 626, and flow-through electroporation module 624, held in a cartridge body 622. Each of the small tubes or vials 626, in some embodiments, is sealed with pierceable foil for access by an automated liquid handling system, such as a sipper or pipettor. In other embodiments, each of the small tubes or vials 626 includes a sealable access gasket. The top of each of the small tubes or vials 626, in some embodiments, is marked with machine-readable indicia (not illustrated) for automated identification of the contents. The machine-readable indicia may include a bar code, QR code, or other machine-readable coding. Other automated means for identifying a particular container can include color coding, symbol recognition (e.g., text, image, icon, etc.), and/or shape recognition (e.g., a relative shape of the container). Rather than being marked upon the vessel itself, in some embodiments, an upper surface of the cartridge body and/or the cartridge cover may contain machine-readable indicia for identifying contents. The small tubes or vials may each be of a same size. Alternatively, multiple volumes of tubes or vials may be provided in the reagent cartridge 620. In an illustrative example, each tube or vial may be designed to hold between 2 and 20 mL, between 4 and 10 mL, or about 5 mL.

In an illustrative example, the small tubes or vials 626 may each hold one the following materials: a vector backbone, oligonucleotides, reagents for isothermal nucleic acid assembly, a user-supplied cell sample, an inducer agent, magnetic beads in buffer, ethanol, an antibiotic for cell selection, reagents for eluting cells and nucleic acids, an oil overlay, other reagents, and cell growth and/or recovery media.

In some implementations, a cover 628 secures the small tubes or vials 626 within the cartridge body 622. Turning to FIG. 6D, the cover 628 may include apertures for access to each of the small tubes or vials 626. Three large apertures 632 are outlined in a bold (e.g., blue) band to indicate positions to add user-supplied materials. The user-supplied materials, for example, may include a vector backbone, oligonucleotides, and a cell sample. Further, the cover 610 may include machine-readable indicia 630 for identifying the type of cartridge (e.g., accessing a map of the cartridge contents). Alternatively, each aperture may be marked separately with the individual contents. In some implementations, to ensure positioning of user-supplied materials, the vials or tubes provided for filling in the lab environment may have unique shapes or sizes such that the cell sample vial or tube only fits in the cell sample aperture, the oligonucleotides vial or tube only fits in the oligonucleotides aperture, and so on.

Turning back to FIG. 1A, also illustrated is the robotic handling system 108 including the gantry 122. In some examples, the robotic handling system 108 may include an automated liquid handling system such as those manufactured by Tecan Group Ltd. of Mannedorf, Switzerland, Hamilton Company of Reno, Nev. (see, e.g., WO2018015544A1 to Ott, entitled "Pipetting device, fluid processing system and method for operating a fluid processing system"), or Beckman Coulter, Inc. of Fort Collins, Colo. (see, e.g., US20160018427A1 to Striebl et al., entitled "Methods and systems for tube inspection and liquid level detection"). The robotic handling system 108 may include an air displacement pipettor 120. The reagent cartridges 104, 106 allow for particularly easy integration with the liquid handling instrumentation of the robotic handling system 108 such as air displacement pipettor 120. In some embodiments, only the air displacement pipettor 120 is moved by the gantry 122 and the various modules 110 and cartridges 104, 106 remain stationary. Pipette tips 116 may be provided for use with the air displacement pipettor 120.

In some embodiments, an automated mechanical motion system (actuator) (not shown) additionally supplies XY axis motion control or XYZ axis motion control to one or more modules 110 and/or cartridges 104, 106 of the automated multi-module cell processing system 100. Used pipette tips 116, for example, may be placed by the robotic handling system in a waste repository 112. For example, an active module may be raised to come into contact-accessible positioning with the robotic handling system or, conversely, lowered after use to avoid impact with the robotic handling system as the robotic handling system is moving materials to other modules 110 within the automated multi-module cell processing instrument 100.

The automated multi-module cell processing instrument 100, in some implementations, includes the flow-through electroporation module 110c included in the reagent cartridge 104. A flow-through electroporation connection bridge 132, for example, is engaged with the flow-through electroporation device after the cells and nucleic acids are transferred into the device via an input channel. The bridge 132 provides both a liquid-tight seal and an electrical connection to the electrodes, as well as control for conducting electroporation within the electroporation module 110c. For example, the electroporation connection bridge 132 may be connected to flow-through electroporation controls 134 within an electronics rack 136 of the automated multi-module cell processing instrument 100.

In some implementations, the automated multi-module cell processing instrument 100 includes dual cell growth modules 110a, 110b. The cell growth modules 110a, 110b, as illustrated each include a rotating cell growth vial 130a, 130b. At least one of the cell growth modules 110a, 110b may additionally include an integrated filtration module (not illustrated). In alternative embodiments, a filtration module or a cell wash and concentration module may instead be separate from cell growth modules 110a, 110b (e.g., as described in relation to cell growth module 1210a and filtration module 1210b of FIGS. 12A and 12B). The cell growth modules 110a, 110b, for example, may each include the features and functionalities discussed in relation to the cell growth module 800 of FIGS. 8A-F.

A filtration portion of one or both of the cell growth modules 110a, 110b, in some embodiments, use replaceable filters stored in a filter cassette 118. For example, the robotic handling system may include the filter pick-up head 124 to pick up and engage filters for use with one or both of the cell growth modules 110a, 110b. The filter pick-up head transfers a filter to the growth module, pipettes up the cells from the growth module, then washes and renders the cells electrocompetent. The medium from the cells, and the wash fluids are disposed in waste module 114.

In some implementations, automated multi-module cell processing instrument 100 includes a nucleic acid assembly and purification function (e.g., nucleic acid assembly module) for combining materials provided in the reagent cartridge 104 into an assembled nucleic acid for cell editing. Further, a desalting or purification operation purifies the assembled nucleic acids and de-salts the buffer such that the nucleic acids are more efficiently electroporated into the cells. The nucleic acid assembly and purification feature may include a reaction chamber or tube receptacle (not shown) and a magnet (not shown).

Although the example instrument 100 is illustrated as including a particular arrangement of modules 110, this implementation is for illustrative purposes only. For example, in other embodiments, more or fewer modules 110 may be included within the instrument 100, and different modules may be included such as, e.g., a module for cell fusion to produce hybridomas and/or a module for protein production. Further, certain modules may be replicated within certain embodiments, such as the duplicate cell growth modules 110a, 110b of FIG. 1A.

In some embodiments, the cells are modified prior to introduction onto the automated multi-module cell editing instrument. For example, the cells may be modified by using a λ red system to replace a target gene with an antibiotic resistance gene, usually for kanamycin or chloramphenicol. (See Datsenko and Wanner, One-step inactivation of chromosomal genes in *Escherichia coli* K-12 using PCR products, PNAS USA, 97(12):6640-5 (2000); U.S. Pat. No. 6,509,156B1 to Stewart et al. entitled "DNA Cloning Method Relying on the *E. coli* recE/recT Recombination System," issued Jan. 21, 2003.) In some embodiments, the cells may have already been transformed or transfected with a vector comprising an expression cassette for a nuclease. In another example, a desired gene edit may be introduced to the cell population prior to introduction to the automated multi-module cell editing instrument (e.g., using homology directed repair), and the system used to select these edits using a nuclease and/or add additional edits to the cell population.

FIGS. 2A through 2D illustrate example chassis 200 and 230 for use in desktop versions of an automated multi-module cell processing instrument. For example, the chassis 200 and 230 may have a width of about 24-48 inches, a height of about 24-48 inches and a depth of about 24-48 inches. Each of the chassis 200 and 230 may be designed to hold multiple modules and disposable supplies used in automated cell processing. Further, each chassis 200 and 250 may mount a robotic handling system for moving materials between modules.

Figure 2B:
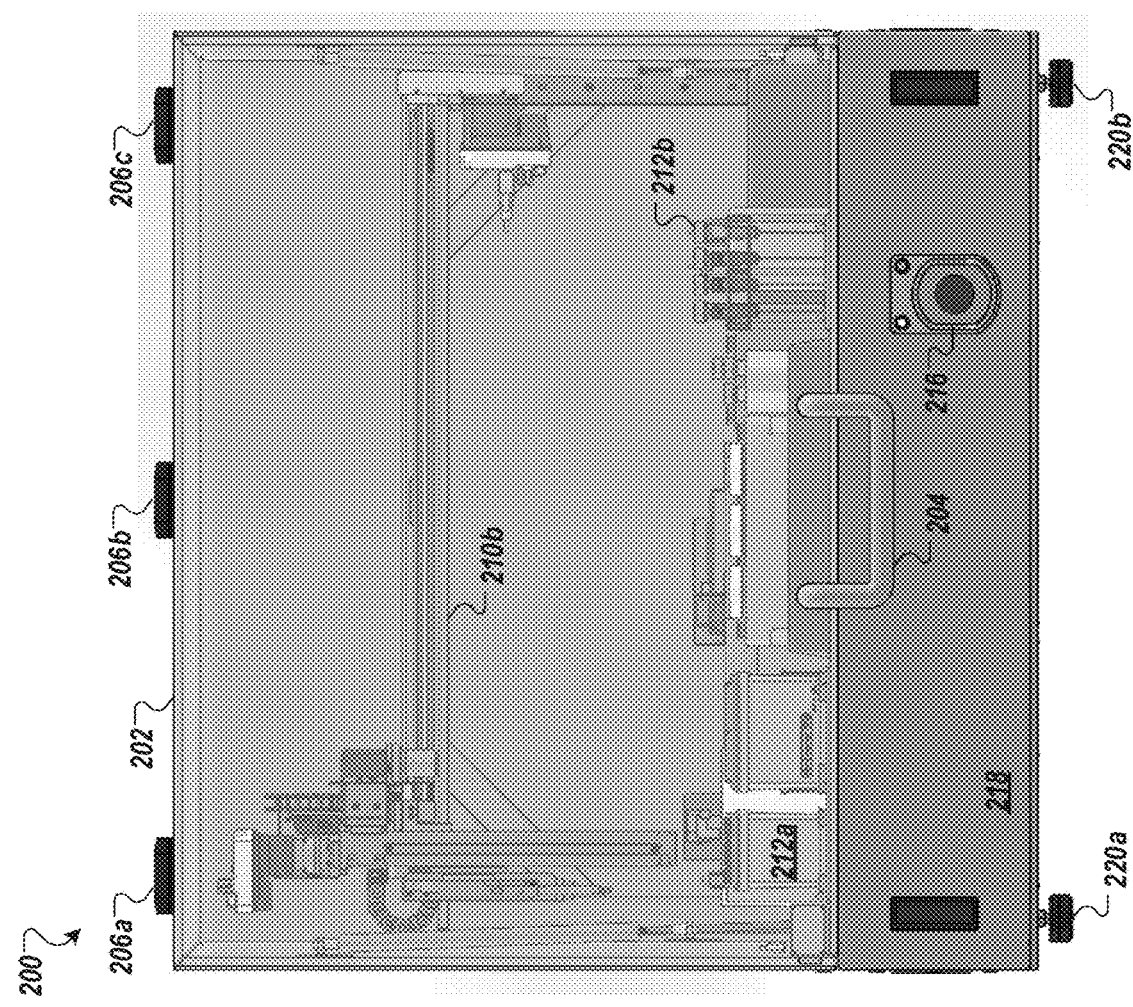
FIGS. 2A and 2B depict side and front views of the automated multi-module cell processing instrument of FIGS. 1A and 1B.
Figure 2A:
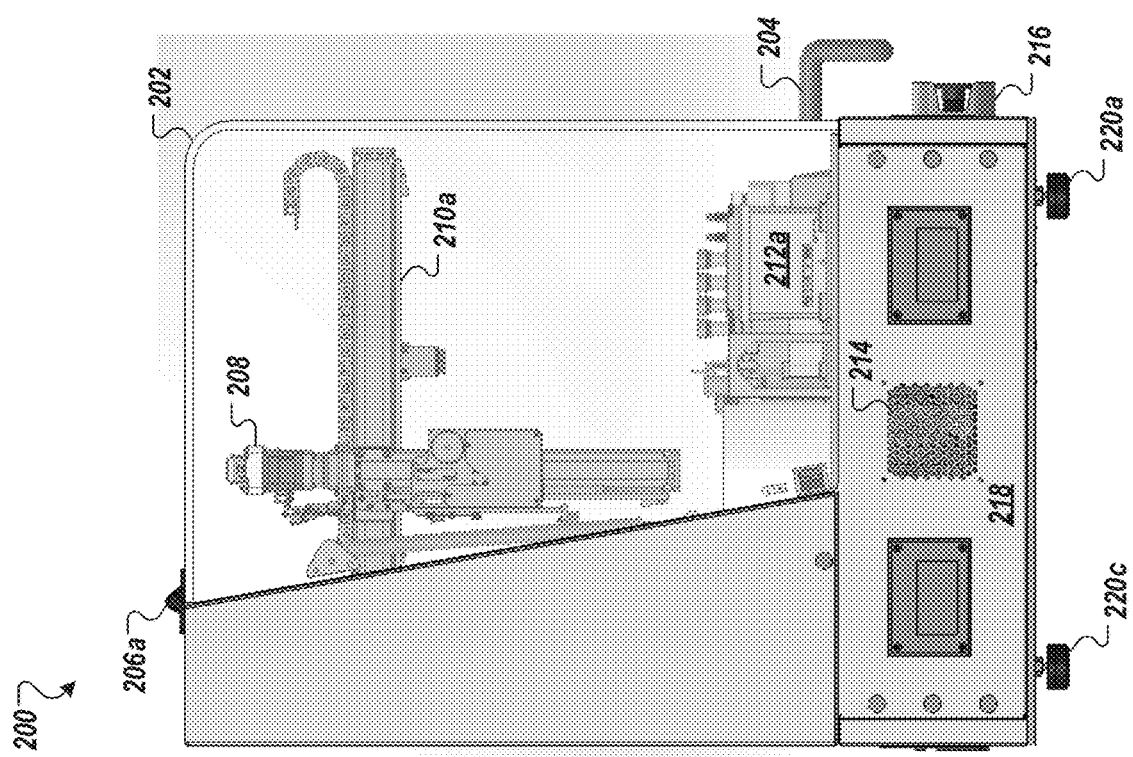

FIGS. 2A and 2B depict a first example chassis 200 of an automated multi-module cell processing instrument. As illustrated, the chassis 200 includes a cover 202 having a handle 204 and hinges 206 for lifting the cover 202 and accessing an interior of the chassis 200. A cooling grate 214 may allow for air flow via an internal fan (not shown). Further, the chassis 200 is lifted by adjustable feet 220. The feet 220, for example, may provide additional air flow beneath the chassis 200. A control button 216, in some embodiments, allows for single-button automated start and stop of cell processing within the chassis 200.

Inside the chassis 200, in some implementations, a robotic handling system 208 is disposed along a gantry 210 above materials cartridges 212a, 212b and modules. Control circuitry, liquid handling tubes, air pump controls, valves, thermal units (e.g., heating and cooling units) and other control mechanisms, in some embodiments, are disposed below a deck of the chassis 200, in a control box region 218.

Although not illustrated, in some embodiments, a display screen may be positioned upon a front face of the chassis 200, for example covering a portion of the cover 202. The display screen may provide information to the user regarding a processing status of the automated multi-module cell processing instrument. In another example, the display screen may accept inputs from the user for conducting the cell processing.

Figure 2C:
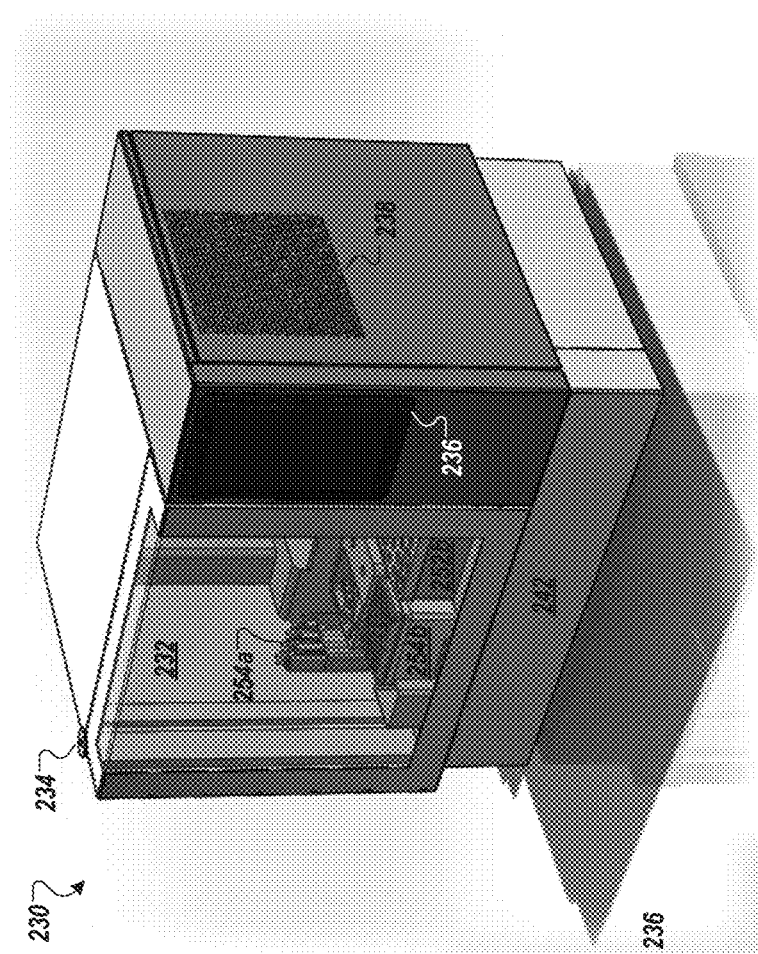
FIGS. 2C and 2D depict a second example chassis of an automated multi-module cell processing instrument.
Figure 2D:
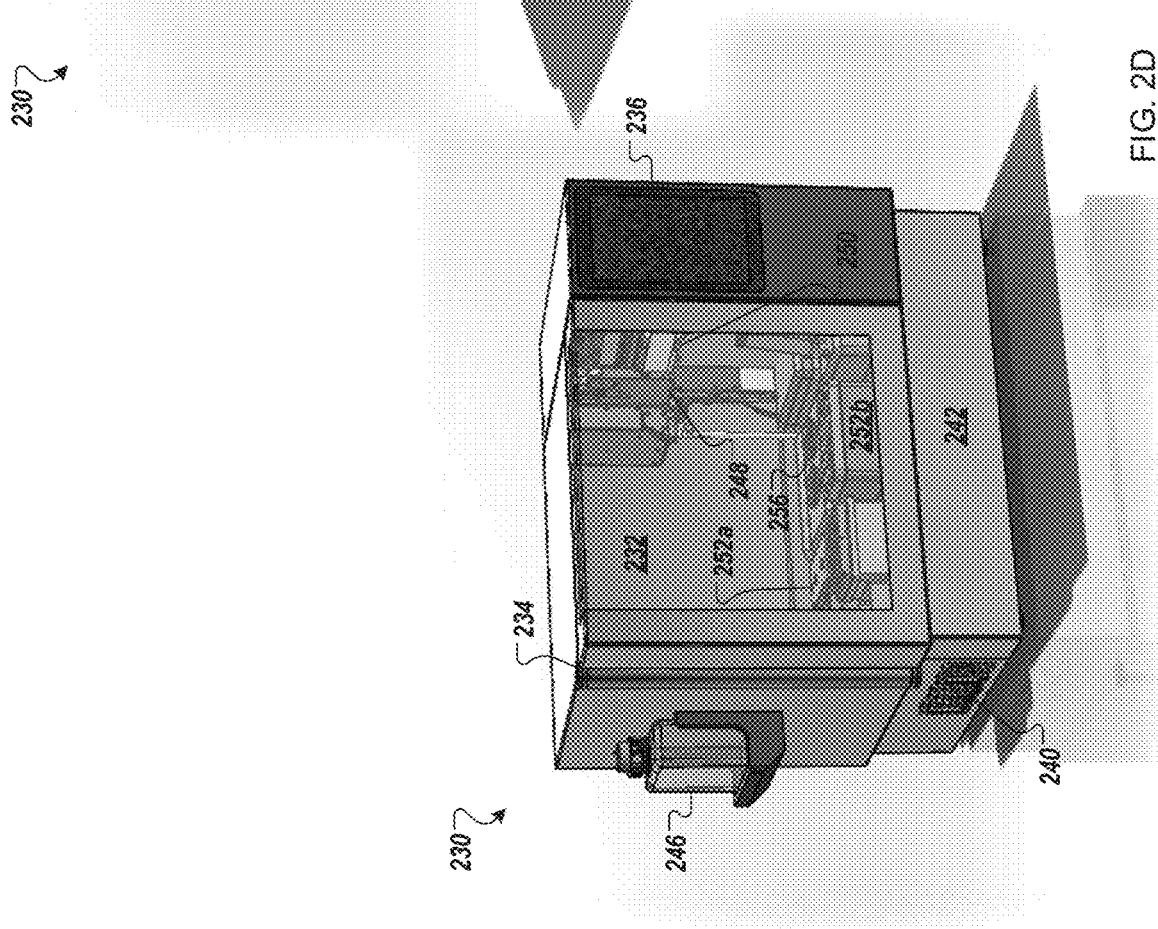

FIGS. 2C and 2D depict a second example chassis 230 of an automated multi-module cell processing instrument. The chassis 230, as illustrated, includes a transparent door 232 with a hinge 234. For example, the door may swing to the left of the page to provide access to a work area of the chassis. The user, for example, may open the transparent door 232 to load supplies, such as reagent cartridges and wash cartridges, into the chassis 230.

In some embodiments, a front face of the chassis 230 further includes a display (e.g., touch screen display device) 236 illustrated to the right of the door 232. The display 236 may provide information to the user regarding a processing status of the automated multi-module cell processing instrument. In another example, the display 236 may accept inputs from the user for conducting the cell processing.

An air grate 238 on a right face of the chassis 230 may provide for air flow within a work area (e.g., above the deck) of the chassis 230 (e.g., above a deck). A second air grate 240 on a left of the chassis 230 may provide for air flow within a control box region 242 (e.g., below the deck) of the chassis 230. Although not illustrated, in some embodiments, feet such as the feet 220 of the chassis 200 may raise the chassis 230 above a work surface, providing for further air flow.

Inside the chassis 230, in some implementations, a robotic handling system 248 is disposed along a gantry 250 above cartridges 252a, 252b, material supplies 254a, 254b (e.g., pipette tips and filters), and modules 256 (e.g., dual growth vials). Control circuitry, liquid handling tubes, air pump controls, valves, and other control mechanisms, in some embodiments, are disposed below a deck of the chassis 230, in the control box region 242.

In some embodiments, a liquid waste unit 246 is mounted to the left exterior wall of the chassis 230. The liquid waste unit 246, for example, may be mounted externally to the chassis 230 to avoid potential contamination and to ensure prompt emptying and replacement of the liquid waste unit 246.

Nucleic Acid Assembly Module

Certain embodiments of the automated multi-module cell editing instruments of the present disclosure include a nucleic acid assembly module within the instrument. The nucleic acid assembly module is configured to accept the nucleic acids necessary to facilitate the desired genome editing events. The nucleic acid assembly module may also be configured to accept the appropriate vector backbone for vector assembly and subsequent transformation into the cells of interest.

In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that include one or more free ends, no free ends (e.g. circular); nucleic acid molecules that include DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, where virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Further discussion of vectors is provided herein.

Recombinant expression vectors can include a nucleic acid in a form suitable for transformation, and for some nucleic acids sequences, translation and expression of the nucleic acid in a host cell, which means that the recombinant expression vectors include one or more regulatory elements—which may be selected on the basis of the host cells to be used for expression—that are operatively-linked to the nucleic acid sequence to be expressed. Within a recombinant expression vector, "operably linked" is intended to mean that the nucleotide sequence of interest is linked to the regulatory element(s) in a manner that allows for transcription, and for some nucleic acid sequences, translation and expression of the nucleotide sequence (e.g. in an in vitro transcription/translation system or in a host cell when the vector is introduced into the host cell). Appropriate recombination and cloning methods are disclosed in U.S. patent application Ser. No. 10/815,730, entitled "Recombinational Cloning Using Nucleic Acids Having Recombination Sites" published Sep. 2, 2004 as US 2004-0171156 A1, the contents of which are herein incorporated by reference in their entirety for all purposes.

In some embodiments, a regulatory element is operably linked to one or more elements of a targetable nuclease system so as to drive transcription, and for some nucleic acid sequences, translation and expression of the one or more components of the targetable nuclease system.

In some embodiments, a vector may include a regulatory element operably linked to a polynucleotide sequence encoding a nucleic acid-guided nuclease. The polynucleotide sequence encoding the nucleic acid-guided nuclease can be codon optimized for expression in particular cells, such as prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammal including non-human primate. In addition or alternatively, a vector may include a regulatory element operably liked to a polynucleotide sequence, which, when transcribed, forms a guide RNA.

The nucleic acid assembly module can be configured to perform a wide variety of different nucleic acid assembly techniques in an automated fashion. Nucleic acid assembly techniques that can be performed in the nucleic acid assembly module of the disclosed automated multi-module cell editing instruments include, but are not limited to, those assembly methods that use restriction endonucleases, including PCR, BioBrick assembly (U.S. Pat. No. 9,361,427 to Hillson entitled "Scar-less Multi-part DNA Assembly Design," issued Jun. 7, 2016), Type IIS cloning (e.g., GoldenGate assembly; European Patent Application Publication EP 2 395 087 A1 to Weber et al. entitled "System and Method of Modular Cloning," filed Jul. 6, 2010), and Ligase Cycling Reaction (de Kok S, Rapid and Reliable DNA Assembly via Ligase Cycling Reaction, ACS Synth Biol., 3(2):97-106 (2014); Engler, et al., PLoS One, A One Pot, One Step, Precision Cloning Method with High Throughput Capability, 3(11):e3647 (2008); U.S. Pat. No. 6,143,527 to Pachuk et al. entitled "Chain Reaction Cloning Using a Bridging Oligonucleotide and DNA Ligase," issued Nov. 7, 2000). In other embodiments, the nucleic acid assembly techniques performed by the disclosed automated multi-module cell editing instruments are based on overlaps between adjacent parts of the nucleic acids, such as Gibson Assembly®, CPEC, SLIC, Ligase Cycling etc. Additional assembly methods include gap repair in yeast (Bessa, Improved gap repair cloning in yeast: treatment of the gapped vector with Taq DNA polymerase avoids vector self-ligation, Yeast, 29(10):419-23 (2012)), gateway cloning (Ohtsuka, Lantibiotics: mode of action, biosynthesis and bioengineering, Curr Pharm Biotechnol, 10(2):244-51 (2009); U.S. Pat. No. 5,888,732 to Hartley et al., entitled "Recombinational Cloning Using Engineered Recombination Sites," issued Mar. 30, 1999; U.S. Pat. No. 6,277,608 to Hartley et al. entitled "Recominational Cloning Using Nucleic Acids Having Recombination Sites," issued Aug. 21, 2001), and topoisomerase-mediated cloning (Udo, An Alternative Method to Facilitate cDNA Cloning for Expression Studies in Mammalian Cells by Introducing Positive Blue White Selection in Vaccinia Topoisomerase I-Mediated Recombination, PLoS One, 10(9):e0139349 (2015); U.S. Pat. No. 6,916,632 B2 to Chestnut et al. entitled "Methods and Reagents for Molecular Cloning," issued Jul. 12, 2005). These and other nucleic acid assembly techniques are described, e.g., in Sands and Brent, Overview of Post Cohen-Boyer Methods for Single Segment Cloning and for Multisegment DNA Assembly, Curr Protoc Mol Biol., 113: 3.26.1-3.26.20 (2016); Casini et al., Bricks and blueprints: methods and standards for DNA assembly, Nat Rev Mol Cell Biol., (9):568-76 (2015); Patron, DNA assembly for plant biology: techniques and tools, Curr Opinion Plant Biol., 19:14-9 (2014)).

The nucleic acid assembly is temperature controlled depending upon the type of nucleic acid assembly used in the automated multi-module cell editing instrument. For example, when PCR is utilized in the nucleic acid assembly module, the module will have a thermocycling capability allowing the temperatures to cycle between denaturation, annealing and extension. When single temperature assembly methods are utilized in the nucleic acid assembly module, the module will have the ability to reach and hold at the temperature that optimizes the specific assembly process being performed. These temperatures and the duration for maintaining these temperatures can be determined by a preprogrammed set of parameters executed by a script, or manually controlled by the user using the processing system of the automated multi-module cell processing instrument.

Figure 4:
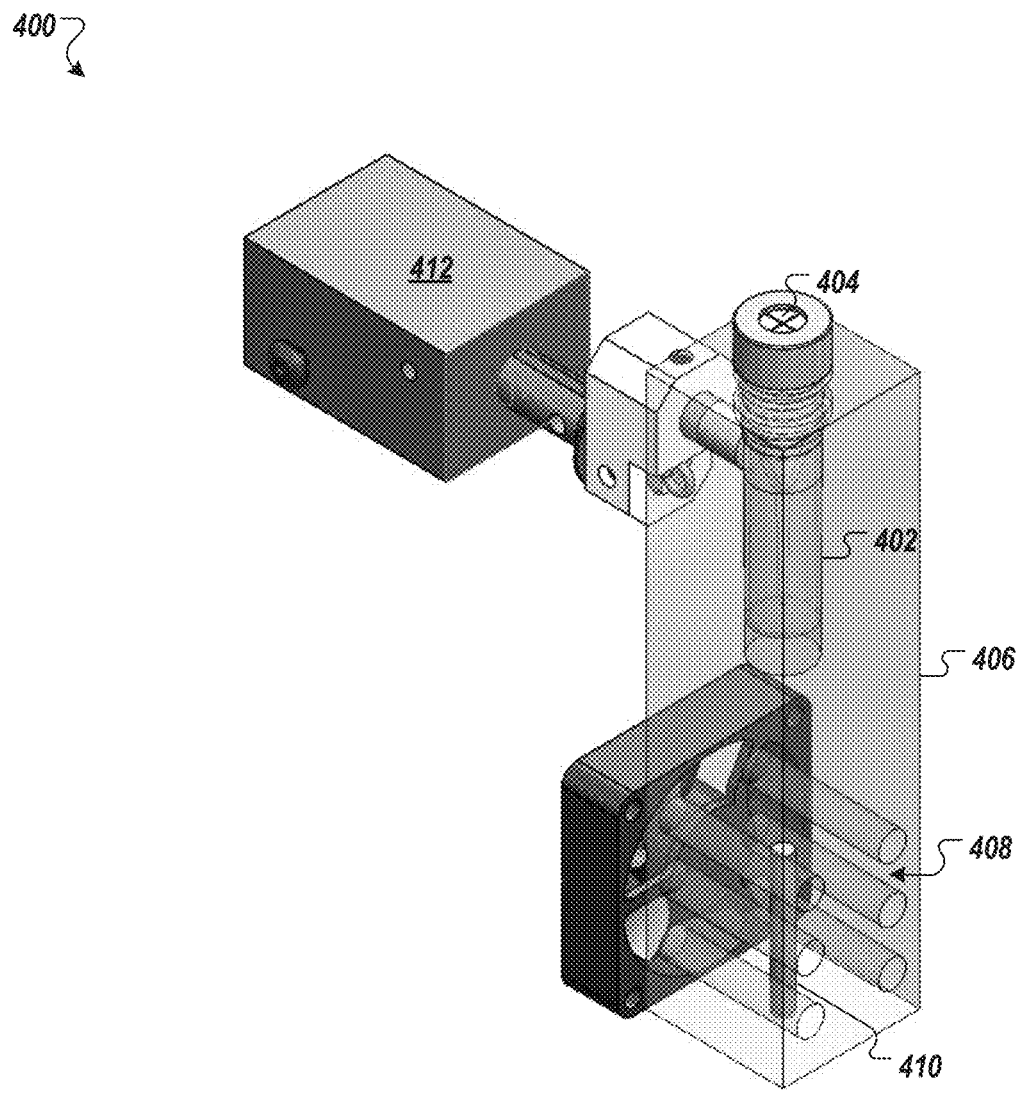
FIG. 4 depicts an example combination nucleic acid assembly module and purification module for use in an automated multi-module cell processing instrument.

In one embodiment, the nucleic acid assembly module is a module to perform assembly using a single, isothermal reaction, such as that illustrated in FIG. 4. The isothermal assembly module is configured to perform the molecular cloning method using the single, isothermal reaction. Certain isothermal assembly methods can combine simultaneously up to 15 nucleic acid fragments based on sequence identity. The assembly method provides, in some embodiments, nucleic acids to be assembled which include an approximate 20-40 base overlap with adjacent nucleic acid fragments. The fragments are mixed with a cocktail of three enzymes-an exonuclease, a polymerase, and a ligase-along with buffer components. Because the process is isothermal and can be performed in a 1-step or 2-step method using a single reaction vessel, isothermal assembly reactions are ideal for use in an automated multi-module cell processing instrument. The 1-step method allows for the assembly of up to five different fragments using a single step isothermal process. The fragments and the master mix of enzymes are combined and incubated at 50° C. for up to one hour. For the creation of more complex constructs with up to fifteen fragments or for incorporating fragments from 100 bp up to 10 kb, typically the 2-step is used, where the 2-step reaction requires two separate additions of master mix; one for the exonuclease and annealing step and a second for the polymerase and ligation steps.

FIG. 4 illustrates an example isothermal nucleic acid assembly module 400 with integrated purification. The isothermal nucleic acid assembly module 400 includes a chamber 402 having an access gasket 404 for transferring liquids to and from the isothermal nucleic acid assembly module 400 (e.g., via a pipette or sipper). In some embodiments, the access gasket 404 is connected to a replaceable vial which is positioned within the chamber 402. For example, a user or robotic manipulation system may place the vial within the isothermal nucleic acid assembly module 400 for processing.

The chamber 402 shares a housing 406 with a resistive heater 408. Once a sample has been introduced to the chamber 402 of the isothermal nucleic acid assembly module 400, the resistive heater 408 may be used to heat the contents of the chamber 402 to a desired temperature. Thermal ramping may be set based upon the contents of the chamber 402 (e.g., the materials supplied through the access gasket 404 via pipettor or sipper unit of the robotic manipulation system). The processing system of the automated multi-module cell processing system may determine the target temperature and thermal ramping plan. The thermal ramping and target temperature may be controlled through monitoring a thermal sensor such as a thermistor 410 included within the housing 406. In a particular embodiment, the resistive heater 408 is designed to maintain a temperature within the housing 406 of between 20° and 80° C., between 25° and ° C., between 37° and 65° C., between 40° and 60° C., between 45° and 55° C. or preferably about 50° C.

Purification Module

In some embodiments, when a nucleic acid assembly module is included in the automated multi-module cell editing instrument, the instrument also can include a purification module to remove unwanted components of the nucleic acid assembly mixture (e.g., salts, minerals) and, in certain embodiments, concentrate the assembled nucleic acids. Examples of methods for exchanging the liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc.

In one aspect, the purification module provides filtration, e.g., ultrafiltration. For example, a range of microconcentrators fitted with anisotropic, hydrophilic-generated cellulose membranes of varying porosities is available. (See, e.g., Millipore SCX microconcentrators used in Juan, Li-Jung, et al. "Histone deacetylases specifically down-regulate p53-dependent gene activation." Journal of Biological Chemistry 275.27 (2000): 20436-20443). In another example, the purification and concentration involves contacting a liquid sample including the assembled nucleic acids and an ionic salt with an ion exchanger including an insoluble phosphate salt, removing the liquid, and eluting the nucleic acid from the ion exchanger.

In a specific aspect of the purification module, SPRI beads can be used where 0.6-2.0× volumes of SPRI beads can be added to the nucleic acid assembly. The nucleic acid assembly product becomes bound to the SPRI beads, and the SPRI beads are pelleted by automatically positioning a magnet close to the tube, vessel, or chamber harboring the pellet. For example, 0.6-2.0× volumes of SPRI beads can be added to the nucleic acid assembly. The SPRI beads, for example, may be washed with ethanol, and the bound nucleic acid assembly product is eluted, e.g., in water, Tris buffer, or 10% glycerol.

In a specific aspect, a magnet is coupled to a linear actuator that positions the magnet. In some implementations, the nucleic acid assembly module is a combination assembly and purification module designed for integrated assembly and purification. For example, as discussed above in relation to an isothermal nucleic acid assembly module, once sufficient time has elapsed for the isothermal nucleic acid assembly reaction to take place, the contents of the chamber 402 (e.g., the isothermal nucleic acid assembly reagents and nucleic acids), in some embodiments, are combined with magnetic beads (not shown) to activate the purification process. The SPRI beads in buffer are delivered to the contents of the isothermal nucleic acid assembly module, for example, by a robotic handling system. Thereafter, a solenoid 412, in some embodiments, is actuated by a magnet to excite the magnetic beads contained within the chamber 402. The solenoid, in a particular example, may impart between a 2 pound magnetic pull force and a 5 pound pull force, or approximately a 4 pound magnetic pull force to the magnetic beads within the chamber 402. The contents of the chamber 402 may be incubated for sufficient time for the assembled vector and oligonucleotides to bind to the magnetic beads.

After binding, in some implementations, the bound isothermal nucleic acid assembly mix (e.g., isothermal nucleic acid assembly reagents+assembled vector and oligonucleotides) is removed from the isothermal nucleic acid assembly module and the nucleic acids attached to the beads are washed one to several times with 80% ethanol. Once washed, the nucleic acids attached to the beads are eluted into buffer and are transferred to the transformation module.

In some implementations, a vial is locked in position in the chamber 402 for processing. For example, a user may press the vial beyond a detent in the chamber 402 designed to retain the vial upon engagement with a pipettor or sipper. In another example, the user may twist the vial into position, thus engaging a protrusion to a corresponding channel and barring upward movement. A position sensor (not illustrated) may ensure retraction of the vial. The position sensor, in a particular embodiment, is a magnetic sensor detecting engagement between a portion of the chamber 402 and the vial. In other embodiments, the position sensor is an optical sensor detecting presence of the vial at a retracted position. In embodiments using a channel and protrusion, a mechanic switch pressed down by the protrusion may detect engagement of the vial.

Growth Module

As the nucleic acids are being assembled, the cells may be grown in preparation for editing. The cell growth can be monitored by optical density (e.g., at OD 600 nm) that is measured in a growth module, and a feedback loop is used to adjust the cell growth so as to reach a target OD at a target time. Other measures of cell density and physiological state that can be measured include but are not limited to, pH, dissolved oxygen, released enzymes, acoustic properties, and electrical properties.

In some aspects, the growth module includes a culture tube in a shaker or vortexer that is interrogated by a spectrophotometer or fluorimeter. The shaker or vortexer can heat or cool the cells and cell growth is monitored by real-time absorbance or fluorescence measurements. In one aspect, the cells are grown at 25° C.-40° C. to an OD600 absorbance of 1-10 ODs. The cells may also be grown at temperature ranges from 25° C.-35° C., 25° C.-30° C., 30° C.-40° C., 30° C.-35° C., 35° C.-40° C., 40° C.-50° C., 40° C.-45° C. or 44° C.-50° C. In another aspect, the cells are induced by heating at 42° C.-50° C. or by adding an inducing agent. The cells may also be induced by heating at ranges from 42° C.-46° C., 42° C.-44° C., 44° C.-46° C., 44° C.-48° C., 46° C.-48° C., 46° C.-50° C., or 48° C.-50° C. In some aspects, the cells are cooled to 0° C.-10° C. after induction. The cells may also be cooled to temperature ranges of 0° C.-5° C., 0° C.-2° C., 2° C.-4° C., 4° C.-6° C., 6° C.-8° C., 8° C.-10° C., or 5° C.-10° C. after induction.

Figure 8A:
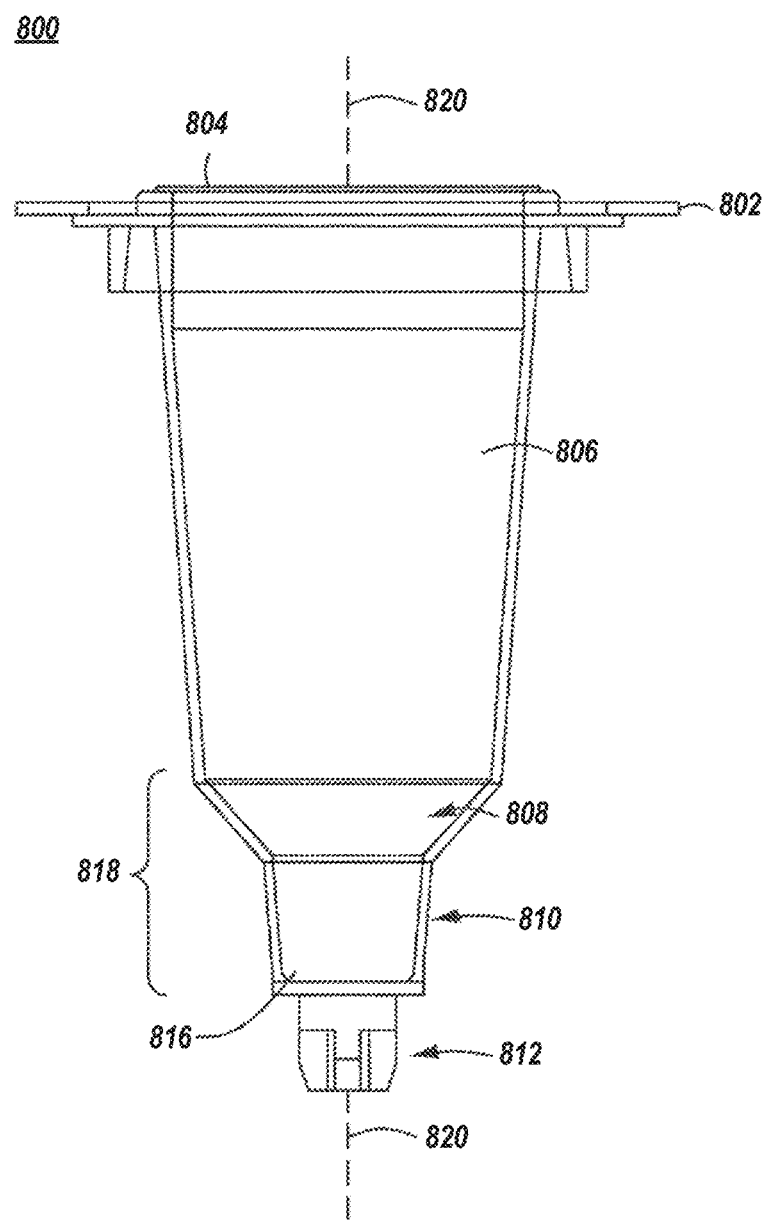
FIGS. 8A-8F depict example cell growth modules for use in an automated multi-module cell processing instrument.
Figure 8B:
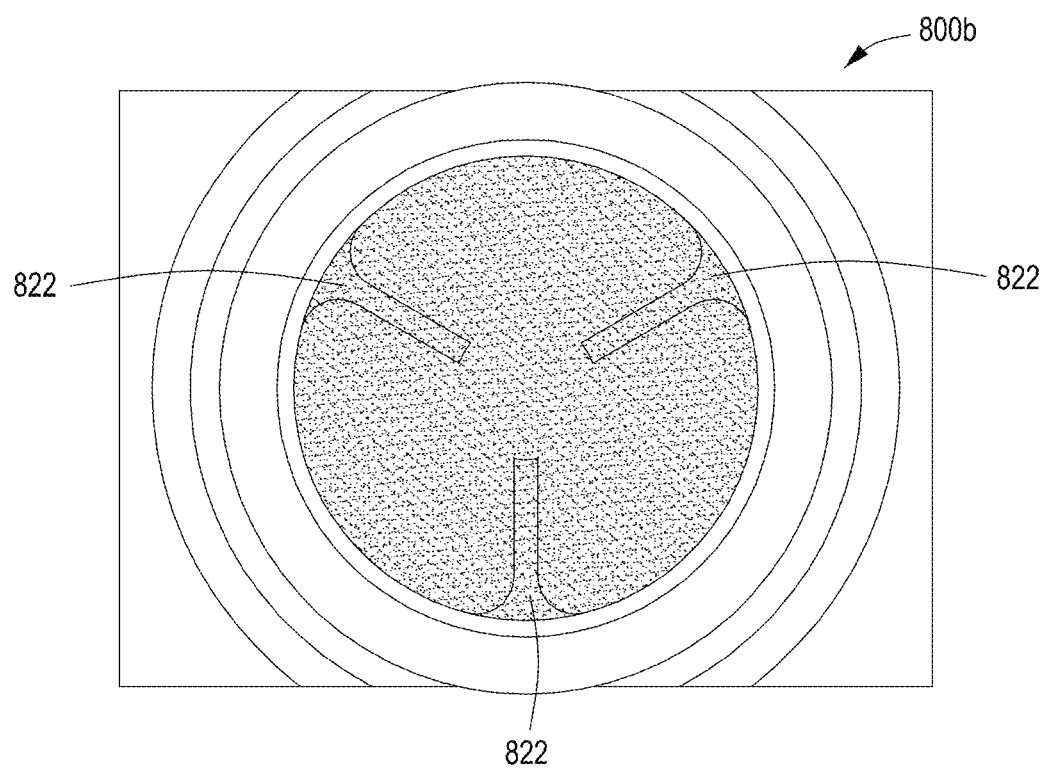
Figure 8C:
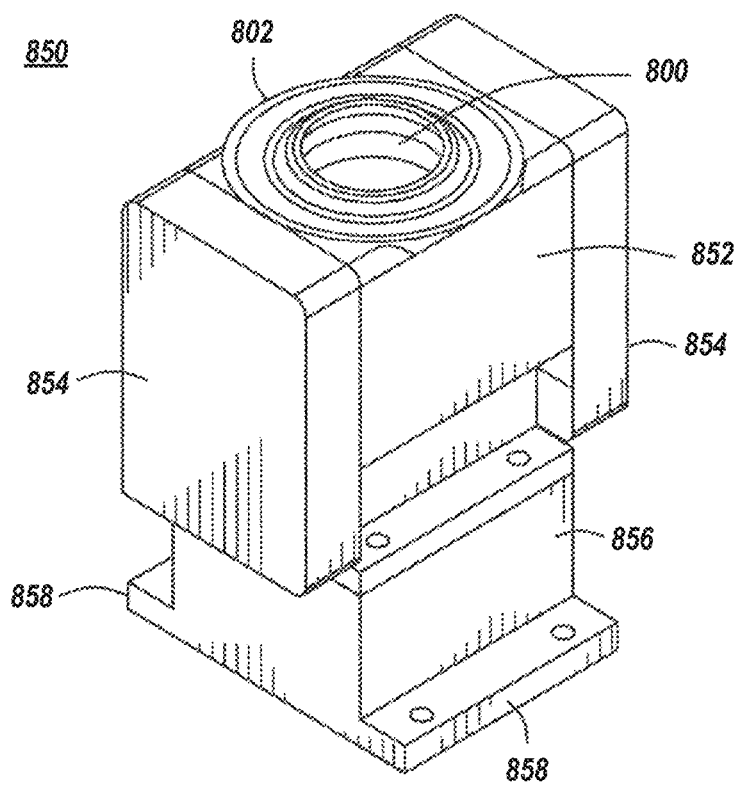
Figure 8D:
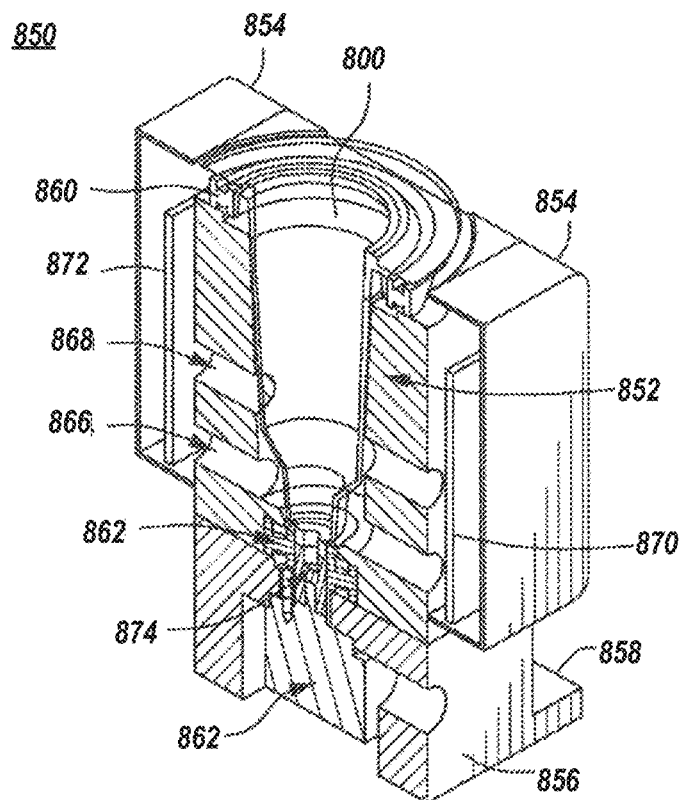

FIG. 8A shows one embodiment of a rotating growth vial 800 for use with a cell growth device, such as cell growth device 850 illustrated in FIGS. 8B-C. The rotating growth vial 800, in some implementations, is a transparent container having an open end 804 for receiving liquid media and cells, a central vial region 806 that defines the primary container for growing cells, a tapered-to-constricted region 818 defining at least one light path 808, 810, a closed end 816, and a drive engagement mechanism 812. The rotating growth vial 800 may have a central longitudinal axis 820 around which the vial 800 rotates, and the light paths 808, 810 may be generally perpendicular to the longitudinal axis of the vial. In some examples, first light path 810 may be positioned in the lower constricted portion of the tapered-to-constricted region 818. The drive engagement mechanism 812, in some implementations, engages with a drive mechanism (e.g., actuator, motor (not shown)) to rotate the vial 800. The actuator may include a drive shaft 874 for a drive motor 864 (FIG. 8D).

In some embodiments, the rotating growth vial 800 includes a second light path 808, for example, in the upper tapered region of the tapered-to-constricted region 818. In some examples, the walls defining the upper tapered region of the tapered-to-constricted region 818 for the second light path 808 may be disposed at a wider angle relative to the longitudinal axis 820 than the walls defining the lower constricted portion of the tapered-to-constricted region 810 for the first light path 810. Both light paths 808, 810, for example, may be positioned in a region of the rotating growth vial 800 that is constantly filled with the cell culture (cells+growth media), and is not affected by the rotational speed of the growth vial 800. As illustrated, the second light path 808 is shorter than the first light path 810 allowing for sensitive measurement of optical density (OD) values when the OD values of the cell culture in the vial are at a high level (e.g., later in the cell growth process), whereas the first light path 810 allows for sensitive measurement of OD values when the OD values of the cell culture in the vial are at a lower level (e.g., earlier in the cell growth process).

The rotating growth vial 800 may be reusable, or preferably, the rotating growth vial is consumable. In some embodiments, the rotating growth vial 800 is consumable and can be presented to the user pre-filled with growth medium, where the vial 800 is sealed at the open end 804 with a foil seal. A medium-filled rotating growth vial packaged in such a manner may be part of a kit for use with a stand-alone cell growth device or with a cell growth module that is part of an automated multi-module cell processing system. To introduce cells into the vial, a user need only pipette up a desired volume of cells and use the pipette tip to punch through the foil seal of the vial 800. Alternatively, of course, an automated instrument may transfer cells from, e.g., a reagent cartridge, to the growth vial. The growth medium may be provided in the growth vial or may also be transferred from a reagent cartridge to the growth vial before the addition of cells. Open end 804 may include an extended lip 802 to overlap and engage with the cell growth device 850 (FIGS. 8B-C). In automated instruments, the rotating growth vial 800 may be tagged with a barcode or other identifying means that can be read by a scanner or camera that is part of the processing system 1310 as illustrated in FIG. 13.

In some implementations, the volume of the rotating growth vial 800 and the volume of the cell culture (including growth medium) may vary greatly, but the volume of the rotating growth vial 800 should be large enough for the cell culture in the growth vial 800 to get proper aeration while the vial 800 is rotating. In practice, the volume of the rotating growth vial 800 may range from 1-250 ml, 2-100 ml, from 5-80 ml, 10-50 ml, or from 12-35 ml. Likewise, the volume of the cell culture (cells+growth media) should be appropriate to allow proper aeration in the rotating growth vial 800. Thus, the volume of the cell culture should be approximately 10-85% of the volume of the growth vial 800, or 15-80% of the volume of the growth vial, or 20-70%, 30-60%, or 40-50% of the volume of the growth vial. In one example, for a 35 ml growth vial 800, the volume of the cell culture would be from about 4 ml to about 27 ml.

The rotating growth vial 800, in some embodiments, is fabricated from a bio-compatible transparent material- or at least the portion of the vial 800 including the light path(s) is transparent. Additionally, material from which the rotating growth vial 800 is fabricated should be able to be cooled to about 0° C. or lower and heated to about 75° C. or higher, such as about 2° C. or to about 70° C., about 4° C. or to about 60° C., or about 4° C. or to about 55° C. to accommodate both temperature-based cell assays and long-term storage at low temperatures. Further, the material that is used to fabricate the vial is preferably able to withstand temperatures up to 55° C. without deformation while spinning. Suitable materials include glass, polyvinyl chloride, polyethylene, polyamide, polyethylene, polypropylene, polycarbonate, poly(methyl methacrylate) (PMMA), polysulfone, polyurethane, and co-polymers of these and other polymers. Preferred materials include polypropylene, polycarbonate, or polystyrene. In some embodiments, the rotating growth vial 800 is inexpensively fabricated by, e.g., injection molding or extrusion.

FIG. 8B illustrates a top view of a rotating growth vial 800*b*, which is an alternative implementation of the rotating growth vial 800. In some examples, the vial 800*b* may include one or more paddles 822 affixed to an inner surface that protrude toward the center of the vial 800*b*. The vial 800*b* shown in FIG. 8B includes three paddles 822 that are substantially equally spaced around the periphery of the vial 800*b*, but in other examples, the vial 800*b* may include two, four, or more paddles 822. The paddles, in some implementations, provide high mixing and aeration within the vial 800*b* rotating within a cell growth device, which facilitates microbial growth.

FIGS. 8C-D illustrate views of an example cell growth device 850 that receives the rotating growth vial 800. In some embodiments, the cell growth device 850 rotates to heat or cool the cells or cell growth within the vial 800 to a predetermined temperature range. In some implementations, the rotating growth vial 800 can be positioned inside a main housing 852 with the extended lip 802 of the vial 800 extending past an upper surface of the main housing 852. In some aspects, the extended lip 802 provides a grasping surface for a user inserting or withdrawing the vial 800 from the main housing 852 of the device 850. Additionally, when fully inserted into the main housing 852, a lower surface of the extended lip 802 abuts an upper surface of the main housing 852. In some examples, the main housing 852 of the cell growth device 850 is sized such that outer surfaces of the rotating growth vial 800 abut inner surfaces of the main housing 852 thereby securing the vial 800 within the main housing 852. In some implementations, the cell growth device 850 can include end housings 854 disposed on each side of the main housing 854 and a lower housing 856 disposed at a lower end of the main housing 852. In some examples, the lower housing 856 may include flanges 858 that can be used to attach the cell growth device 850 to a temperature control (e.g, heating/cooling) mechanism or other structure such as a chassis of an automated cell processing system.

As shown in FIG. 8D, the cell growth device 850, in some implementations, can include an upper bearing 860 and lower bearing 862 positioned in main housing 852 that support the vertical load of a rotating growth vial 800 that has been inserted into the main housing 852. In some examples, the cell growth device 850 may also include a primary optical port 866 and a secondary optical port 868 that are aligned with the first light path 810 and second light path 808 of the vial 800 when inserted into the main housing 852. In some examples, the primary and secondary optical ports 866, 868 are gaps, openings, or portions of the main housing constructed from transparent materials that allow light to pass through the vial 800 to perform cell growth OD measurements. In addition to the optical ports 866, 868, the cell growth device 850 may include an emission board 870 that provides one or more illumination sources for the light path(s), and detector board 872 to detect the light after the light travels through the cell culture liquid in the rotating growth vial 800. In one example, the illumination sources disposed on the emission board 870 may include light emission diodes (LEDs) or photodiodes that provide illumination at one or more target wavelengths commensurate with the growth media typically used in cell culture (whether, e.g., mammalian cells, bacterial cells, animal cells, yeast cells).

In some implementations, the emission board 870 and/or detector board 872 are communicatively coupled through a wired or wireless connection to a processing system (e.g., processing system 126, 1220, 1310) that controls the wavelength of light output by the emission board 870 and receives and processes the illumination sensed at the detector board 872. The remotely controllable emission board 870 and detector board 872, in some aspects, provide for conducting automated OD measurements during the course of cell growth. For example, the processing system 126, 1220 may control the periodicity with which OD measurements are performed, which may be at predetermined intervals or in response to a user request Further, the processing system 126, 1220 can use the sensor data received from the detector board 872 to perform real-time OD measurements and adjust cell growth conditions (e.g., temperature, speed/direction of rotation).

In some embodiments, the lower housing 856 may contain drive motor 864 that generates rotational motion that causes the rotating growth vial 800 to spin within the cell growth device 850. In some implementations, the motor 864 may include a drive shaft 874 that engages a lower end of the rotating growth vial 800. The motor 864 that generates rotational motion for the rotating growth vial 800, in some embodiments, is a brushless DC type drive motor with built-in drive controls that can be configured to maintain a constant revolution per minute (RPM) between 0 and about 3000 RPM. Alternatively, other motor types such as a stepper, servo, or brushed DC motors can be used. Optionally, the motor 864 may also have direction control to allow reversing of the rotational direction, and a tachometer to sense and report actual RPM. In other examples, the motor 864 can generate oscillating motion by reversing the direction of rotation at a predetermined frequency. In one example, the vial 800 is rotated in each direction for one second at a speed of 350 RPM. The motor 864, in some implementations, is communicatively coupled through a wired or wireless communication network to a processing system (e.g., processing system 126, 1220) that is configured to control the operation of the motor 864, which can include executing protocols programmed into the processor and/or provided by user input, for example as described in relation to module controller 1330 of FIG. 13. For example, and the motor 864 can be configured to vary the speed and/or rotational direction of the vial 800 to cause axial precession of the cell culture thereby enhancing mixing in order to prevent cell aggregation and increase aeration. In some examples, the speed or direction of rotation of the motor 864 may be varied based on optical density sensor data received from the detector board 872.

In some embodiments, main housing 852, end housings 854 and lower housing 856 of the cell growth device 856 may be fabricated from a robust material including aluminum, stainless steel, and other thermally conductive materials, including plastics. These structures or portions thereof can be created through various techniques, e.g., metal fabrication, injection molding, creation of structural layers that are fused, etc. While in some examples the rotating growth vial 800 is reusable, in other embodiments, the vial 800 is preferably is consumable. The other components of the cell growth device 850, in some aspects, are preferably reusable and can function as a stand-alone benchtop device or as a module in an automated multi-module cell processing system.

In some implementations, the processing system that is communicatively coupled to the cell growth module may be programmed with information to be used as a "blank" or control for the growing cell culture. A "blank" or control, in some examples, is a vessel containing cell growth medium only, which yields 100% transmittance and 0 OD, while the cell samples deflect light rays and will have a lower percentage transmittance and higher OD. As the cells grow in the media and become denser, transmittance decreases and OD increases. The processor of the cell growth module, in some implementations, may be programmed to use wavelength values for blanks commensurate with the growth media typically used in cell culture (whether, e.g., mammalian cells, bacterial cells, animal cells, yeast cells). Alternatively, a second spectrophotometer and vessel may be included in the cell growth module, where the second spectrophotometer is used to read a blank at designated intervals.

Figure 8E:
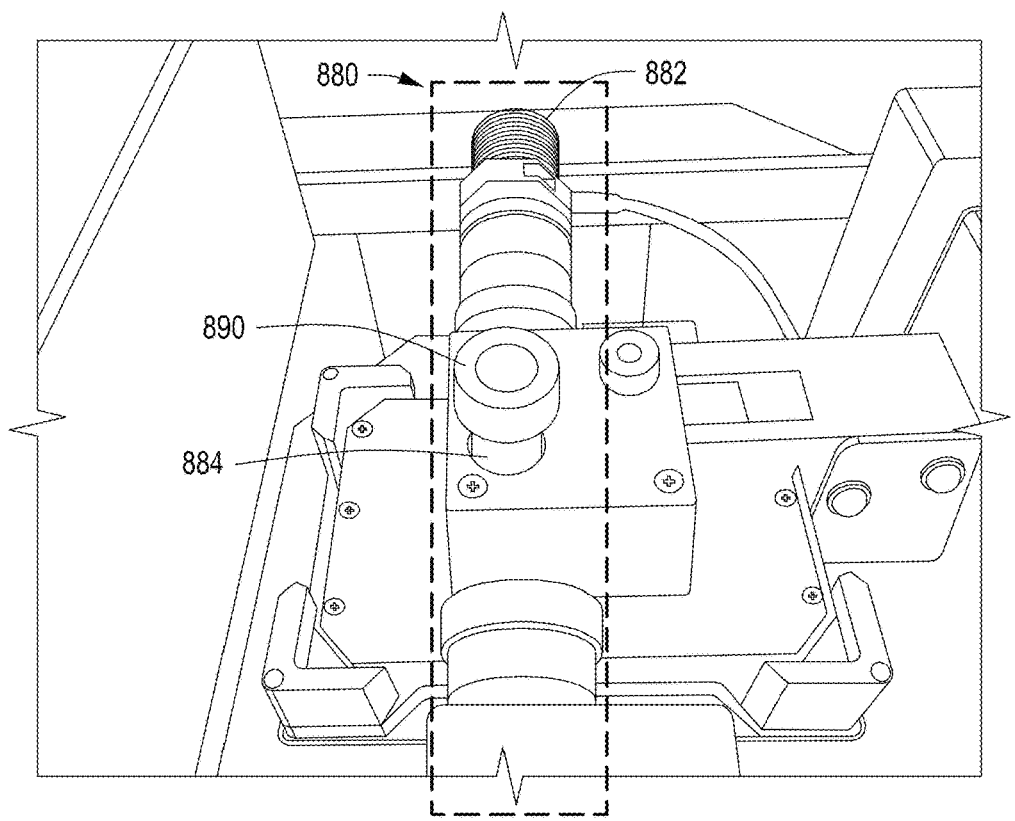
Figure 8F:
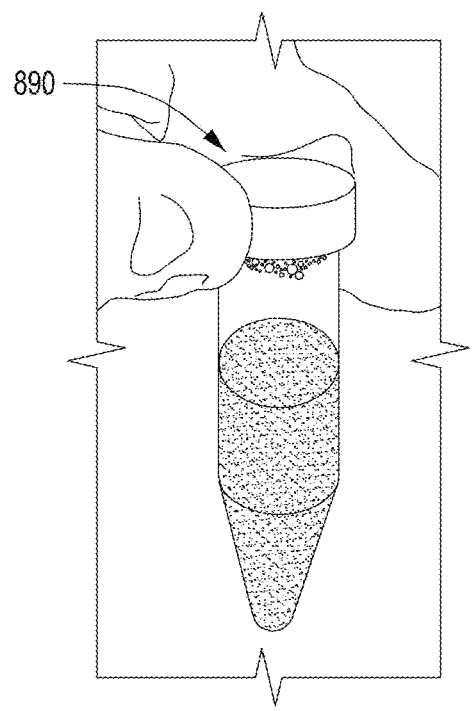

FIG. 8E illustrates another type of cell growth device 880 that uses shaking, rather than rotation, to control temperature and promote mixing and aeration within a cell growth vial 890 (FIG. 8F). The cell growth device 880, in some examples, is smaller in size than conventional bench top shakers for integration into automated multi-module cell processing systems. In some implementations, the cell growth device 880 includes a housing 884 that receives cell growth vial 890. The cell growth device 880 can, in some examples, include a motor assembly positioned beneath the vial 890 that generates an orbital motion of the vial 890 based on the speed of the motor. In one example, the vial 890 travels in an orbit in a horizontal plane at 600 to 900 RPM, such as at 750 RPM, which is significantly faster than larger bench top shakers that orbit at around 250 RPM. In some aspects, the shaking motion is generated in at least one horizontal plane. In some examples, the cell growth vial 890 used with the shaking cell growth device 880 is a conical bottom tube substantially similar in shape to a flask that is used in a conventional bench shaker. Similar to the rotating cell growth device 850, the cell growth device 880 may include illumination board 870 and detector board 872 for taking automated OD measurements over the course of cell growth. In some examples, a light source 882 may be coupled to the cell growth device 880 that generates the illumination that is measured by a detector board, which in some examples, is located beneath the vial 890 or on an opposite side of the vial 890 from the light source 882.

To reduce background of cells that have not received a genome edit, the growth module may also allow a selection process to enrich for the edited cells. For example, the introduced nucleic acid can include a gene, which confers antibiotic resistance or another selectable marker. Alternating the introduction of selectable markers for sequential rounds of editing can also eliminate the background of unedited cells and allow multiple cycles of the automated multi-module cell editing instrument to select for cells having sequential genome edits.

Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background.

Cell Wash and/or Concentration Module

The cell wash and/or concentration module can utilize any method for exchanging the liquids in the cell environment, and may concentrate the cells or allow them to remain in essentially the same or greater volume of liquid as used in the nucleic acid assembly module. Further, in some aspects, the processes performed in the cell wash module also render the cells electrocompetent, by, e.g., use of glycerol in the wash.

Numerous different methods can be used to wash the cells, including density gradient purification, dialysis, ion exchange columns, filtration, centrifugation, dilution, and the use of beads for purification.

In some aspects, the cell wash and/or concentration module utilizes a centrifugation device. In other aspects, the cell wash and/or concentration module utilizes a filtration module. In yet other aspects, beads are coupled to moieties that bind to the cell surface. These moieties include but are not limited to antibodies, lectins, wheat germ agglutinin, mutated lysozymes, and ligands.

In other aspects, the cells are engineered to be magnetized, allowing magnets to pellet the cells after wash steps. Mechanism of cell magnetization can include but not limited to ferritin protein expression.

The cell wash and/or concentration module, in some implementations, is a centrifuge assembly module. Turning to FIGS. 3A-C, in some implementations, a centrifuge assembly module 300 includes a top door 302 designed for actuation by a robotic handling system (not shown) to deliver nucleic acid assembly materials (e.g., oligos, vector backbone, enzymes, etc.) to one or more vials 304a, b situated in vial buckets 306a, b connected to a rotor 308. In some embodiments, the robotic handling system delivers the vials 304a,b to the centrifuge assembly module 300. In other embodiments, a user disposes the vials 304a, b within the vial buckets 306a, b. The vial buckets 306a, b in some embodiments, are connected to the rotor 308 via a hinged connection such that the via buckets 306a,b may swing outwards during rotation. In other embodiments, the position of the buckets 306a,b is fixed.

The centrifuge assembly module 300, in some embodiments, is climatically controlled. For example, the internal temperature may be managed by cooling coils 310 and insulation 312. Coolant supply and return lines 314 may pump coolant to the cooling coils 310, thereby cooling a chamber 316 of the centrifuge assemble module 300. In some examples, the centrifuge assembly module 300 may be designed to cool the chamber 316 to between 0° and 10° C., between 2° and 8° C., and most preferably to about 4° C. Further, condensation control may be provided to limit humidity within the chamber 316. Climatic control, in some embodiments, is set through a processing system of the automated multi-module cell processing instrument. For example, the processing system may direct signals to interfaces of circuitry 320.

In some embodiments, a motor 318 rotationally drives the rotor 308. Acceleration and deceleration of the motor 318 and thus the rotor 308 may be controlled by a processing system of the automated multi-module cell processing instrument. As illustrated, a motion sensor 322 (e.g., accelerometer or gyroscope) is positioned at a base of the motor 318 to monitor rotational parameters. Alternatively, a motion sensor (not illustrated) such as an accelerometer or gyroscope may be placed within the chamber 316 to monitor rotational parameters. The processing system, for example, may monitor signals from the motion sensor and analyze conditions to enact a safety shutdown if rotation is outside parameters. In an illustrative embodiment, the rotor arm may be designed to rotate at up to 10000 revolutions per minute (RPM), up to 8000 RPM, or up to about 6500 RPM. The processing system may modify the rotational speed based upon materials supplied to the centrifuge assembly module 300.

Figure 7A:
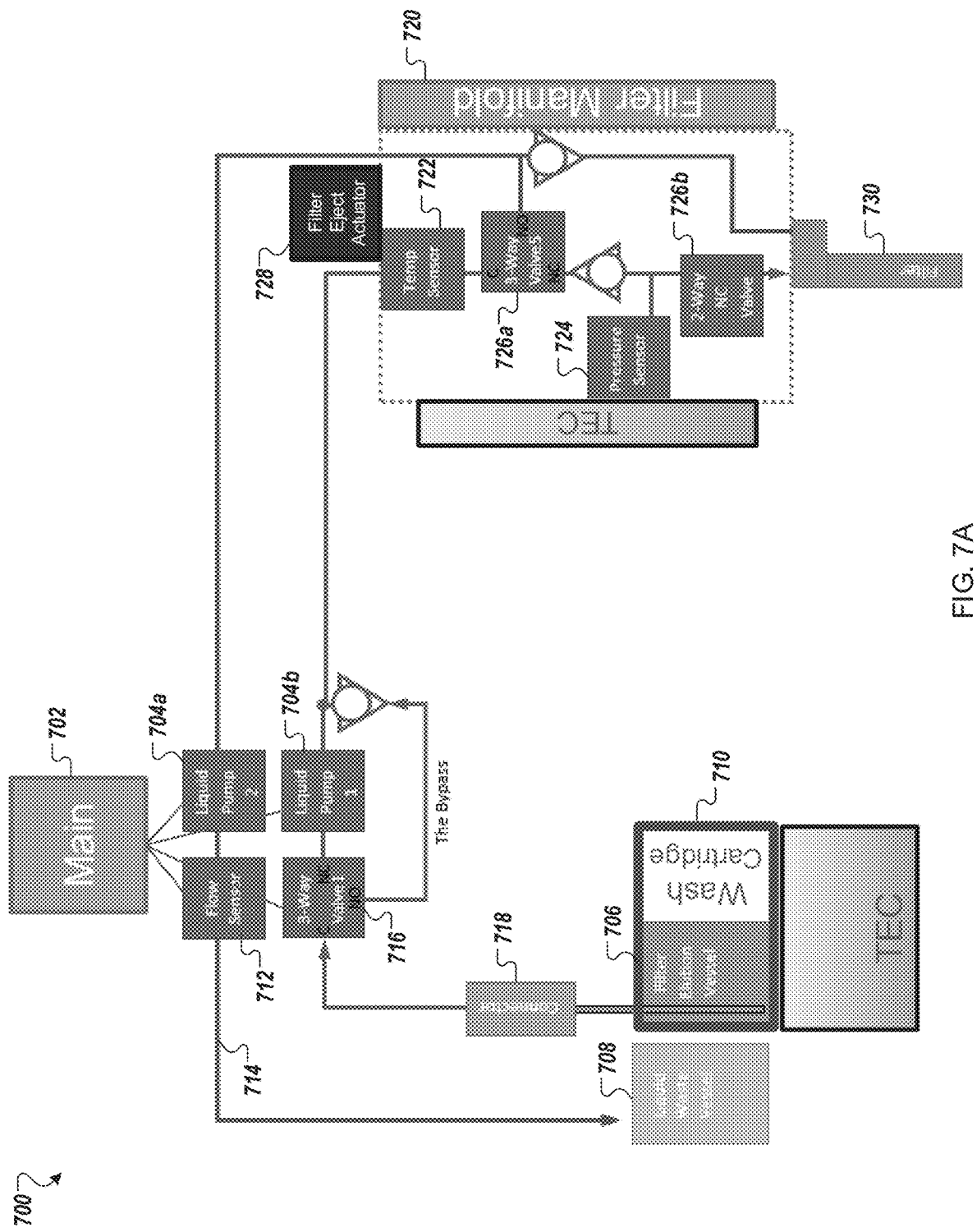
FIGS. 7A-7C provide a functional block diagram and two perspective views of an example filtration module for use in an automated multi-module cell processing instrument.

The cell wash and/or concentration module, in some implementations, is a filtration module. Turning to FIG. 7A, a block diagram illustrates example functional units of a filtration module 700. In some implementations, a main control 702 of the filtration module 700 includes a first liquid pump 704a to intake wash fluid 706 and a second liquid pump 704b to remove liquid waste to a liquid waste unit 708 (e.g., such as the liquid waste unit 114 of FIG. 1A or liquid waste unit 1228 of FIGS. 12A and 12B). A flow sensor 712 may be disposed on a connector 714 to the liquid waste unit 708 to monitor release of liquid waste from the filtration module. A valve 716 (a three-way valve as illustrated) may be disposed on a connector 718 to the wash fluid 716 to selectively connect the wash fluid 716 and the filtration module 700.

The filtration module 700, in some implementations, includes a filter manifold 720 for filtering and concentrating a cell sample. The filter manifold 720 may include one or more temperature sensor(s) 722 and pressure sensor (s) 724 to monitor flow and temperature of the wash fluid and/or liquid waste. The sensors 722, 724, in some embodiments, are monitored and analyzed by a processing system of the automated multi-mode cell processing system, such as the processing system 1310 of FIG. 13. The filter manifold 720 may include one or more valves 726 for directing flow of the wash fluid and/or liquid waste. The processing system of the automated multi-mode cell processing instrument, for example, may actuate the valves according to a set of instructions for directing filtration by the filtration module 700.

The filtration module 700 includes at least one filter 730. Examples of filters suitable for use in the filtration module 700 include membrane filters, ceramic filters and metal filters. The filter may be used in any shape; the filter may for example be cylindrical or essentially flat. The filter selected for a given operation or a given workflow, in some embodiments, depends upon the type of workflow (e.g., bacterial, yeast, viral, etc.) or the volumes of materials being processed. For example, while flat filters are relatively low cost and commonly used, filters with a greater surface area, such as cylindrical filters, may accept higher flow rates. In another example, hollow filters may demonstrate lower recovery rates when processing small volumes of sample (e.g., less than about 10 ml). For example, for use with bacteria, it may be preferable that the filter used is a membrane filter, particularly a hollow fiber filter. With the term "hollow fiber" is meant a tubular membrane. The internal diameter of the tube, in some examples, is at least 0.1 mm, more preferably at least 0.5 mm, most preferably at least 0.75 mm and preferably the internal diameter of the tube is at most 10 mm, more preferably at most 6 mm, most preferably at most 1 mm. Filter modules having hollow fibers are commercially available from various companies, including G. E. Life Sciences (Marlborough, Mass.) and InnovaPrep (Drexel, Mo.) (see, e.g., US20110061474A1 to Page et al., entitled "Liquid to Liquid Biological Particle Concentrator with Disposable Fluid Path").

In some implementations, the filtration module 700 includes a filter ejection means 728 (e.g., actuator) to eject a filter 730 post use. For example, a user or the robotic handling system may push the filter 730 into position for use such that the filter is retained by the filter manifold 720 during filtration. After filtration, to remove the used filter 730, the filter ejection actuator 728 may eject the filter 730, releasing the filter 730 such that the user or the robotic handling system may remove the used filter 730 from the filtration module 700. The used filter 730, in some examples, may be disposed within the solid waste unit 112 of FIGS. 1A-1B, solid waste unit 1218 of FIGS. 12A and 12B, or returned to a filter cartridge 740, as illustrated in FIG. 7D.

Figure 7C:
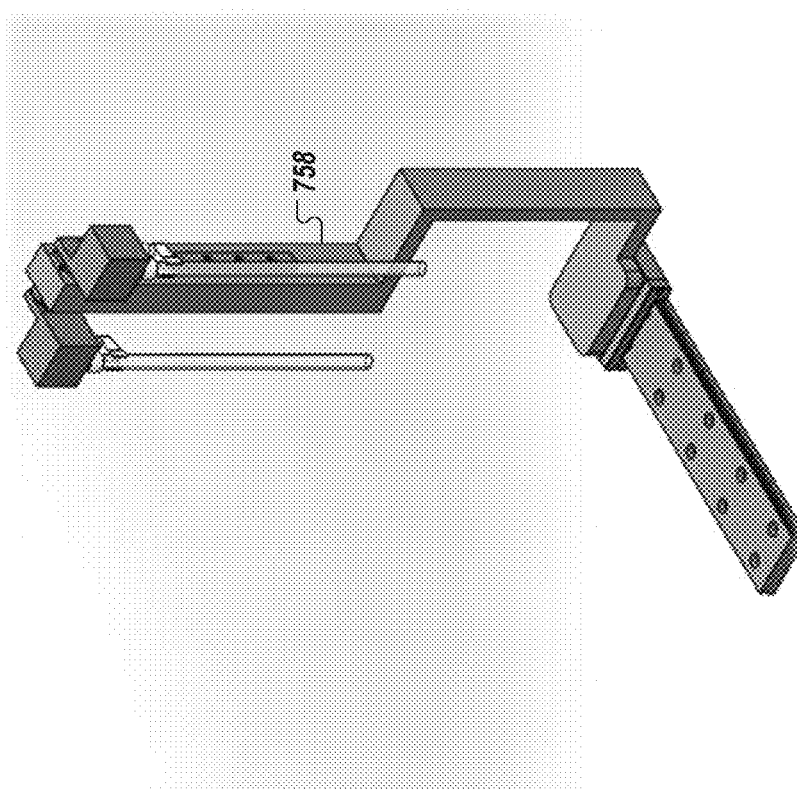
Figure 7B:
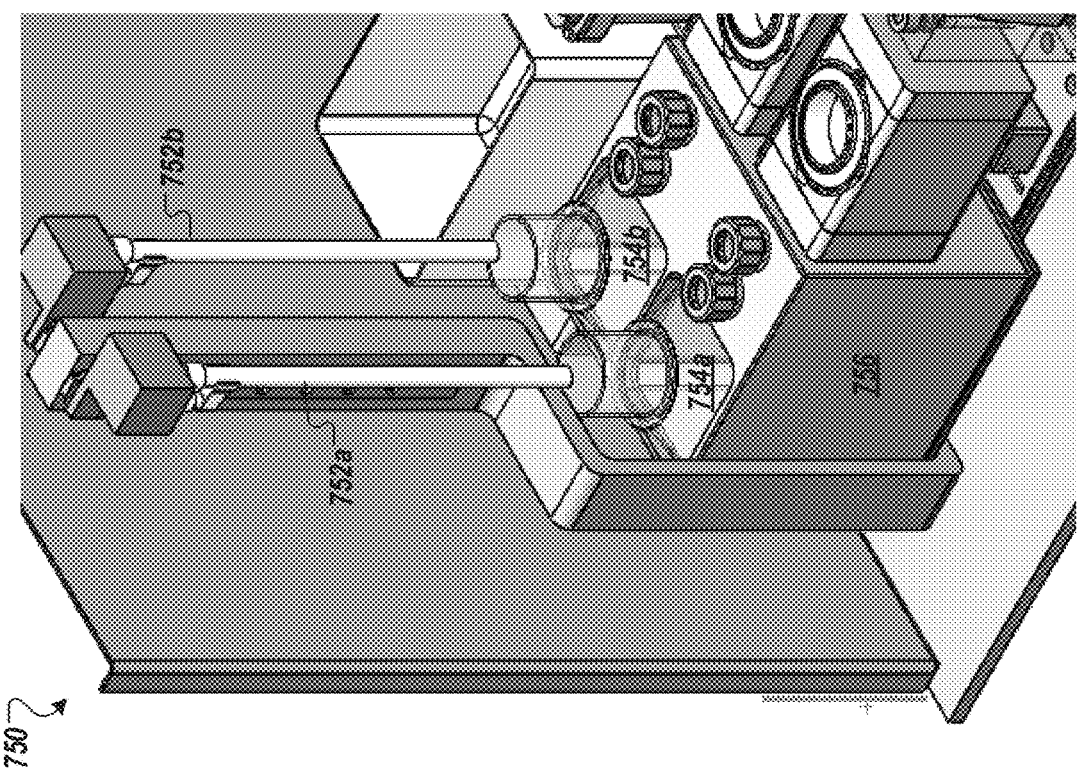
Figure 7D:
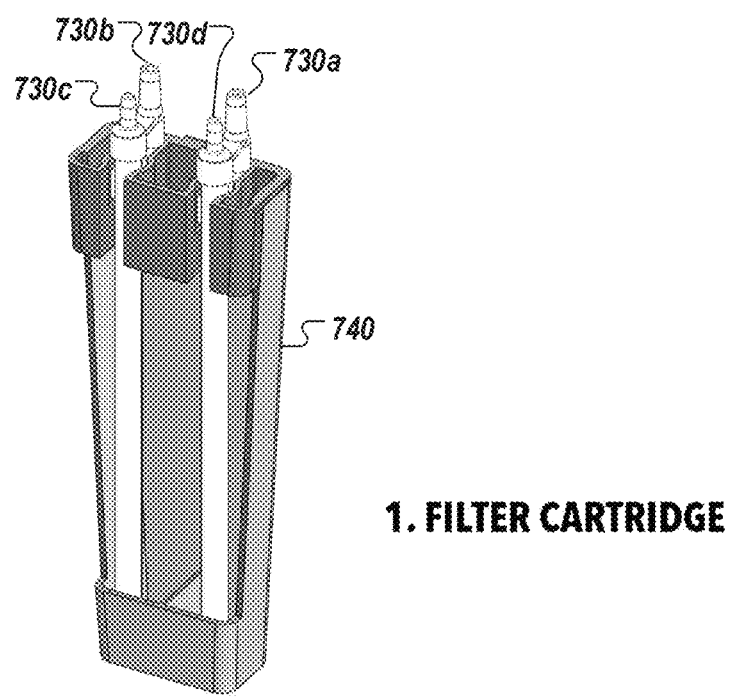
FIG. 7D is a perspective views of an example filter cartridge for use in an automated multi-module cell processing instrument.
Figure 12A:
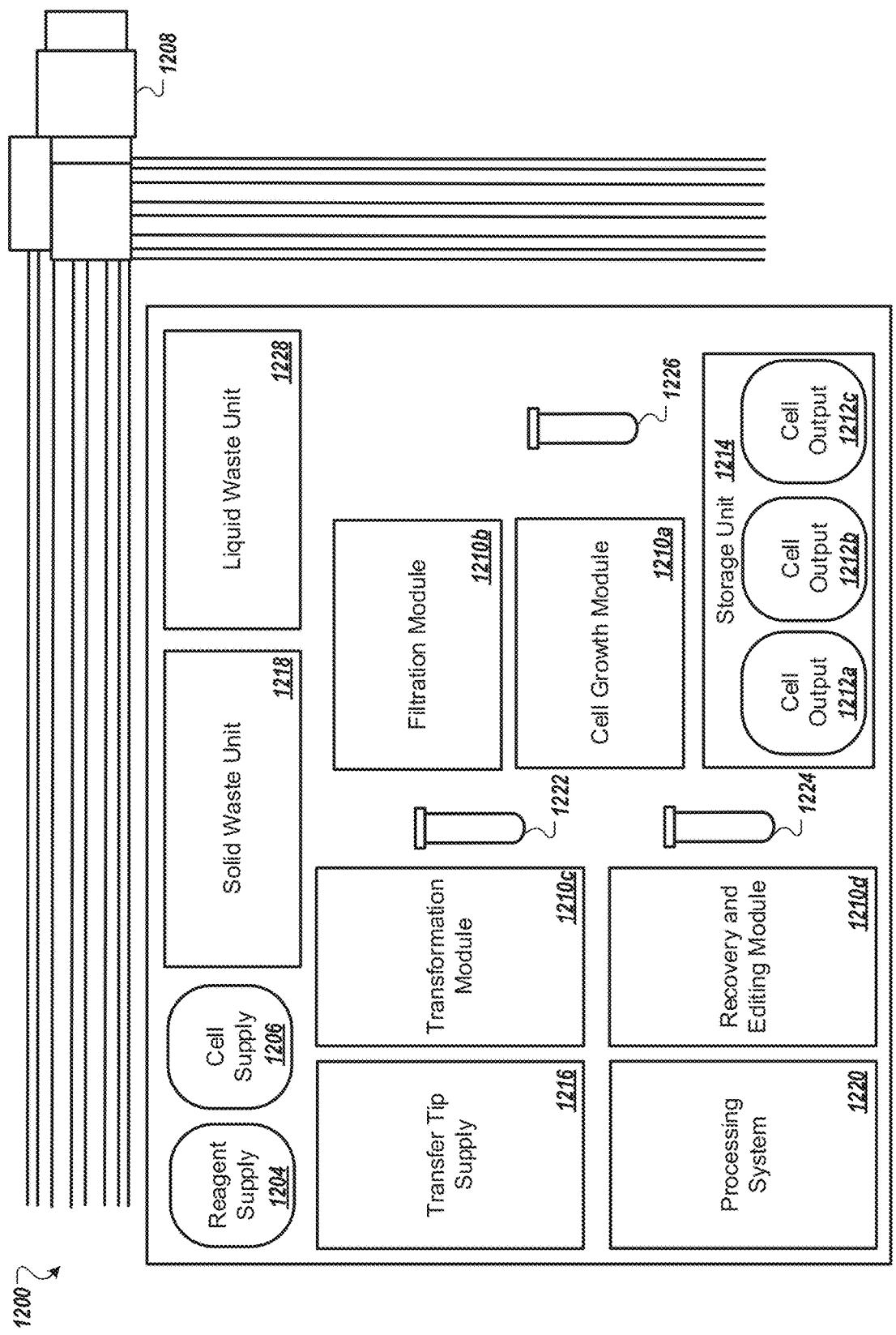
FIG. 12A is a functional block system diagram of another example embodiment of an automated multi-module cell processing instrument for the multiplexed genome editing of multiple cells.
Figure 12B:
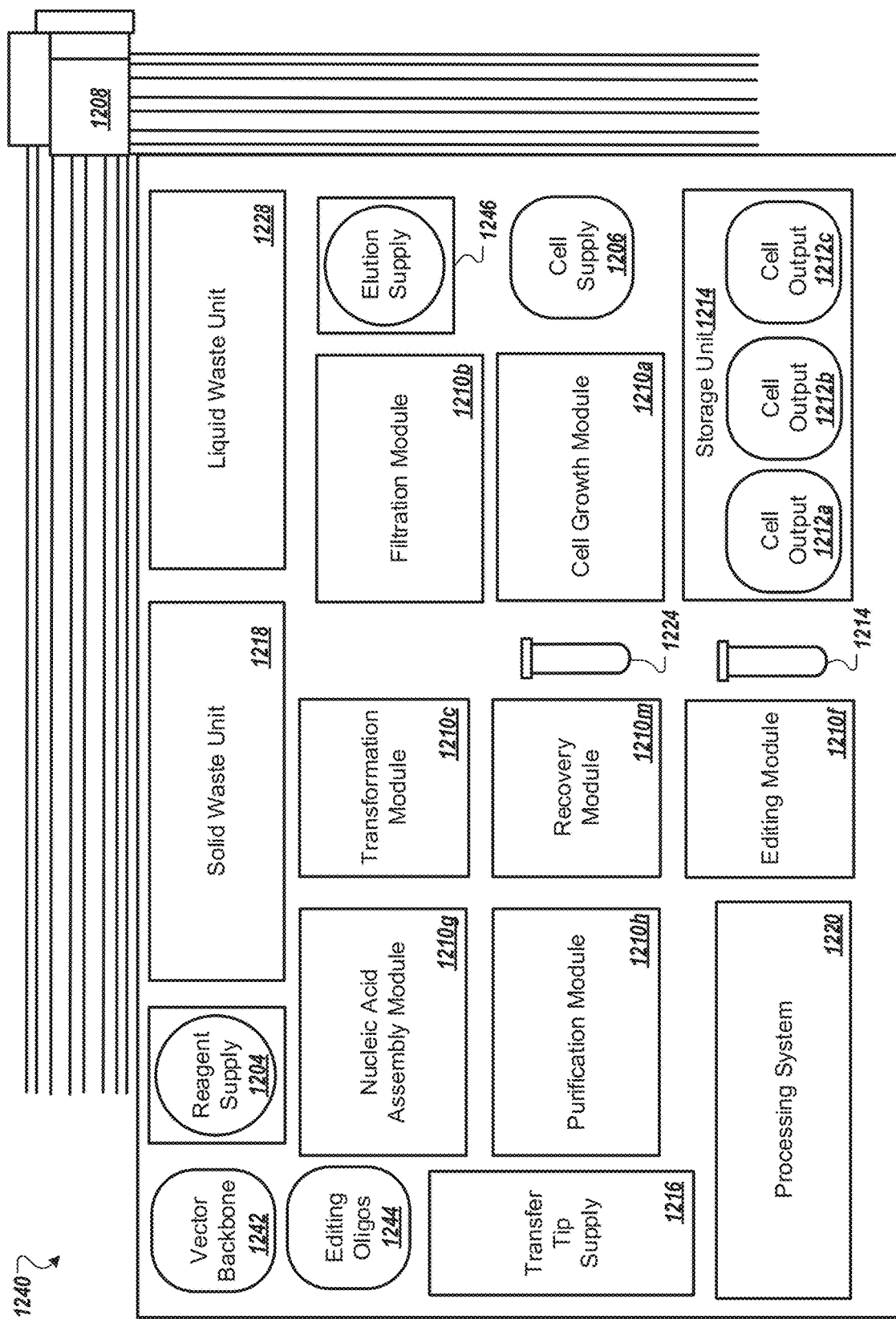
FIG. 12B is a functional block system diagram of yet another example embodiment of an automated multi-module cell processing instrument for the recursive, multiplexed genome editing of multiple cells.

Turning to FIG. 7D, in some implementations, filters 730 provided in the filter cartridge 740 disposed within the chassis of the automated multi-module cell processing instrument are transported to the filtration module 700 by a robotic handling system (e.g., the robotic handling system 108 described in relation to FIGS. 1A and 1B, or robotic handling system 1218 of FIGS. 12A and 12B) and positioned within the filtration module 700 prior to use.

The filtration module 700, in some implementations, requires periodic cleaning. For example, the processing system may alert a user when cleaning is required through the user interface of the automated multi-module cell processing instrument and/or through a wireless messaging means (e.g., text message, email, and/or personal computing device application). A decontamination filter, for example, may be loaded into the filtration module 700 and the filtration module 700 may be cleaned with a wash solution and/or alcohol mixture.

In some implementations, the filtration module 700 is in fluid connection with a wash cartridge 710 (such as the wash cartridge 600 of FIG. 6A) containing the wash fluid 716 via the connector 718. For example, upon positioning by the user of the wash cartridge 710 within the chassis of the automated multi-module cell processing instrument, the connector 718 may mate with a bottom inlet of the wash cartridge 710, creating a liquid passage between the wash fluid 716 and the filtration module 700.

Turning to FIGS. 7B and 7C, in some implementations, a dual filter filtration module 750 includes dual filters 752, 754 disposed over dual wash reservoirs 754. In an example, each filter may be a hollow core fiber filter having 0.45 um pores and greater than 85 cm$^2$ area. The wash reservoirs 754, in some examples, may be 50 mL, 100 mL, or over 200 mL in volume. In some embodiments, the wash reservoirs 754 are disposed in a wash cartridge 756, such as the wash or reagent cartridge 600 of FIG. 6A.

The processing system of the automated multi-module cell processing instrument, in some implementations, controls actuation of the dual filters 752 in an X (horizontal) and Z (vertical) direction to position the filters 752a, 752b in the wash reservoirs 754. In a particular example, the dual filters 752 may be move in concert along the X axis but have independent Z axis range of motion.

As illustrated, the dual filters 752 of the filtration module 750 are connected to a slender arm body 758. In some embodiments, any pumps and valves of the filtration module 750 may be disposed remotely from the body 758 (e.g., within a floor of the chassis of the automated multi-module cell processing instrument). In this manner, the filtration module 750 may replace much bulkier conventional commercial filtration modules.

Further, in some embodiments, the filtration module 750 is in liquid communication with a waste purge system designed to release liquid waste into a liquid waste storage unit, such as the storage unit 708 of FIG. 7A or the liquid waste storage unit 114 of FIG. 1A or 1228 of FIGS. 12A and 12B.

Transformation Module

The transformation module may implement any cell transformation or transfection techniques routinely used by those of skill in the arts of transfection, transformation and microfluidics. Transformation can take place in microfuge tubes, test tubes, cuvettes, multi-well plates, microfibers, and flow instruments. Temperature and control of the transformation module can be controlled using a processing system such as the processing system 1310 of FIG. 13, with controls set by the user and/or through a script provided to the processing system.

Transformation is intended to include to a variety of art-recognized techniques for introducing an exogenous nucleic acid sequence (e.g., DNA) into a target cell, and the term "transformation" as used herein includes all transformation and transfection techniques. Such methods include, but are not limited to, electroporation, lipofection, optoporation, injection, microprecipitation, microinjection, liposomes, particle bombardment, sonoporation, laser-induced poration, bead transfection, calcium phosphate or calcium chloride co-precipitation, or DEAE-dextran-mediated transfection. Cells can also be prepared for vector uptake using, e.g., a sucrose or glycerol wash. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, Molecular Cloning: A Laboratory Manual, 4th, ed., Cold Spring Harbor Laboratory Press, Cold Spring Harbor, N.Y., 2014).

The medium or buffer used to suspend the cells and material (reagent) to be electroporated into the cells for the electroporation process may be a medium or buffer including, but not limited to, MEM, DMEM, IMDM, RPMI, Hanks', PBS or Ringer's solution, where the media may be provided in the reagent cartridge as part of a kit. For electroporation of most eukaryotic cells, the medium or buffer usually contains salts to maintain a proper osmotic pressure. The salts in the medium or buffer also render the medium conductive. For electroporation of very small prokaryotic cells such as bacteria, sometimes water or 10% glycerol is used as a low conductance medium to allow a very high electric field strength. In that case, the charged molecules to be delivered still render water-based medium more conductive than the lipid-based cell membranes and the medium may still be roughly considered as conductive particularly in comparison to cell membranes.

The compound to be electroporated into the cells of choice can be any compound known in the art to be useful for electroporation, such as nucleic acids, oligonucleotides, polynucleotides, DNA, RNA, peptides, proteins and small molecules like hormones, cytokines, chemokines, drugs, or drug precursors.

It is important to use voltage sufficient for achieving electroporation of material into the cells, but not too much voltage as too much power will decrease cell viability. For example, to electroporate a suspension of a human cell line, 200 volts is needed for a 0.2 ml sample in a 4 mm-gap cuvette with exponential discharge from a capacitor of about 1000 g. However, if the same 0.2 ml cell suspension is placed in a longer container with 2 cm electrode distance (5 times of cuvette gap distance), the voltage required would be 1000 volts, but a capacitor of only 40 μF (1/25 of 1000 g) is needed because the electric energy from a capacitor follows the equation of:

$$E = 0.5U^2C$$

where E is electric energy, U is voltage and C is capacitance. Therefore a high voltage pulse generator is actually easy to manufacture because it needs a much smaller capacitor to store a similar amount of energy. Similarly, it would not be difficult to generate other wave forms of higher voltages.

The electroporation devices of the disclosure can allow for a high rate of cell transformation in a relatively short amount of time. The rate of cell transformation is dependent on the cell type and the number of cells being transformed. For example, for *E. Coli*, the electroporation devices can provide a cell transformation rate of 1 to $10^{10}$ cells per second, $10^4$ to $10^7$ per second, $10^5$ to $10^8$ per second, or $10^6$ to $10^9$ per second. The electroporation devices also allow transformation of batches of cells ranging from 1 cell to $10^{10}$ cells in a single transformation procedure using the device.

The efficiency of the transformation using the electroporation devices of the disclosure can result in at least 10% of the cells being sufficiently porated to allow delivery of the biological molecule. Preferably, the efficiency of the transformation using the electroporation devices of the disclosure can result in at least 15%, 20%, 25%, 30%, 35%, 40%, 45%, 50%, 55%, 60%, 75%, 80%, 85%, 90%, 95% or greater of the cells being sufficiently porated to allow delivery of the biological molecule.

In some embodiments, the electroporation is performed in a cuvette, a well, a tube, a chamber, a flow cell, a channel, or a pipette tip. In other embodiments, the cuvette, well, tube, or chamber is filled and emptied from the bottom. In some embodiments, the cuvette contains a sipper connected to the bottom.

Figure 5A:
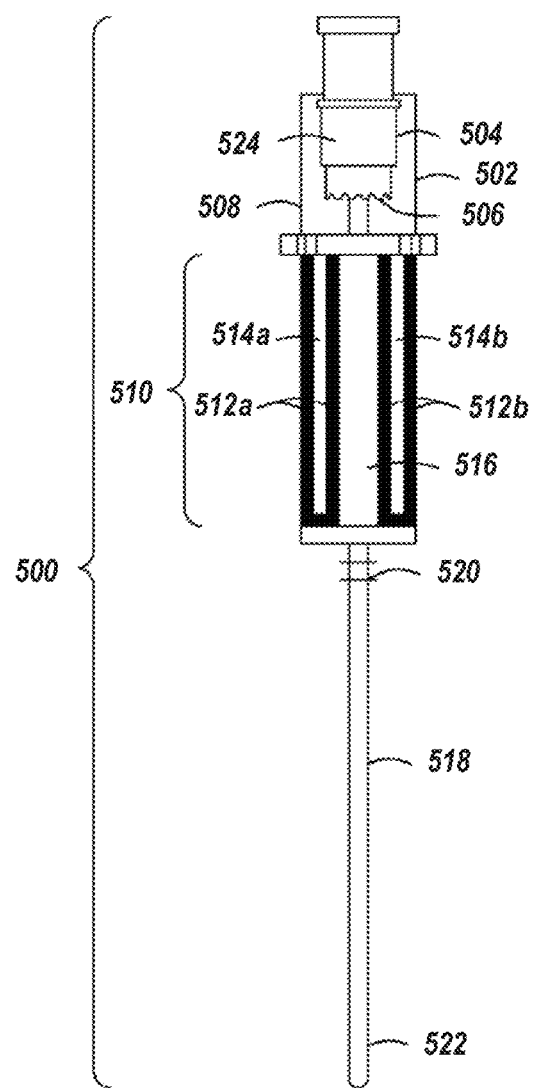
FIG. 5A depicts an example inline electroporation module for use in an automated multi-module cell processing instrument.

FIG. 5A depicts an example single-unit electroporation device 500 (electroporation module) including, from top to bottom, a housing 502 that encloses an engagement member 504 configured to engage with a pipette such as an automatic air displacement pipette (not shown), and a filter 506. In addition to the housing 502, there is an electroporation cuvette 510 portion of the electroporation device 500 including electrodes 512, and walls 514 of the electroporation chamber 516. The chamber, in some examples, may range between 0.01-100 mm in width, 1-5,000 mm in height, and 1-20,000 μl in volume; between 0.03-50 mm in width, 50-2,000 mm in height, and 500-10,000 μl in volume; or between 0.05-30 mm in width, 2-500 mm in height, and 25-4,500 μl in volume.

In some embodiments, a first reservoir 508 may be placed between the filter 506 and the electroporation chamber 516, the first reservoir being in fluid communication with electroporation chamber 516 and providing an empty repository for any cell sample that may be taken in past the electroporation chamber 516. The first reservoir 508, in some examples, may range between 0.1-150 mm in width, 0.1-250 mm in height, and 0.5-10,000 μl in volume; between 0.3-100 mm in width, 30-150 mm in height, and 20-4,000 μl in volume; or between 0.5-100 mm in width, 0.5-100 mm in height, and 5-2,000 μl in volume.

In some implementations, the electroporation device 500 may additionally include another reservoir 524 in fluid communication with the first reservoir 508 (through filter 506). The second reservoir 524 may be placed between the filter 506 and the engagement member 504 to protect the pipette from contamination by any liquids that may make it past the filter 506. The second reservoir 524, in some examples, may range between 0.1-250 mm in width, 0.2-1000 mm in height, and 0.1-2,500 μl in volume; between 0.1-150 mm in width, 50-400 mm in height, and 1-1,000 μl in volume; or between 0.2-100 mm in width, 0.5-200 mm in height, and 2-600 μl in volume.

In some embodiments, a sipper 518 is in fluid communication with and coupled to the electroporation chamber 516, the sipper 518 having an end proximal 520 to the electroporation chamber 516 and an end distal 522 from the electroporation chamber 516. The distal end 522 of the sipper 518 may allow for uptake and dispensing of the cell sample from the electroporation device 500. The sipper 518, in some embodiments, is part of a robotic manipulation system. The sipper 518, in some examples, may be made from plastics such as polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers, glass (such as a glass capillary), and metal tubing such as aluminum, stainless steel, or copper. Exemplary materials include crystal styrene and cyclic olephin co-polymers. PEEK is a preferred plastic given it is low in price and easily fabricated. The sipper 518, in some examples, may range between 0.02-2,000 mm in width, 0.25-2,000 mm in height, and 1-2,000 μl in volume; between 0.02-1,250 mm in width, 250-1,500 mm in height, and 1.5-1,500 μl in volume; or between 0.02-10 mm in width, 4.0-1,000 mm in height, and 2.5-1,000 μl in volume.

The housing 502 and engagement member 504 of the electroporation device 500, in some examples, can be made from silicone, resin, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Similarly, the walls 512 of the electroporation chamber, in some examples, may be made of silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Exemplary materials include crystal styrene and cyclic olephin co-polymers. These structures or portions thereof can be created through various techniques, e.g., injection molding, creation of structural layers that are fused, etc. Polycarbonate and cyclic olephin polymers are preferred materials.

The electroporation chamber 516, in some embodiments, is generally cylindrical in shape. In other embodiments, the electroporation chamber 516 may be rectangular, conical, or square.

The filter 506 can be fashioned, in some examples, from porous plastics, hydrophobic polyethylene, cotton, or glass fibers. Preferably, the filter 506 is composed of a low-cost material such as porous plastics. The filter may range between 0.2-500 mm in width, 0.2-500 mm in height, and 1-3,000 μl in volume; between 0.3-250 mm in width, 20-200 mm in height, and 50-2,500 μl in volume; or between 0.5-150 mm in width, 0.2-80 mm in height, and 10-2,000 μl in volume.

The engagement member 504 is configured to have a dimension that is compatible with the liquid handling device used in the electroporation instrument.

The components of the electroporation devices may be manufactured separately and then assembled, or certain components of the electroporation devices may be manufactured or molded as a single entity, with other components added after molding. For example, the sipper, electroporation walls, and housing may be manufactured or molded as a single entity, with the electrodes, filter, engagement member later added to the single entity to form the electroporation module. Similarly, the electroporation walls and housing may be manufactured as a single entity, with the sipper, electrodes, filter, engagement member added to the electroporation module after molding. Other combinations of integrated and non-integrated components are possible.

The electrodes 512 can be formed from a metal, such as copper, titanium, aluminum, brass, silver, rhodium, gold or platinum, or graphite, capable of withstanding application of an electric field. For example, an applied electric field can destroy electrodes made from of metals like aluminum. If a multiple use electroporation device is desired, the electrode plates can be coated with metals resistant to electrochemical corrosion. Conductive coatings like noble metals, e.g., gold, can be used to protect the electrode plates. In a particular example, the electroporation cuvette may include a first metal electrode and a second metal electrode made from titanium covered with a layer of gold. Conversely, if the electroporation device 500 is designed for single use (e.g., disposable), less expensive metals such as aluminum may be used.

In one embodiment, the distance between the electrodes may be between 0.3 mm and 10 mm. In another embodiment, the distance between the electrodes may be between 1 mm and 20 mm, or 1 mm to 10 mm, or 2 mm to 5 mm. The inner diameter of the electroporation chamber may be between 0.1 mm and 10 mm. To avoid different field intensities between the electrodes, the electrodes should by arranged in parallel with a constant distance to each other over the whole surface of the electrodes. Preferably, the first metal electrode and the second metal electrode are separated by a distance of 2-4 mm in a parallel arrangement with variations in distance less than +/−20 µm. Furthermore, the surface of the electrodes should be as smooth as possible without pin holes or peaks. Electrodes having a roughness Rz of 1 to 10 µm are preferred. In other embodiments, the electroporation device includes at least one additional electrode which applies a ground potential to, e.g., the sipper portion of the electroporation device.

Although illustrated as a single unit device 500, in other embodiments, the electroporation module includes multiple electroporation units. Each electroporation unit may be configured to electroporate cell sample volumes of between 1 µl to 20 ml. For example, differing volume capacities of electroporation units may be available in a multi-unit electroporation device.

In a multi-unit electroporation module, in some embodiments, the electrodes are independent, standalone elements. In other embodiments, a multi-unit electroporation device may include electrodes arranged such that electroporation cuvettes in adjacent electroporation units share electrodes. Such multi-unit electroporation devices may include, e.g., 2 or more electroporation units, 4 or more electroporation units, 8 or more electroporation units, 16 or more electroporation units, 32 or more electroporation units, 48 or more electroporation units, 64 or more electroporation units, or even 96 or more electroporation units preferably in an automated device. Where multiple parallel devices are employed, typically like volumes are used in each unit.

Although example dimensions are provided, the dimensions, of course, will vary depending on the volume of the cell sample and the container(s) that are used to contain the cells and/or material to be electroporated.

In preferred embodiments, the transformation module includes at least one flow-through electroporation device having a housing with an electroporation chamber, a first electrode and a second electrode configured to engage with an electric pulse generator. In some implementations, the flow-through electroporation devices are configured to mate with a replaceable cartridge such as the cartridges 104, 106 of FIG. 1A (e.g., transformation module 110c), by which electrical contacts engage with the electrodes of the electroporation device. In certain embodiments, the electroporation devices are autoclavable and/or disposable, are packaged with reagents in the reagent cartridge, and/or may be removable from the reagent cartridge. The electroporation device may be configured to electroporate cell sample volumes between 1 µl to 2 ml, 10 µl to 1 ml, 25 µl to 750 µl, or 50 µl to 500 µl. The cells that may be electroporated with the disclosed electroporation devices include mammalian cells (including human cells), plant cells, yeasts, other eukaryotic cells, bacteria, archaea, and other cell types.

Figure 5B:
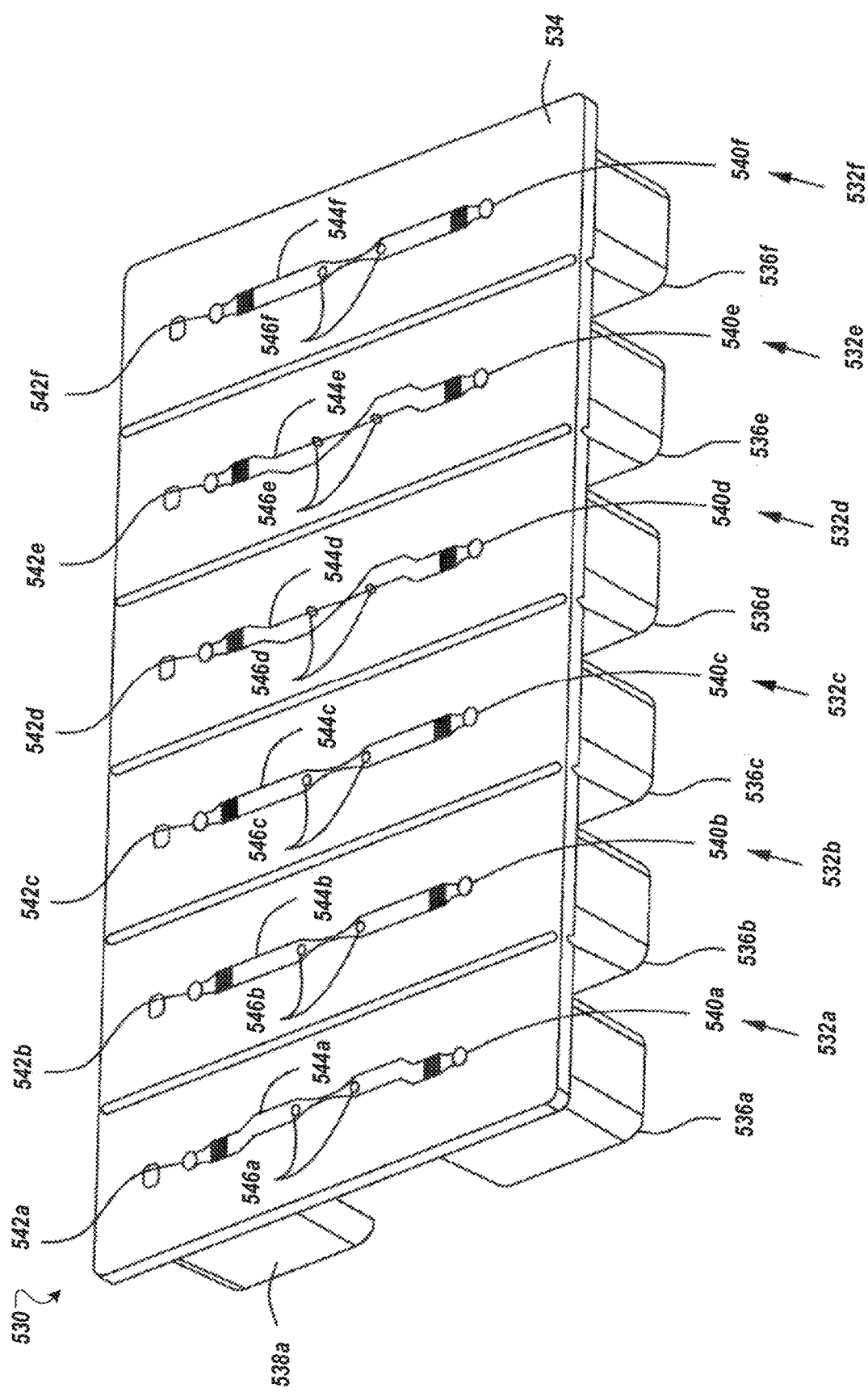
FIGS. 5B and 5C depict an example disposable flow-through electroporation module for use in an automated multi-module cell processing instrument.
Figure 5C:
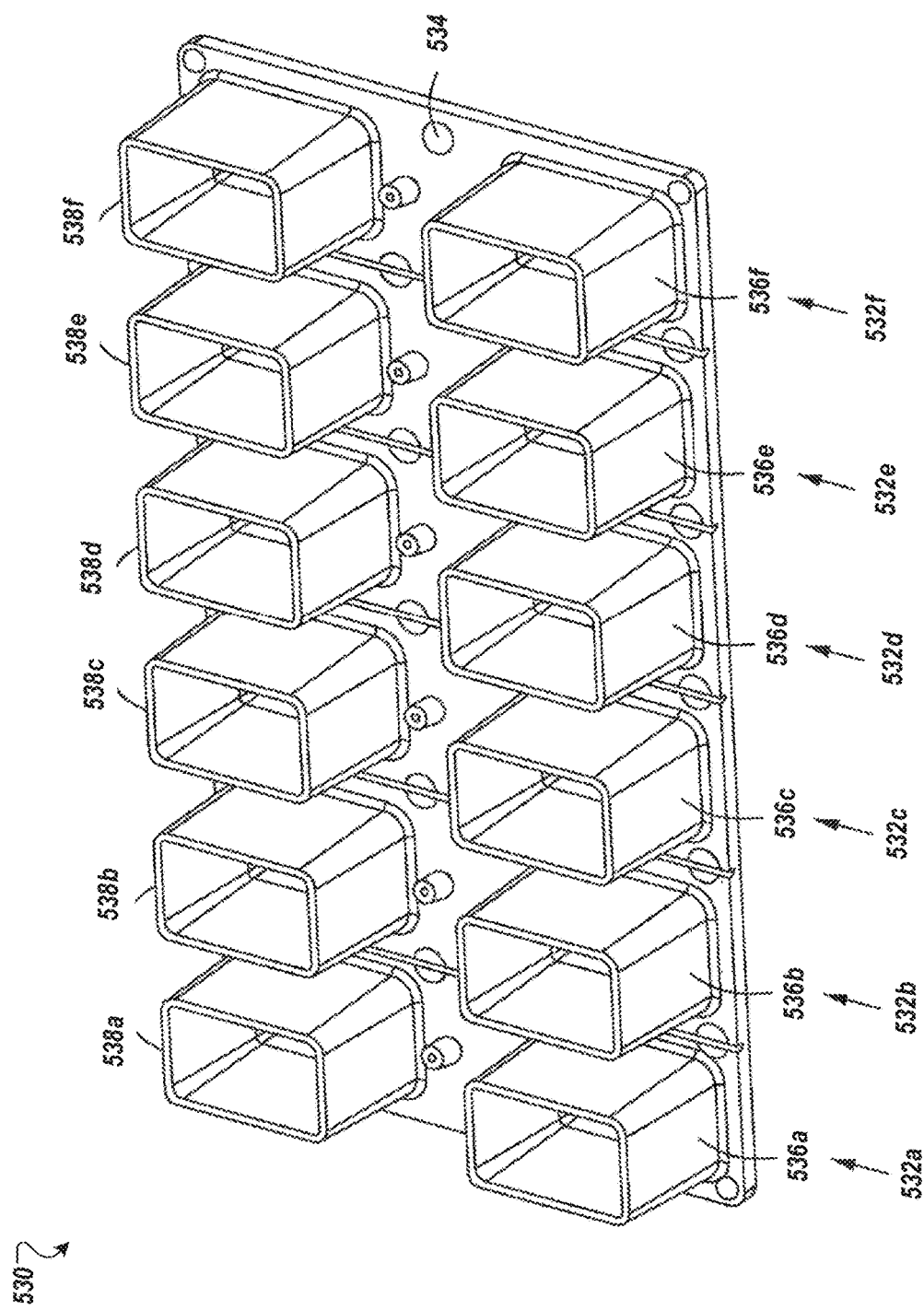

The reagent cartridges for use in the automated multi-module cell processing systems (e.g., cartridge 104 of FIG. 1A), in some embodiments, include one or more electroporation devices (e.g., electroporation module 110c of FIG. 1A), preferably flow-through electroporation devices. FIG. 5B is a bottom perspective view of a set 530 of six co-joined flow-through electroporation devices (e.g., units or modules) 532a-f that may be part of a reagent cartridge, and FIG. 5C is a top perspective view of the same. The cartridge may include one to six or more flow-through electroporation units 532a-f arranged on a single substrate 534. Each of the six flow-through electroporation units 532a-f have corresponding wells 536a-f that define cell sample inlets and wells 538a-f (see FIG. 5C) that define cell sample outlets. Additionally, as seen in FIG. 5B, each electroporation unit 532a-f includes a respective inlet 540a-f, a respective outlet 542a-f, a respective flow channel 544a-f, and two electrodes 546a-f on either side of a constriction in the respective flow channel 544a-f of each flow-through electroporation unit 532a-f.

Once the six flow-through electroporation units 532a-f are fabricated, in some embodiments, they can be separated from one another along the score lines separating each unit from the adjacent unit (i.e., "snapped apart") and used one at a time, or alternatively in other embodiments two or more flow-through electroporation units 532a-f can be used in parallel, in which case those two or more units preferably remain connected along the score lines.

Generally speaking, microfluidic electroporation—using cell suspension volumes of less than approximately 10 ml and as low as 1 µl—allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated, automatic, multi-module cell processing and analysis.

The flow-through electroporation devices included in the reagent cartridges can achieve high efficiency cell electroporation with low toxicity. In specific embodiments of the disclosure the flow-through electroporation devices of the disclosure the toxicity level of the transformation results in greater than 10% viable cells after electroporation, preferably greater than 15%, 20%, 25%, 30%, 35%, 40%, 45%, 50%, 55%, 60%, 70%, 75%, 80%, 85%, 90%, or even 95% viable cells following transformation, depending on the cell type and the nucleic acids being introduced into the cells.

After transformation, the cells are allowed to recover under conditions that promote the genome editing process that takes place as a result of the transformation and expression of the introduced nucleic acids in the cells.

Method for Automated Multi-Module Cell Processing

Figure 9:
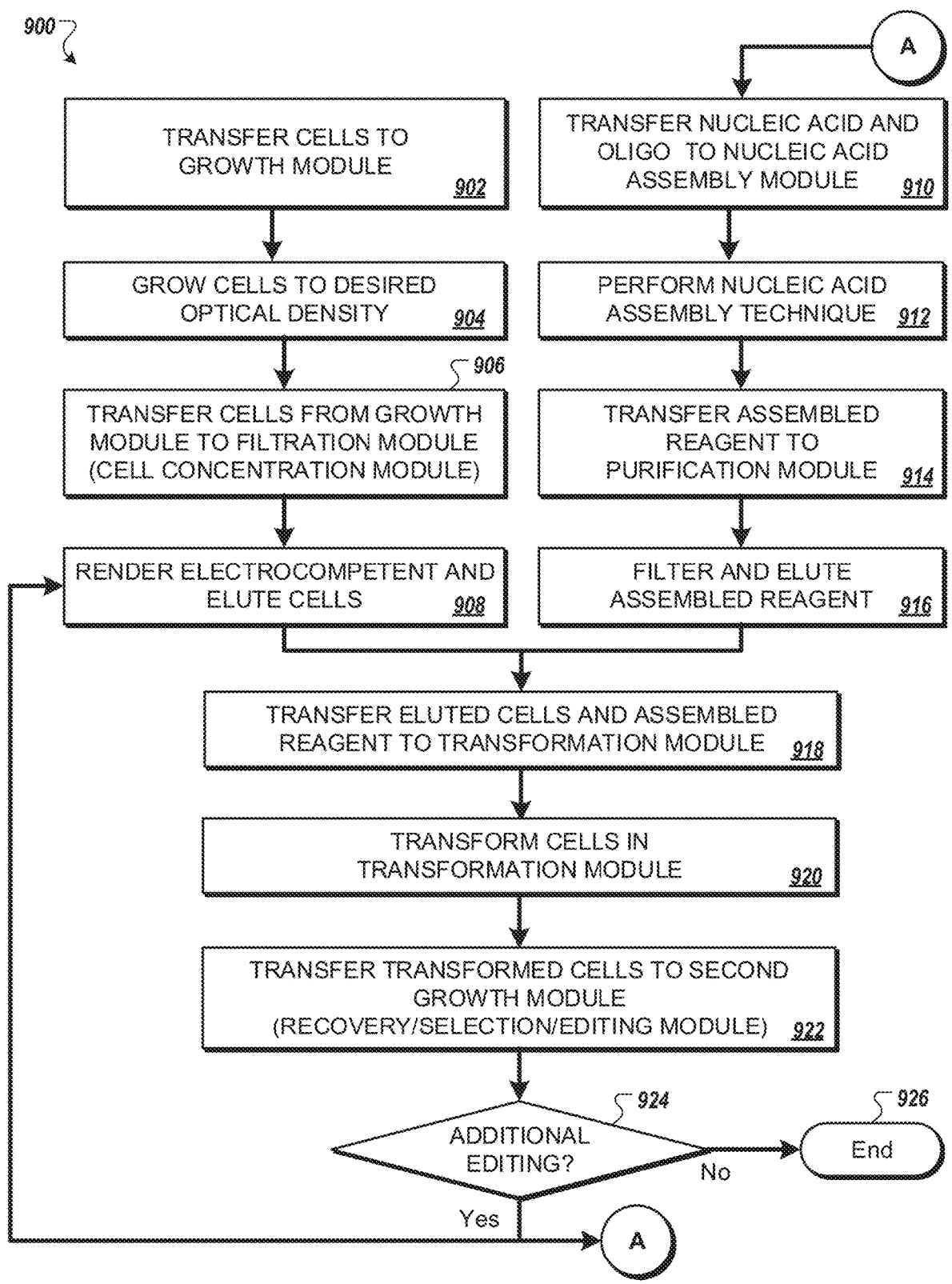
FIG. 9 is a flow chart of an example method for automated multi-module cell processing.

FIG. 9 is a flow chart of an example method 900 for using an automated multi-module cell processing system such as the systems illustrated in FIGS. 1A-1B and 12A-12B. The processing system of FIG. 13, for example, may direct the processing stage of the method 900. For example, a software script may identify settings for each processing stage and instructions for movement of a robotic handling system to perform the actions of the method 900. In some embodiments, a software instruction script may be identified by a cartridge supplied to the automated multi-module cell processing instrument. For example, the cartridge may include machine-readable indicia, such as a bar code or QR code, including identification of a script stored in a memory of the automated multi-module cell processing instrument (e.g., such as memory 1302 of FIG. 13). In another example, the cartridge may contain a downloadable script embedded in machine-readable indicia such as a radio frequency (RF) tag. In other embodiments, the user may identify a script, for example through downloading the script via a wired or wireless connection to the processing system of the automated multi-module cell processing instrument or through selecting a stored script through a user interface of the automated multi-module cell processing instrument. In a particular example, the automated multi-module cell processing instrument may include a touch screen interface for submitting user settings and activating cell processing.

In some implementations, the method 900 begins with transferring cells to a growth module (902). The growth module, for example, may be the growth module 800 described in relation to FIGS. 8A through 8F. In a particular example, the processing system 120 may direct the robotic handling system 108 to transfer cells 106 to the growth module 110a, as described in relation to FIGS. 12A and 12B. In another example, as described in relation to FIG. 1A, the cells may be transferred from one of the cartridges 104, 106 to the growth modules 110a, 110b by the robotic handling system 108. In some embodiments, the growth vial may contain growth media and be supplied, e.g., as part of a kit. In other embodiments, the growth vial may be filled with medium transferred, e.g., via the liquid handling device, from a reagent container.

In some embodiments, prior to transferring the cells (e.g., from the reagent cartridge 104 or from a vial added to the instrument), machine-readable indicia may be scanned upon the vial or other container situated in a position designated for cells to confirm that the vial or container is marked as containing cells. Further, the machine-readable indicia may indicate a type of cells provided to the instrument. The type of cells, in some embodiments, may cause the instrument to select a particular processing script (e.g., series of instructions for the robotic handling system and settings and activation of the various modules).

In some implementations, the cells are grown in the growth module to a desired optical density (904). For example, the processing system 126 of FIGS. 1A-1B or processing system 1220 of FIGS. 12A-B may manage a temperature setting of the growth module 110a for incubating the cells during the growth cycle. The processing system 126, 1220 may further receive sensor signals from the growth module 110a, 110b indicative of optical density and analyze the sensor signals to monitor growth of the cells. In some embodiments, a user may set growth parameters for managing growth of the cells. For example, temperature, and the degree of agitation of the cells. Further, in some embodiments, the user may be updated regarding growth process. The updates, in some examples, may include a message presented on a user interface of the automated multi-module cell processing system, a text message to a user's cell phone number, an email message to an email account, or a message transmitted to an app executing upon a portable electronic device (e.g., cell phone, tablet, etc.). Responsive to the messages, in some embodiments, the user may modify parameters, such as temperature, to adjust cell growth. For example, the user may submit updated parameters through a user interface of the automated multi-module cell processing system or through a portable computing device application in communication with the automated multi-module cell processing system, such as a user interface 1100 of FIG. 11.

Although described in relation to optical density, in other implementations, cell growth within the growth module may be monitored using a different measure of cell density and physiological state such as, in some examples, pH, dissolved oxygen, released enzymes, acoustic properties, and electrical properties.

In some implementations, upon reaching the desired optical density (904), the cells are transferred from the growth module to a filtration module or cell wash and concentration module (906). The robotic handling system 108 of FIGS. 1A-1B or 1208 of FIGS. 12A-12B, for example, may transfer the cells from the growth module 1210a to the filtration module 1210b. The filtration module, for example, may be designed to render the cells electrocompetent. Further, the filtration module may be configured to reduce the volume of the cell sample to a volume appropriate for electroporation. In another example, the filtration module may be configured to remove unwanted components, such as salts, from the cell sample. In some embodiments, the robotic handling system 108 transfers a washing solution to the filtration module 1210b for washing the cells.

In some implementations, the cells are rendered electrocompetent and eluted in the filtration module or cell wash and concentration module (908). The cells may be eluted using a wash solution. For example, the cells may be eluted using reagents from a reagent supply. The filtration module or cell wash and concentration module, for example, may be similar to the filtration module 700 illustrated in FIGS. 7A and 7B. As discussed above, numerous different methods can be used to wash the cells, including density gradient purification, dialysis, ion exchange columns, filtration, centrifugation, dilution, and the use of beads for purification. In some aspects, the cell wash and concentration module utilizes a centrifugation device. In other aspects, the filtration module utilizes a filtration instrument. In yet other aspects, the beads are coupled to moieties that bind to the cell surface. These moieties include but are not limited to antibodies, lectins, wheat germ agglutinin, mutated lysozymes, and ligands. In other aspects, the cells are engineered to be magnetized, allowing magnets to pellet the cells after wash steps. Mechanism of cell magnetization can include but not limited to ferritin protein expression.

In some embodiments, the wash solution is transferred to the filtration module prior to eluting. The robotic handling system 108 of FIGS. 12A-12B, for example, may transfer the wash solution from a vial or container situated in a position designated for wash solution. Prior to transferring the wash solution, machine-readable indicia may be scanned upon the vial or other container or reservoir situated in the position designated for the wash solution to confirm the contents of the vial, container, or reservoir. Further, the machine-readable indicia may indicate a type of wash solution provided to the instrument. The type of wash solution, in some embodiments, may cause the system to select a particular processing script (e.g., settings and activation of the filtration module appropriate for the particular wash solution).

In other embodiments, the cells are eluted in a cell wash module of a wash cartridge. For example, the eluted cells may be collected in an empty vessel of the wash cartridge 106 illustrated in FIG. 1A, and the robotic handling system 108 may transfer media from the reagent cartridge 104 (or a reagent well of the wash cartridge 10b) to the eluted cells.

Once the cells have been rendered electrocompetent and suspended in an appropriate volume such as 50 μL to 10 mL, or 100 μL to 80 mL, or 150 μL to 8 mL, or 250 μL to 7 mL, or 500 μL to 6 mL, or 750 μL to 5 mL for transformation by the filtration module (906), in some implementations, the cells are transferred to a transformation module (918). The robotic handling system 108 of FIGS. 1A-1B, for example, may transfer the cells from the filtration module to the transformation module 110c. The filtration module may be physically coupled to the transformation module, or these modules may be separate. In an embodiment such as the instrument 100 of FIG. 1A having cartridge-based supplies, the cells may be eluted to a reservoir within a cartridge, such as the reagent cartridge 104, prior to transferring to the transformation module.

In some implementations, nucleic acids are prepared outside of the automated multi-module cell processing instrument. For example, an assembled vector or other nucleic acid assembly may be included as a reagent by a user prior to running the transformation process and other processes in the method 900.

However, in other implementations, nucleic acids are prepared by the automated multi-module cell processing instrument. A portion of the following steps 910 through 916, in some embodiments, are performed in parallel with a portion of steps 902 through 908. At least a portion of the following steps, in some embodiments, are performed before and/or after steps 902 through 908.

In some implementations nucleic acids such as an editing oligonucleotide and a vector back bone, as well as, in some examples, enzymes and other reaction components are transferred to a nucleic acid assembly module (910). The nucleic acid assembly module may be configured to perform one or more of a wide variety of different nucleic acid assembly techniques in an automated fashion. Nucleic acid assembly techniques that can be performed in the nucleic acid assembly module may include, but are not limited to, those assembly methods that use restriction endonucleases, including PCR, BioBrick assembly, Type IIS cloning (e.g., GoldenGate assembly), and Ligase Cycling Reaction. In other examples, the nucleic acid assembly module may perform an assembly technique based on overlaps between adjacent parts of the nucleic acids, such as Gibson Assembly®, CPEC, SLIC, Ligase Cycling etc. Additional example assembly methods that may be performed by the nucleic acid assembly module include gap repair in yeast, gateway cloning and topoisomerase-mediated cloning. The nucleic acid assembly module, for example, may be the nucleic acid assembly module 400 described in relation to FIG. 4. In a particular example, the processing system 120 may direct the robotic handling system 1208 to transfer nucleic acids 1206 to the nucleic acid assembly module 1210e, as described in relation to FIG. 12B. In another example, as described in relation to FIG. 1A, the nucleic acids may be transferred from one of the cartridges 104, 106 to a nucleic acid assembly module by the robotic handling system 108.

In some embodiments—prior to transferring each of the nucleic acid samples, the enzymes, and other reaction components—machine-readable indicia may be scanned upon the vials or other containers situated in positions designated for these materials to confirm that the vials or containers are marked as containing the anticipated material. Further, the machine-readable indicia may indicate a type of one or more of the nucleic acid samples, the enzymes, and other reaction components provided to the instrument. The type(s) of materials, in some embodiments, may cause the instrument to select a particular processing script (e.g., series of instructions for the robotic handling system to identify further materials and/or settings and activation of the nucleic acid assembly module).

In some embodiments, the nucleic acid assembly module is temperature controlled depending upon the type of nucleic acid assembly used. For example, when PCR is utilized in the nucleic acid assembly module, the module can have a thermocycling capability allowing the temperatures to cycle between denaturation, annealing and extension. When single temperature assembly methods are utilized in the nucleic acid assembly module, the module can have the ability to reach and hold at the temperature that optimizes the specific assembly process being performed.

Temperature control, in some embodiments, is managed by a processing system of the automated multi-module cell processing instrument, such as the processing system 1310 of FIG. 13. These temperatures and the duration of maintaining the temperatures can be determined by a preprogrammed set of parameters (e.g., identified within the processing script or in another memory space accessible by the processing system), or manually controlled by the user through interfacing with the processing system.

Once sufficient time has elapsed for the assembly reaction to take place, in some implementations, the nucleic acid assembly is transferred to a purification module (914). The processing system, for example, may monitor timing of the assembly reaction based upon one or more of the type of reaction, the type of materials, and user settings provided to the automated multi-module cell processing instrument. The robotic handling system 108 of FIGS. 1A-1B or 12A-12B, for example, may transfer the nucleic acid assembly to the purification module through a sipper or pipettor interface. In another example, the robotic handling system 108 of FIGS. 1A-1B or 12A-12B may transfer a vial containing the nucleic acid assembly from a chamber of the nucleic acid assembly module to a chamber of the de-salt/purification module.

In some implementations, the nucleic acid assembly is de-salted and eluted at the purification module (916). The purification module, for example, may remove unwanted components of the nucleic acid assembly mixture (e.g., salts, minerals, etc.). In some embodiments, the purification module concentrates the assembled nucleic acids into a smaller volume that the nucleic acid assembly volume. Examples of methods for exchanging liquid following nucleic acid assembly include magnetic beads (e.g., SPRI or Dynal (Dynabeads) by Invitrogen Corp. of Carlsbad, Calif.), silica beads, silica spin columns, glass beads, precipitation (e.g., using ethanol or isopropanol), alkaline lysis, osmotic purification, extraction with butanol, membrane-based separation techniques, filtration etc. For example, one or more micro-concentrators fitted with anisotropic, hydrophilic-generated cellulose membranes of varying porosities may be used. In another example, the de-salt/purification module may process a liquid sample including a nucleic acid and an ionic salt by contacting the mixture with an ion exchanger including an insoluble phosphate salt, removing the liquid, and eluting nucleic acid from the ion exchanger.

In an illustrative embodiment, the nucleic acid assembly may be combined with magnetic beads, such as SPRI beads, in a chamber of a purification module. The nucleic acid assembly may be incubated at a set temperature for sufficient time for the nucleic acid assembly to bind to the magnetic beads. After incubation, a magnet may be engaged proximate to the chamber so that the nucleic acid assembly can be washed and eluted. An illustrative example of this process is discussed in relation to the combination isothermal nucleic acid assembly and purification module of FIG. 4.

Once the nucleic acid assembly has been eluted, the nucleic acid assembly, in some implementations, is transferred to the transformation module (918). The robotic handling system 108 of FIGS. 1A-1B or 12A-12B, for example, may transfer the nucleic acid assembly to the transformation module through a sipper or pipettor interface to, e.g., a cuvette-based electroporator module or a flow-through electroporator module, as described above. For example, the de-salted assembled nucleic acids, during the transfer, may be combined with the electrocompetent cells from step 908. In other embodiments, the transformation module may accept each of the electrocompetent cells and the nucleic acid assembly separately and enable the mixing (e.g., open one or more channels to combine the materials in a shared chamber).

The cells may be transformed in the transformation module (920). Transformation may involve any art-recognized technique for introducing an exogenous nucleic acid sequence (e.g., DNA) into a target cell (either transformation or transfection), including, in some examples, electroporation, lipofection, optoporation, injection, microprecipitation, microinjection, liposomes, particle bombardment, sonoporation, laser-induced poration, bead transfection, calcium phosphate or calcium chloride co-precipitation, or DEAE-dextran-mediated transfection. In some embodiments, hybrid techniques that exploit the capabilities of mechanical and chemical transfection methods can be used, such as magnetofection, a transfection methodology that combines chemical transfection with mechanical methods. In another example, cationic lipids may be deployed in combination with gene guns or electroporators.

In some implementations, the transformation module uses electroporation to trigger uptake of the DNA material. A buffer or medium may be transferred to the transformation module and added to the cells so that the cells may be suspended in a buffer or medium that is favorable for cell survival during electroporation. Prior to transferring the buffer or medium, machine-readable indicia may be scanned upon the vial or other container or reservoir situated in the position designated for the buffer or medium to confirm the contents of the vial, container, or reservoir. Further, the machine-readable indicia may indicate a type of buffer or medium provided to the instrument. The type of buffer or medium, in some embodiments, may cause the instrument to select a particular processing script (e.g., settings and activation of the transformation module appropriate for the particular buffer or medium). For bacterial cell electroporation, low conductance mediums, such as water or glycerol solutions, may be used to reduce the heat production by transient high current. For yeast cells a sorbitol solution may be used. For mammalian cell electroporation, cells may be suspended in a highly conductive medium or buffer, such as MEM, DMEM, IMDM, RPMI, Hanks', PBS, HBSS, HeBS and Ringer's solution. In a particular example, the robotic handling system 108 may transfer a buffer solution to the transformation module 110c from one of the cartridges 104, 106. The transformation module, for example, may be a flow-through electroporation module such as the electroporation modules described in relation to FIGS. 5A and 5B. As described in relation to FIG. 1A and FIG. 5B, the transformation module may be a disposable flow-through electroporation module 110c provided with the cartridge 104 of FIG. 1A.

In some implementations, the transformation module further prepares the cells for nucleic acid uptake. For example, bacterial cells may be treated with a sucrose or glycerol wash prior to addition of nucleic acids, and yeast cells may be treated with a solution of lithium acetate, dithiotheitol (DTT) and TE buffer. In other implementations involving preparation of cells for nucleic acid uptake, the filtration module or another separate module (e.g., a cell wash module) may prepare the cells for nucleic acid update.

Once transformed, the cells are transferred to a second growth/recovery/editing module (922). The robotic handling system 108 of FIGS. 1A-1B or 12A-12B, for example, may transfer the transformed cells to the second growth module through a sipper or pipettor interface. In another example, the robotic handling system 108 of 1A-1B or 12A-12B may transfer a vial containing the transformed cells from a chamber of the transformation module to a chamber of the second growth module.

The second growth module, in some embodiments, acts as a recovery module, allowing the cells to recover from the transformation process. In other embodiments, the cells may be provided to a separate recovery module prior to being transported to the second growth module. During recovery, the second growth module allows the transformed cells to uptake and, in certain aspects integrate the introduced nucleic acids into the genome of the cell. The second growth module may be configured to incubate the cells at any user-defined temperature optimal for cell growth, preferably 25°, 30°, or 37° C.

In some embodiments, the second growth module behaves as a selection module, selecting the transformed cells based on an antibiotic or other reagent. In one example, the RNA-guided nuclease (RGN) protein system is used for selection to cleave the genomes of cells that have not received the desired edit. The RGN protein system used for selection can either be the same or different as the RGN used for editing. In the example of an antibiotic selection agent, the antibiotic may be added to the second growth module to enact selection. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, or chloramphenicol-resistance gene. The robotic handling system 108 of FIGS. 1A-1B or 12A-12B, for example, may transfer the antibiotic to the second growth module through a sipper or pipettor interface. In some embodiments, removing dead cell background is aided using lytic enhancers such as detergents, osmotic stress by hypnotic wash, temperature, enzymes, proteases, bacteriophage, reducing agents, or chaotropes. The processing system 1310 of FIG. 13, for example, may alter environmental variables, such as temperature, to induce selection, while the robotic handling system 108 of FIGS. 1A-1B or 12A-12B may deliver additional materials (e.g., detergents, enzymes, reducing agents, etc.) to aid in selection. In other embodiments, cell removal and/or media exchange by filtration is used to reduce dead cell background.

In further embodiments, in addition to or as an alternative to applying selection, the second growth module serves as an editing module, allowing for genome editing in the transformed cells. Alternatively, in other embodiments the cells post-recovery and selection (if performed) are transferred to a separate editing module. As an editing module, the second growth module induces editing of the cells' genomes, e.g., through expression of the introduced nucleic acids. Expression of the nuclease may involve one or more of chemical, light, viral, or temperature induction. The second growth module, for example, may be configured to heat or cool the cells during a temperature induction process. In a particular illustration, the cells may be induced by heating at 42° C.-50° C. Further to the illustration, the cells may then be are cooled to 0-10° C. after induction. In the example of chemical or viral induction, an inducing agent may be transferred to the second growth module to induce editing. If an inducible nuclease was introduced to the cells, during editing, the inducible nuclease is induced through introduction of an inducer molecule, such as the inducer molecule 1224 described in relation to FIG. 12A. The inducing agent or inducer molecule, in some implementations, is transferred to the second growth module by the robotic handling system 108 of FIGS. 1A-1B or 12A-12B (e.g., through a pipettor or sipper interface).

In some implementations, if no additional cell editing is desired (924), the cells may be transferred from the cell growth module to a storage unit for later removal from the automated multi-module cell processing system (926). The storage unit, for example, may include the storage unit 114 of FIGS. 12A-12B. The robotic handling system 108 of FIGS. 1A-1B or 12A-12B, for example, may transfer the cells to the storage unit 114 through a sipper or pipettor interface. In another example, the robotic handling system 108 of FIGS. 1A-1B or 12A-12B may transfer a vial containing the cells from a chamber of the second growth module to a vial or tube within the storage unit.

In some implementations, if additional cell editing is desired (924), the cells may be transferred to the same or a different filtration module and rendered electrocompetent (908). Further, in some embodiments, a new assembled nucleic acid sample may be prepared by the nucleic acid assembly module at this time. Prior to recursive editing, in some embodiments, the automated multi-module cell processing instrument may require additional materials (e.g., replacement cartridges) be supplied by the user.

The steps may be the same or different during the second round of editing. For example, in some embodiments, upon a subsequent execution of step 904, a selective growth medium is transferred to the growth module to enable selection of edited cells from the first round of editing. The robotic handling system 108 of FIGS. 1A-B or 12A-B, for example, may transfer the selective growth medium from a vial or container in a reagent cartridge situated in a position designated for selective growth medium. Prior to transferring the selective growth medium, machine-readable indicia may be scanned upon the vial or other container or reservoir situated in the position designated for the selective growth medium to confirm the contents of the vial, container, or reservoir. Further, the machine-readable indicia may indicate a type of selective growth medium provided to the instrument. The type of selective growth medium, in some embodiments, may cause the instrument to select a particular processing script (e.g., settings and activation of the growth module appropriate for the particular selective growth medium). Particular examples of recursive editing workflows are described in relation to FIGS. 10A through 10C.

In some implementations, the method 900 can be timed to request materials and/or complete the editing cycle in coordination with a user's schedule. For example, the automated multi-module cell processing instrument may provide the user the ability to schedule completion of one or more cell processing cycles (e.g., one or more recursive edits) such that the method 900 is enacted with a goal of completion at the user's preferred time. The time scheduling, for example, may be set through a user interface, such as the user interface 1316 of FIG. 13. In a particular illustration, a user may set completion of a first cycle to 4:00 PM so that the user can supply additional cartridges of materials to the automated multi-module cell processing instrument to enable overnight processing of another round of cell editing.

In some implementations, throughout the method 900, the automated multi-module cell processing instrument may alert the user to its current status. For example, the user interface 1316 of FIG. 13 may present a graphical indication of the present stage of processing. In a particular example, a front face of the automated multi-module call processing instrument may be overlaid with a user interface (e.g., touch screen) that presents an animated graphic depicting present status of the cell processing. The user interface may further present any user and/or default settings associated with the current processing stage (e.g., temperature setting, time setting, etc.).

Although illustrated as a particular series of operations, in other embodiments, more or fewer steps may be included in the method 900. For example, in some embodiments, prior to engaging in each round of editing, the contents of reservoirs, cartridges, and/or vials may be screened to confirm appropriate materials are available to proceed with processing. For example, in some embodiments, one or more imaging sensors (e.g., barcode scanners, cameras, etc.) may confirm contents at various locations within the housing of the automated multi-module cell processing instrument. In one example, multiple imaging sensors may be disposed within the housing of the automated multi-module cell processing instrument, each imaging sensor configured to detect one or more materials (e.g., machine-readable indicia such as barcodes or QR codes, shapes/sizes of materials, etc.). In another example, at least one imaging sensor may be moved by the robotic handling system to multiple locations to detect one or more materials. In further embodiments, one or more weight sensors may detect presence or absence of disposable or replaceable materials. In an illustrative example, the transfer tip supply holder 116 may include a weight sensor to detect whether or not tips have been loaded into the region. In another illustrative example, an optical sensor may detect that a level of liquid waste has reached a threshold level, requiring disposal prior to continuation of cell processing. Requests for additional materials, removal of waste supplies, or other user interventions (e.g., manual cleaning of one or more elements, etc.), in some implementations, are presented on a graphical user interface of the automated multi-module cell processing instrument. The automated multi-module cell processing instrument, in some implementations, contacts the user with requests for new materials or other manual interventions, for example through a software app, email, or text message.

Workflows for Cell Processing in an Automated Multi-Module Cell Processing Instrument The automated multi-module cell processing instrument is designed to perform a variety of cell processing workflows using the same modules. For example, source materials, in individual containers or in cartridge form, may differ and the corresponding instructions (e.g., software script) may be selected accordingly, using the same basic instrumentation and robotic handling system; that is, the multi-module cell processing system can be configured to perform a number of different workflows for processing cell samples and different types of cell samples. In embodiments, a same workflow may be performed iteratively to recursively edit a cell sample. In other embodiments, a cell sample is recursively edited, but the workflow may change from iteration to iteration.

Figure 10A:
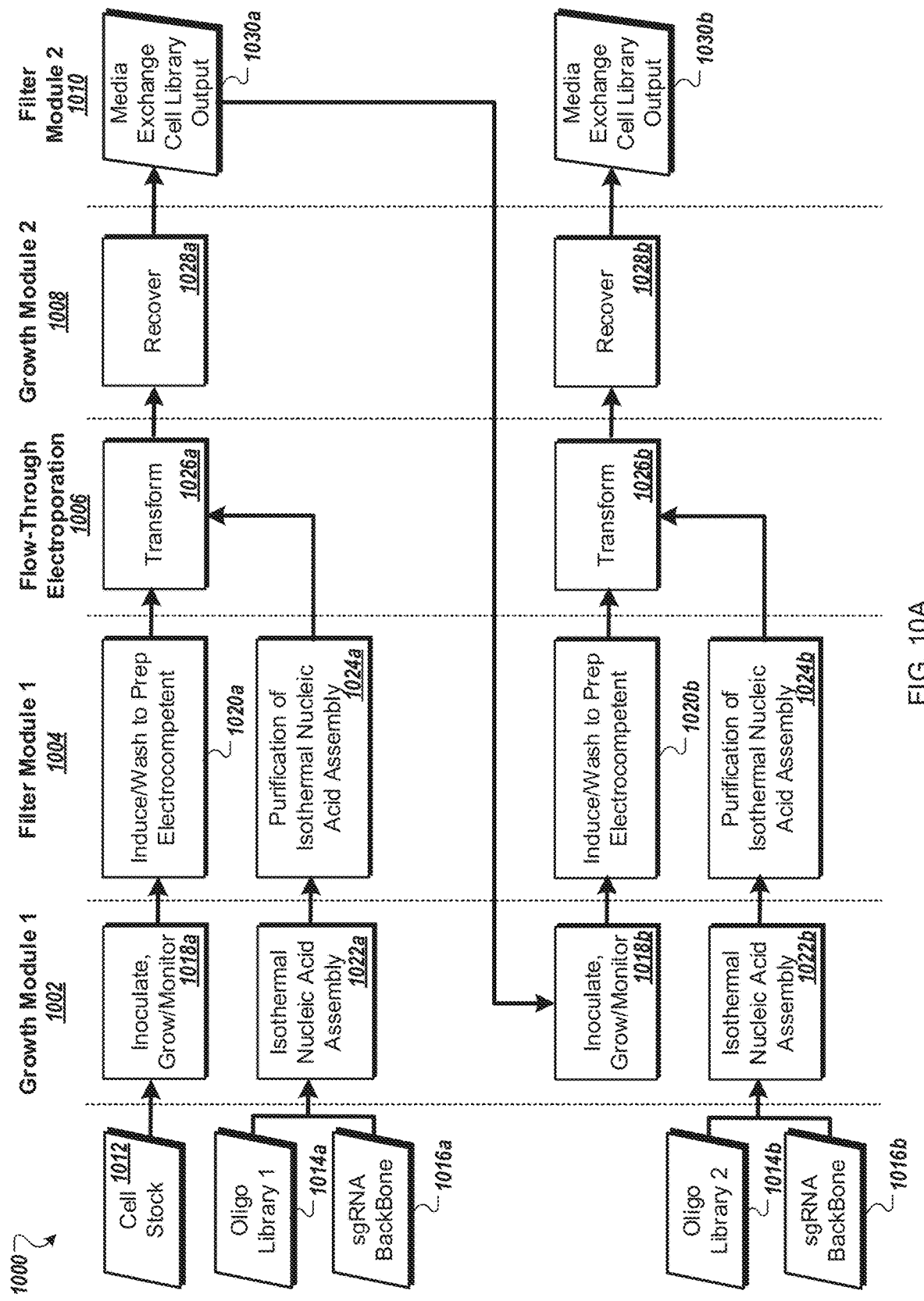
FIG. 10A is a flow diagram of a first example workflow for automated processing of bacterial cells by an automated multi-module cell processing instrument.
Figure 10B:
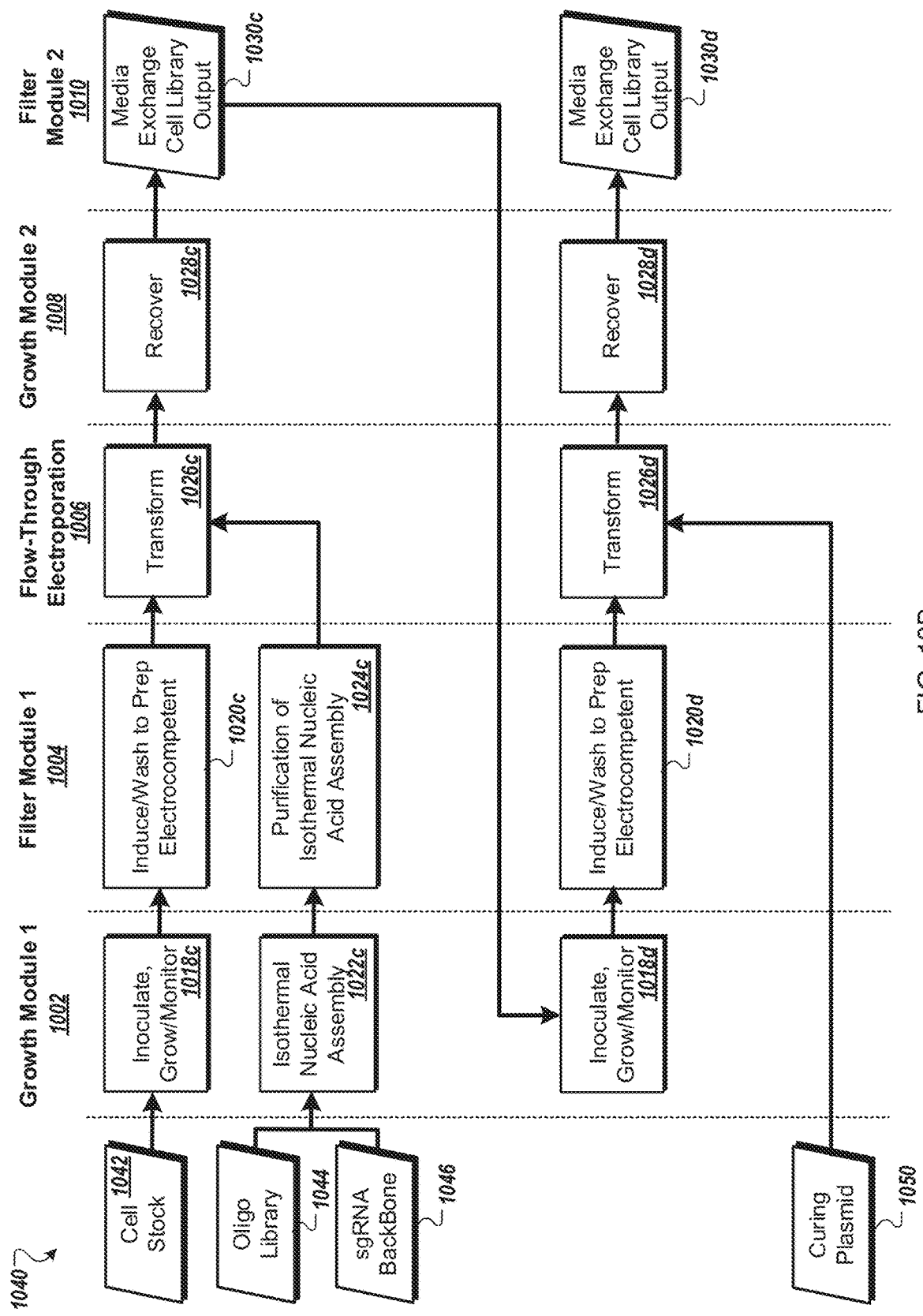
FIG. 10B is a flow diagram of a second example workflow for automated processing of a bacterial cells by an automated multi-module cell processing instrument.
Figure 10C:
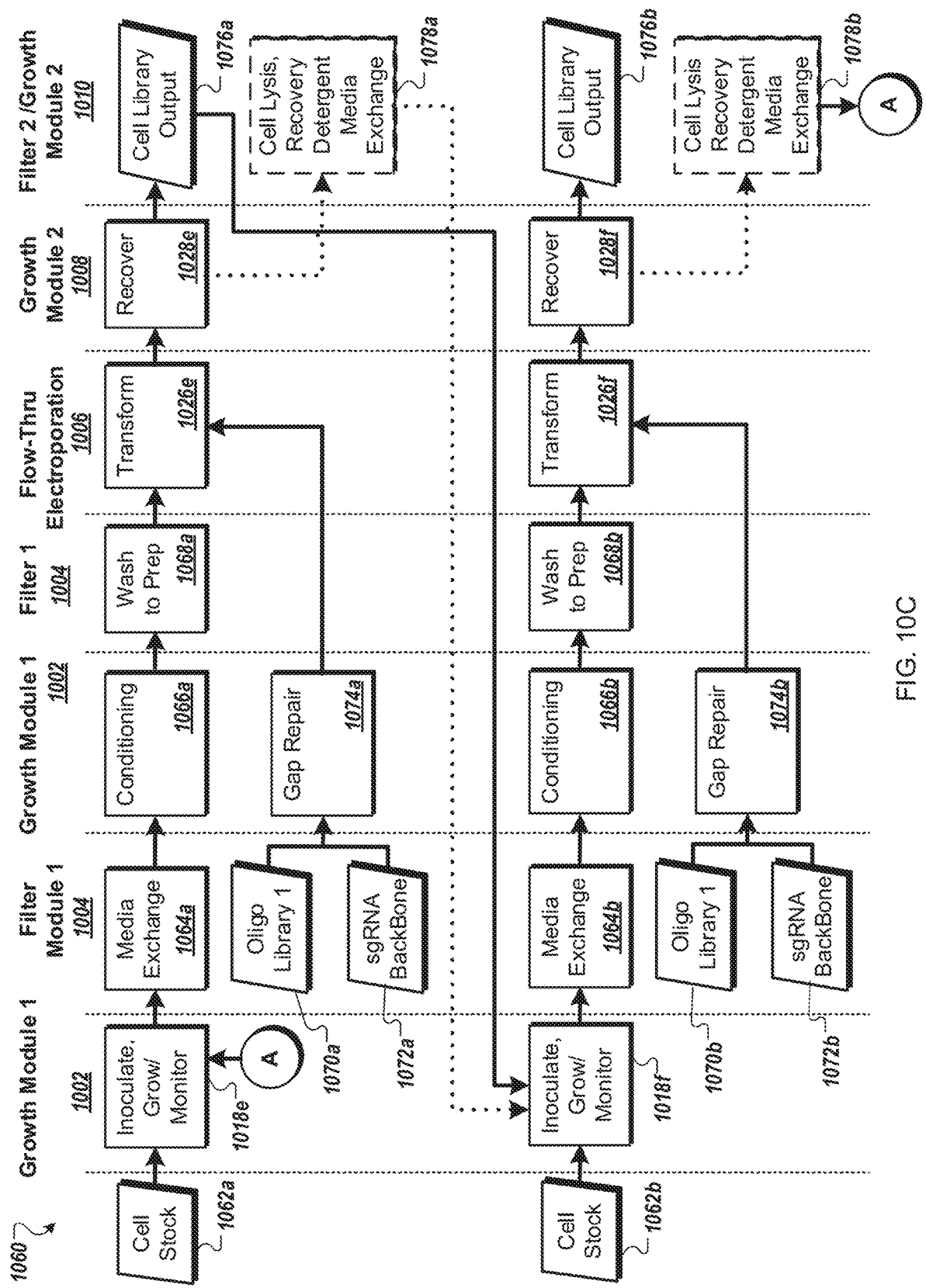
FIG. 10C is a flow diagram of an example workflow for automated cell processing of yeast cells by an automated multi-module cell processing instrument.

FIGS. 10A through 10C illustrate example workflows that may be performed using an automated multi-module cell processing instrument including two cell growth modules 1002, 1008, two filtration modules 1004 and 1010, and a flow-through electroporation module 1006. Although described as separate growth modules 1002, 1008 and filtration modules 1004, 1010, each may instead be designed as a dual module. For example, a dual growth module, including growth modules 1002 and 1008, may include dual rotating growth vials sharing some circuitry, controls, and a power source and disposed in a same housing. Similarly, a dual filtration module may include filtration modules 1004 and 1010, including two separate filters and liquid supply tubes but sharing circuitry, controls, a power source, and a housing. The modules 1002, 1004, 1006, 1008, and 1010, for example, may be part of the instrument 100 described in relation to FIGS. 1A and 1B.

Turning to FIG. 10A, a flow diagram illustrates a first bacteria genome editing workflow 1000 involving two stages of processing having identical processing steps, resulting in two edits to a cell stock 1012. Each stage may operate based upon a different cartridge of source materials. For example, a first cartridge may include a first oligo library 1014a and a first sgRNA backbone 1016a. A second cartridge, introduced into the automated multi-module cell processing instrument between processing stages or prior to processing but in a different position than the first cartridge, may include a second oligo library 1014b and a second sgRNA backbone 1016b. Each cartridge may be considered as a "library cartridge" for building a library of edited cells. The cell stock 1012, in some embodiments, is included in the first library cartridge. The cell stock 1012 may be supplied within a kit including the two cartridges. Alternatively, a user may add a container (e.g., vial or tube) of the cell stock 1012 to a purchased cartridge.

The workflow 1000, in some embodiments, is performed based upon a script executed by a processing system of the automated multi-module cell processing instrument, such as the processing system 1310 of FIG. 13. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1012 into the first growth module 1002 for inoculation, growth, and monitoring (1018a). In one example, a robotic handling system adds a vial of the cell stock 1012 to medium contained in the rotating growth vial of the first growth module 1002. In another example, the robotic handling system pipettes cell stock 1012 from the first cartridge and adds the cell stock 1012 to the medium contained in the rotating growth vial. The cells may have been maintained at a temperature of 4° C. at this point. In a particular example, 20 ml of cell stock may be grown within a rotating growth vial of the first growth module 1002 at a temperature of 30° C. to an OD of 0.50. The cell stock 1012 added to the first growth module 1002 may be monitored over time until 0.50 OD is sensed via automated monitoring of the growth vial. Monitoring may be periodic or continuous. This may take, for example, around 900 minutes (estimated), although the exact time depends upon detection of the desired OD.

In some implementations, after growing the cells to the desired OD, an inducer is added to the first growth module 1002 for inducing the cells. In a particular example, 100 µl of inducer may be added, and the growth module 1002 may bring the temperature of the mixture up to 42° C. and hold for 15 minutes.

The cell stock 1012, after growth and induction, is transferred to the first filtration module 1004, in some implementations, for rendering the cells electrocompetent (1020a) and to reduce the volume of the cells for transformation. In one example, a robotic handling system moves the vial of the cell stock 1012 from the rotating growth vial of the first growth module 1002 to a vial holder of the first filtration module 1004. In another example, the robotic handling system pipettes cell stock 1012 from the rotating growth vial of the first growth module 1002 and delivers it to the first filtration module 1004. For example, the disposable pipetting tip used to transfer the cell stock 1012 to the first growth module 1002 may be used to transfer the cell stock 1012 from the first growth module 1002 to the first filtration module 1004. In some embodiments, prior to transferring the cell stock 1012 from the first growth module 1002 to the first filtration module 1004, the first growth module 1002 is cooled to 4° C. so that the cell stock 1012 is similarly reduced to this temperature. In a particular example, the temperature of the first growth module 1002 may be reduced to about 4° C. over the span of about 8 minutes, and the growth module 1002 may hold the temperature at 4° C. for about 15 minutes to ensure reduction in temperature of the cell stock 1012.

Prior to transferring the cell stock, in some implementations, a filter of the first filtration module 1004 is pre-washed using a wash solution. The wash solution, for example, may be supplied in a wash cartridge, such as the cartridge 1006 described in relation to FIG. 1A. The first filtration module 1004, for example, may be fluidly connected to the wash solution of the wash cartridge, as described in relation to FIG. 7A.

The first filtration module 1004, for example, may be part of a dual filtration module such as the filtration module 750 described in relation to FIGS. 7B and 7C. In a particular example, the first filtration module 1004 may be maintained at 4° C. during the washing and eluting process while transferring cell materials between an elution vial and the first filtration module 1004.

In some implementations, upon rendering the cells electrocompetent at the filtration module 1004, the cell stock 1012 is transferred to a transformation module 1006 (e.g., flow-through electroporation module) for transformation. In one example, a robotic handling system moves the vial of the cell stock 1012 from the vial holder of the first filtration module 1004 to a reservoir of the flow-through electroporation module 1006. In another example, the robotic handling system pipettes cell stock 1012 from the first filtration module 1002 or a temporary reservoir and delivers it to the first filtration module 1004. In a particular example, 400 µl of the concentrated cell stock 1012 from the first filtration module 1004 is transferred to a mixing reservoir prior to transfer to the transformation module 1006. For example, the cell stock 1012 may be transferred to a reservoir in a cartridge for mixing with the assembled nucleic acids, then transferred by the robotic handling system using a pipette tip. In a particular example, the transformation module is maintained at 4° C. The cell stock 1012 may be transformed, in an illustrative example, in about four minutes.

While the cells are growing and/or rendered electrocompetent, in some implementations, a first oligo library 1014a and the sgRNA backbone 1016a are assembled using an isothermal nucleic acid assembly process to create assembled nucleic acids in an isothermal nucleic acid assembly master mix (1022a). The assembled nucleic acids may be created at some point during the first processing steps 1018a, 1020a of the first stage of the workflow 1000. Alternatively, assembled nucleic acids may be created in advance of beginning the first processing step 1018.

In some embodiments, the nucleic acids are assembled using an isothermal nucleic acid assembly module of the automated multi-module cell processing instrument. For example, the robotic handling system may add the first oligo library 1014a and the sgRNA backbone 1016a from a library vessel in the reagent cartridge in the automated multi-module cell processing instrument to an isothermal nucleic acid assembly module (not illustrated), such as the nucleic acid assembly module 1210g described in relation to FIG. 12B. The nucleic acid assembly mix, for example, may include in a particular example 50 µl Gibson Assembly® Master Mix, 25 µl vector backbone 1016a, and 25 µl oligo 1014a. The isothermal nucleic acid assembly module may be held at room temperature. The assembly process may take about 30 minutes.

In other embodiments, the nucleic acids are assembled externally to the multi-module cell processing instrument and added as a source material. For example, a vial or tube of assembled nucleic acids may be added to a reagent cartridge prior to activating the first step 1018a of cell processing. In a particular example, 100 µl of assembled nucleic acids are provided.

In some implementations, the assembled nucleic acids are purified (1024a). The assembled nucleic acids, for example, may be transferred by the robotic handling system from the isothermal nucleic acid assembly module to a purification module (not shown), such as the purification module 1210h of FIG. 12B. In other embodiments, the isothermal nucleic acid assembly module may include purification features (e.g., a combination isothermal nucleic acid assembly and purification module). In further embodiments, the assembled nucleic acids are purified externally to the multi-module cell processing instrument and added as a source material. For example, a vial or tube of purified assembled nucleic acids may be added to a reagent cartridge with the cell stock 1012 prior to activating the first step 1018a of cell processing.

In a particular example, 100 µl of assembled nucleic acids in isothermal nucleic acid assembly mix are purified. In some embodiments, magnetic beads are added to the isothermal nucleic acid assembly module, for example 180 µl of magnetic beads in a liquid suspension may be added to the isothermal nucleic acid assembly module by the robotic handling system. A magnet functionally coupled to the isothermal nucleic acid assembly module may be activated and the sample washed in 200 µl ethanol (e.g., the robotic handling system may transfer ethanol to the isothermal nucleic acid assembly module). Liquid waste from this operation, in some embodiments, is transferred to a waste receptacle of the cartridge (e.g., by the robotic handling system using a same pipette tip as used in transferring the ethanol). At this point, the de-salted assembled nucleic acids may be transferred to a holding container, such as a reservoir of the cartridge. The desalted assembled nucleic acids may be held, for example at a temperature of 4° C. until cells are ready for transformation. In a particular example, 100 µl of the assembled nucleic acids may be added to the 400 µl of the concentrated cell stock 1012 in the mixing reservoir prior to transfer to the transformation module 1006. In some embodiments, the purification process may take about 16 minutes.

In some implementations, the assembled nucleic acids and cell stock 1012 are added to the flow-through electroporation module 1006 and the cell stock 1012 is transformed (1026a). The robotic handling system, for example, may transfer the mixture of the cell stock 1012 and assembled nucleic acids to the flow-through electroporation module 1006 from a mixing reservoir, e.g., using a pipette tip or through transferring a vial or tube. In some embodiments, a built-in flow-through electroporation module such as the flow-through electroporation modules 500 of FIG. 5A is used to transform the cell stock 1012. In other embodiments, a cartridge-based electroporation module such as the flow-through electroporation module 530 of FIG. 5B is used to transform the cell stock 1012. The electroporation module 1006, for example, may be held at a temperature of 4° C. The electroporation process, in an illustrative example, may take about four minutes.

The transformed cell stock 1012, in some implementations, is transferred to the second growth module 1008 for recovery (1028a). In a particular example, transformed cells undergo a recovery process in the second growth module 1008 at a temperature of 30° C. The transformed cells, for example, may be maintained in the second growth module 1008 for about an hour for recovery.

In some implementations, a selective medium is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C.

After recovery, the cells may be ready for either another round of editing or for storage in a vessel, e.g., for further experiments conducted outside of the automated cell processing environment. Alternatively, a portion of the cells may be transferred to a storage unit as cell library output, while another portion of the cells may be prepared for a second round of editing.

In some implementations, in preparation for a second round of editing, the transformed cells are transferred to the second filtration module 1010 for media exchange and filtering (1030a). Prior to transferring the transformed cell stock, in some implementations, a filter of the second filtration module 1004 is pre-washed using a wash solution. The wash solution, for example, may be supplied in a wash cartridge, such as the cartridge 1006 described in relation to FIG. 1A. The second filtration module 1010, for example, may be fluidly connected to the wash solution of the wash cartridge, as described in relation to FIG. 7A.

The second filtration module 1010, for example, may be part of a dual filtration module such as the filtration module 750 described in relation to FIGS. 7B and 7C. In a particular example, the second filtration module 1010 may be maintained at 4° C. during the washing and eluting process while transferring cell materials between an elution vial and the second filtration module 1010. The output of this filtration process, in a particular example, is deposited in a vial or tube to await further processing, e.g., transfer to a transformation module. The vial or tube may be maintained in a storage unit at a temperature of 4° C.

The first stage of processing may take place during a single day. In an illustrative embodiment, the first stage of processing is estimated to take under 19 hours to complete (e.g., about 18.7 hours). At this point in the workflow 1000, in some implementations, new materials are manually added to the automated multi-module cell processing instrument. For example, a new reagent cartridge may be added. Further, a new wash cartridge, replacement filters, and/or replacement pipette tips may be added to the automated multi-module cell processing instrument at this point. Further, in some embodiments, the filter module may undergo a cleaning process and/or the solid and liquid waste units may be emptied in preparation for the next round of processing. In yet other embodiments, the reagent cartridges may provide reagents for two or more cycles of editing.

In some implementations, the second round of editing involves the same modules 1002, 104, 1006, 1008, and 1010, the same processing steps 1018, 1020, 1022, 1024, 1026, 1028, and 1030, and the same temperature and time ranges as the first processing stage described above. For example, the second oligo library 1014b and the second sgRNA backbone 1016b may be used to edit the transformed cells in much the same manner as described above. Although illustrated as a two-stage process, in other embodiments, up to two, four, six, eight, or more recursions may be conducted to continue to edit the same cell stock 1012.

In other implementations, turning to FIG. 10B, a workflow 1040 involves the same modules 1002, 1004, 1006, 1008, and 1010 as well as the same processing steps 1018, 1020, 1022, 1024, 1026, 1028, and 1030 for the first stage of process. However, unlike the workflow 1000 of FIG. 10A, a second stage of the workflow 1040 of FIG. 10B involves a curing steps. "Curing" is a process in which a vector—for example the editing vector used in the prior round of editing, the "engine" vector comprising the expression sequence for the nuclease, or both—are eliminated from the transformed cells. Curing can be accomplished by, e.g., cleaving the editing vector using a curing plasmid thereby rendering the editing and/or engine vector nonfunctional (exemplified in the workflow of FIG. 10b); diluting the vector in the cell population via cell growth (that is, the more growth cycles the cells go through, the fewer daughter cells will retain the editing or engine vector(s)) (not shown), or by, e.g., utilizing a heat-sensitive origin of replication on the editing or engine vector (not shown). In one example, a "curing plasmid" may be contained within the reagent cartridge of the automated instrument, or added manually to the instrument prior to the second stage of processing. As with the workflow 1000, in some embodiments, the workflow 1040 is performed based upon a script executed by a processing system of the automated multi-module cell processing instrument, such as the processing system 1310 of FIG. 13. The script, in a first example, may be accessed via a machine-readable marker or tag added to the first cartridge. In some embodiments, each processing stage is performed using a separate script. For example, each cartridge may include an indication of a script or a script itself for processing the contents of the cartridge. In this manner, for example, the second stage, involving the curing cartridge, may be performed using a script designed for the settings (e.g., temperatures, times, material quantities, etc.) appropriate for curing. The conditions for curing will depend on the mechanism used for curing; that is, in this example, how the curing plasmid cleaves the editing and/or engine plasmid.

In some implementations, the second stage of the workflow 1040 begins by receiving first-edited cells from the first stage of the workflow 1040 at the first growth module 1002. For example, the first-edited cells may have been edited using a cell stock 1042, an oligo library 1044, and an sgRNA backbone 1046 through applying the steps 1018, 1020, 1022, 1024, 1026, 1028, and 1030 as described in relation to the workflow 1000 of FIG. 10A. The first-edited cell stock 1042, for example, may be transferred to the first growth module 1002 by a robotic handling system. In one example, a robotic handling system adds a vial of the first-edited cell stock 1042 to a rotating growth vial of the first growth module 1002. In another example, the robotic handling system pipettes first-edited cell stock 1042 from a receptacle of a storage unit and adds the cell stock 1042 to the rotating growth vial. The cells may have been maintained at a temperature of 4° C. at this point.

In some implementations, the first-edited cells are inoculated, grown, and monitored in the first growth module 1002 (1018d). In a particular example, an aliquot of the first-edited cell stock 1042 may be transferred to a rotating growth vial containing, e.g., 20 mL of growth medium at a temperature of 30° C. to an OD of 0.50. The cell stock 1042 added to the first growth module 1002 may be monitored over time until 0.50 OD is sensed via the automated monitoring. Monitoring may be periodic or continuous. This may take, for example, around 900 minutes (estimated), although the exact time depends upon detection of the desired OD.

In some implementations, after growing to the desired OD, an inducer is added to the first growth module 1002 for inducing the cells. In a particular example, 100 µl of inducer may be added, and the growth module 1002 may bring the temperature of the mixture up to 42° C. and hold for 15 minutes.

The first-edited cell stock 1042, after growth and induction, is transferred to the first filtration module 1004, in some implementations, for rendering the first-edited cells electrocompetent (1020d). In one example, a robotic handling system moves the vial of the first-edited cell stock 1042 from the rotating growth vial of the first growth module 1002 to a vial holder of the first filtration module 1004. In another example, the robotic handling system pipettes first-edited cell stock 1042 from the rotating growth vial of the first growth module 1002 and delivers it to the first filtration module 1004. For example, the disposable pipetting tip used to transfer the first-edited cell stock 1042 to the first growth module 1002 may be used to transfer the cell stock 1042 from the first growth module 1002 to the first filtration module 1004. In some embodiments, prior to transferring the cell stock 1042 from the first growth module 1002 to the first filtration module 1004, the first growth module 1002 is cooled to 4° C. so that the cell stock 1042 is similarly reduced to this temperature. In a particular example, the temperature of the first growth module 1002 may be reduced to about 4° C. over the span of about 8 minutes, and the growth module 1002 may hold the temperature at 4° C. for about 15 minutes to ensure reduction in temperature of the cell stock 1012.

Prior to transferring the first-edited cell stock 1042 to the filtration module, in some implementations a filter of the first filtration module 1004 is pre-washed using a wash solution. The wash solution, for example, may be supplied in a wash cartridge, such as the cartridge 1006 described in relation to FIG. 1A. The first filtration module 1004, for example, may be fluidly connected to the wash solution of the wash cartridge, as described in relation to FIG. 7A.

The first filtration module 1004, for example, may be part of a dual filtration module such as the filtration module 750 described in relation to FIGS. 7B and 7C. In a particular example, the first filtration module 1004 may be maintained at 4° C. during the washing and eluting process while transferring cell materials between an elution vial and the first filtration module 1004.

In some implementations, upon rendering the first-edited cells electrocompetent at the filtration module 1004 (1020*d*), the first-edited cell stock 1042 is transferred to a transformation module 1006 (e.g., flow-through electroporation module) for transformation. In one example, a robotic handling system moves the vial of the cell stock 1042 from the vial holder of the first filtration module 1004 to a reservoir of the flow-through electroporation module 1006. In another example, the robotic handling system pipettes cell stock 1042 from the first filtration module 1002 or a temporary reservoir and delivers it to the first filtration module 1004. In a particular example, 400 μl of the concentrated cell stock 1042 from the first filtration module 1004 is transferred to a mixing reservoir prior to transfer to the transformation module 1006. For example, the cell stock 1042 may be transferred to a reservoir in a cartridge for mixing with a curing plasmid 1050, then mixed and transferred by the robotic handling system using a pipette tip. In a particular example, the transformation module 1006 is maintained at 4° C. The cell stock 1042 may be transformed, in an illustrative example, in about four minutes.

The transformed cell stock 1042, in some implementations, is transferred to the second growth module 1008 for recovery/curing (1028*d*). In a particular example 20 ml of transformed cells undergo a recovery process in the second growth module 1008 at a temperature of 30° C. The transformed cells, for example, may be maintained in the second growth module 1008 for about an hour for recovery. If another round of editing is desired, the first editing plasmid or vector is cured. If another round of editing is not desired, the first editing plasmid and the engine plasmid may be cured.

After recovery and curing, the cells may be ready for either another round of editing or for storage to be used in further research outside the automated cell processing instrument. For example, a portion of the cells may be transferred to a storage unit as cell library output, while another portion of the cells may be prepared for a second round of editing.

In some implementations, in preparation for a second round of editing, the transformed cells are transferred to the second filtration module 1010 for media exchange and filtering (1030*d*) containing glycerol for rendering the cells electrocompetent. Prior to transferring the transformed cell stock, in some implementations, a filter of the second filtration module 1004 is pre-washed using a wash solution. The wash solution, for example, may be supplied in a wash cartridge, such as the cartridge 1006 described in relation to FIG. 1A. The second filtration module 1010, for example, may be fluidly connected to the wash solution of the wash cartridge, as described in relation to FIG. 7A.

The second filtration module 1010, for example, may be part of a dual filtration module such as the filtration module 750 described in relation to FIGS. 7B and 7C. In a particular example, the second filtration module 1010 may be maintained at 4° C. during the washing and eluting process while transferring cell materials between an elution vial and the second filtration module 1010. The output of this filtration process, in a particular example, are electrocompetent cells deposited in a vial or tube to await further processing. The vial or tube may be maintained in a storage unit at a temperature of 4° C.

Turning to FIG. 10C, a flow diagram illustrates a yeast workflow 1060 involving two stages of processing having identical processing steps, resulting in two edits to a cell stock 1062. Each stage may operate based upon a different cartridge of source materials. For example, a first cartridge may include a first oligo library 1070*a* and a first sgRNA back bone 1072*a*. A second cartridge, introduced into the automated multi-module cell processing instrument between processing stages or prior to processing but in a different position than the first cartridge, may include a second oligo library 1070*b* and a second sgRNA back bone 1072*b*. Each cartridge may be considered as a "library cartridge" for building a library of edited cells. Alternatively, a user may add a container (e.g., vial or tube of the cell stock 1062*a* to each of the purchased cartridges included in a yeast cell kit.

The workflow 1060, in some embodiments, is performed based upon a script executed by a processing system of the automated multi-module cell processing system, such as the processing system 1310 of FIG. 13. The script, in a first example, may be accessed via a machine-readable marker or tag added to the first cartridge. In some embodiments, each processing stage is performed using a separate script. For example, each cartridge may include an indication of a script or a script itself for processing the contents of the cartridge.

In some implementations, the first stage begins with introducing the cell stock 1062 into the first growth module 1002 for inoculation, growth, and monitoring (1018*e*). In one example, a robotic handling system adds a vial of the cell stock 1062 to a rotating growth vial of the first growth module 1002. In another example, the robotic handling system pipettes cell stock 1062 from the first cartridge and adds the cell stock 1062 to the rotating growth vial. The cells may have been maintained at a temperature of 4° C. at this point. In a particular example, 20 ml of cell stock may be grown within a rotating growth vial of the first growth module 1002 at a temperature of 30° C. to an OD of 0.75. The cell stock 1012 added to the first growth module 1002 may be automatically monitored over time within the growth module 1002 until 0.75 OD is sensed via the automated monitoring. Monitoring may be periodic or continuous.

In some implementations, an inducible expression system may be used. Thus, after growing to the desired OD, an inducer is added to the first growth module 1002 for inducing the cells. The inducer could be a small molecule or a media exchange to a medium with a different sugar like galactose.

The cell stock 1062, after growth and induction, is transferred to the first filtration module 1004, in some implementations, for exchanging media (1064*a*). In one example, a robotic handling system moves the vial of the cell stock 1062 from the rotating growth vial of the first growth module 1002 to a vial holder of the first filtration module 1004. In another example, the robotic handling system pipettes cell stock 1062 from the rotating growth vial of the first growth module 1002 and delivers it to the first filtration module 1004. For example, the disposable pipetting tip used to transfer the cell stock 1062*a* to the first growth module 1002 may be used to transfer the cell stock 1062 from the first growth module 1002 to the first filtration module 1004. In some embodiments, prior to transferring the cell stock 1062 from the first growth module 1002 to the first filtration module 1004, the first growth module 1002 is cooled to 4° C. so that the cell stock 1062 is similarly reduced to this temperature. In a particular example, the temperature of the first growth module 1002 may be reduced to about 4° C. over the span of about 8 minutes, and the growth module 1002 may hold the temperature at 4° C. for about 15 minutes to ensure reduction in temperature of the cell stock 1062. During media exchange, in an illustrative example, 0.4 ml of 1M sorbitol may be added to the cell stock 1062.

Prior to transferring the cell stock 1062, in some implementations, a filter of the first filtration module 1004 is pre-washed using a wash solution. The wash solution, for example, may be supplied in a wash cartridge, such as the cartridge 1006 described in relation to FIG. 1A. The first filtration module 1004, for example, may be fluidly connected to the wash solution of the wash cartridge, as described in relation to FIG. 7A.

The first filtration module 1004, for example, may be part of a dual filtration module such as the filtration module 750 described in relation to FIGS. 7B and 7C. In a particular example, the first filtration module 1004 may be maintained at 4° C. during the washing and eluting process while transferring cell materials between an elution vial and the first filtration module 1004.

After the media exchange operation, in some implementations, the cell stock 1062 is transferred back to the first growth module 1002 for conditioning (1066*a*). In one example, a robotic handling system moves the vial of the cell stock 1062 from the first filtration module 1004 to the first growth module 1002. In another example, the robotic handling system pipettes cell stock 1062 from the first filtration module 1004 and delivers it to the rotating growth vial of the first growth module 1002. During conditioning, for example, 5 ml DTT/LIAc and 80 mM of Sorbitol may be added to the cell stock 1062. For example, the robotic handling system may transfer the DTT/LIAc and Sorbitol, individually or concurrently, to the first growth module 1002. The cell stock 1062 may be mixed with the DTT/LIAc and Sorbitol, for example, via the rotation of the rotating growth vial of the first growth module 1002. During conditioning, the cell stock 1062 may be maintained at a temperature of 4° C.

In some implementations, after conditioning, the cell stock 1062 is transferred to the first filtration module 1004 for washing and preparing the cells (1068). For example, the cells may be rendered electrocompetent at this step. In one example, a robotic handling system moves the vial of the cell stock 1062 from the rotating growth vial of the first growth module 1002 to a vial holder of the first filtration module 1004. In another example, the robotic handling system pipettes cell stock 1062 from the rotating growth vial of the first growth module 1002 and delivers it to the first filtration module 1004.

Prior to transferring the cell stock, in some implementations, a filter of the first filtration module 1004 is pre-washed using a wash solution. The wash solution, for example, may be supplied in a wash cartridge, such as the cartridge 1006 described in relation to FIG. 1A. The first filtration module 1004, for example, may be fluidly connected to the wash solution of the wash cartridge, as described in relation to FIG. 7A. In other embodiments, the same filter is used for rendering electrocompetent as the filter used for media exchange at step 1064*a*. In some embodiments, 1M sorbitol is used to render the yeast cells electrocompetent.

In some implementations, upon rendering electrocompetent at the filtration module 1004, the cell stock 1062 is transferred to a transformation module 1006 (e.g., flow-through electroporation module) for transformation. In one example, a robotic handling system moves the vial of the cell stock 1062 from the vial holder of the first filtration module 1004 to a reservoir of the flow-through electroporation module 1006. In another example, the robotic handling system pipettes cell stock 1062 from the filtration module 1004 or a temporary reservoir and delivers it to the first filtration module 1004. In a particular example, 400 µl of the concentrated cell stock 1062 from the first filtration module 1004 is transferred to a mixing reservoir prior to transfer to the transformation module 1006. For example, the cell stock 1062 may be transferred to a reservoir in a cartridge for mixing with the nucleic acid components (backbone and editing oligonucleotide), then mixed and transferred by the robotic handling system using a pipette tip. Because the backbone (vector) and editing oligonucleotide are assembled in the cells (in vivo), a nucleic acid assembly module is not a necessary component for yeast editing. In a particular example, the transformation module is maintained at 4° C.

In some implementations, the nucleic acids to be assembled and the cell stock 1062 is added to the flow-through electroporation module 1006 and the cell stock 1062 is transformed (1026*e*). The robotic handling system, for example, may transfer the mixture of the cell stock 1062*e* and nucleic acid assembly to the flow-through electroporation module 1006 from a mixing reservoir, e.g., using a pipette tip or through transferring a vial or tube. In some embodiments, a built-in flow-through electroporation module such as the flow-through electroporation modules 500 of FIG. 5A is used to transform the cell stock 1062*e*. In other embodiments, a cartridge-based electroporation module such as the flow-through electroporation module 530 of FIG. 5B is used to transform the cell stock 1062*e*. The electroporation module 1006, for example, may be held at a temperature of 4° C.

The transformed cell stock 1062*e*, in some implementations, is transferred to the second growth module 1008 for recovery (1028*a*). In a particular example, 20 ml of transformed cells undergo a recovery process in the second growth module 1008.

In some implementations, a selective medium, e.g. an auxotrophic growth medium or a medium containing a drug, is transferred to the second growth vial (not illustrated), and the cells are left to incubate for a further period of time in a selection process. In an illustrative example, an antibiotic may be transferred to the second growth vial, and the cells may incubate for an additional two hours at a temperature of 30° C.

After recovery, the cells may be ready for either another round of editing or for storage in a cell library. For example, a portion of the cells may be transferred to a storage unit as cell library output (1076*a*), while another portion of the cells may be prepared for a second round of editing (1078*a*). The cells may be stored, for example, at a temperature of 4° C.

In some implementations, in preparation for a second round of editing, the transformed cells are transferred to the second filtration module 1010 for media exchange (1078*a*). Prior to transferring the transformed cell stock 1062*a*, in some implementations, a filter of the second filtration module 1004 is pre-washed using a wash solution. The wash solution, for example, may be supplied in a wash cartridge, such as the cartridge 1006 described in relation to FIG. 1A. The second filtration module 1010, for example, may be fluidly connected to the wash solution of the wash cartridge, as described in relation to FIG. 7A.

The second filtration module 1010, for example, may be part of a dual filtration module such as the filtration module 750 described in relation to FIGS. 7B and 7C. In a particular example, the second filtration module 1010 may be maintained at 4° C. during the washing and eluting process while transferring cell materials between an elution vial and the second filtration module 1010.

In some implementations during the filtration process, an enzymatic preparation is added to lyse the cell walls of the cell stock 1062a. For example, a yeast lytic enzyme such as Zylomase® may be added to lyse the cell walls. The yeast lytic enzyme, in a particular example, may be incubated in the cell stock 1026a for between 5-60 minutes at a temperature of 30° C. The output of this filtration process, in a particular example, is deposited in a vial or tube to await further processing. The vial or tube may be maintained in a storage unit at a temperature of 4° C.

The first stage of processing may take place during a single day. At this point of the workflow 1060, in some implementations, new materials are manually added to the automated multi-module cell processing instrument. For example, new cell stock 1062b and a new reagent cartridge may be added. Further, a new wash cartridge, replacement filters, and/or replacement pipette tips may be added to the automated multi-module cell processing system at this point. Further, in some embodiments, the filter module may undergo a cleaning process and/or the solid and liquid waste units may be emptied in preparation for the next round of processing.

In some implementations, the second round of editing involves the same modules 1002, 104, 1006, 1008, and 1010, the same processing steps 1018, 1064, 1066, 1026, 1028, and 1076 and/or 1078, and the same conditions (e.g., temperatures, time ranges, etc.) as the first processing stage described above. For example, the second oligo library 1070b and the second sgRNA backbone 1072b may be used to edit a combination of the transformed cells in much the same manner as described above. Although illustrated as a two-stage process, in other embodiments, up to two, three, four, six, eight, or more recursions may be conducted to continue to edit the cell stock 1062.

Example I: Fully-Automated Singleplex RGN-directed Editing Run

Singleplex automated genomic editing using MAD7 nuclease was successfully performed with an automated multi-module instrument of the disclosure. See U.S. Pat. No. 9,982,279.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. Coli* cells were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example II: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a transformation module for electroporation. The transformation module comprised an ADP-EPC cuvette. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

Alternative Embodiments of Instrument Architecture

FIGS. 12A and 12B illustrate example alternative embodiments of automated multi-module cell editing instruments for performing automated cell processing, e.g., editing in multiple cells in a single cycle. The automated multi-module cell editing instruments, for example, may be desktop instruments designed for use within a laboratory environment. The automated multi-module cell editing instruments may incorporate a mixture of reusable and disposable elements for performing various staged operations in conducting automated genome cleavage and/or editing in cells.

FIG. 12A is a block diagram of a first example instrument 1200 for performing automated cell processing, e.g., editing in multiple cells in a single cycle according to one embodiment of the disclosure. In some implementations, the instrument 1200 includes a deck 1202, a reagent supply receptacle 1204 for introducing DNA sample components to the instrument 1200, a cell supply receptacle 1206 for introducing cells to the instrument 1200, and a robot handling system 1208 for moving materials between modules (for example, modules 1210a, 1210b, 1210c, 1210d) receptacles (for example, receptacles 1204 1206, 1212, 1222, 1224, and 1226), and storage units (e.g., units 1216, 1218, 1228, and 1214) of the instrument 1200 to perform the automated cell processing. Upon completion of processing of the cell supply 1206, in some embodiments, cell output 1212 may be transferred by the robot handling system 1208 to a storage unit 1214 for temporary storage and later retrieval.

The robotic handling system 1208, for example, may include an air displacement pump to transfer liquids from the various material sources to the various modules 1210 and storage unit 1214. In other embodiments, the robotic handling system 1208 may include a pick and place head to transfer containers of source materials (e.g., tubes) from a supply cartridge (not illustrated, discussed in relation to FIG. 1A) to the various modules 1210. In some embodiments, one or more cameras or other optical sensors (not shown), confirm proper gantry movement and position.

In some embodiments, the robotic handling system 1208 uses disposable transfer tips provided in a transfer tip supply 1216 to transfer source materials, reagent 1204 (e.g., nucleic acid assembly), and cells 1206 within the instrument 1200. Used transfer tips 1216, for example, may be discarded in a solid waste unit 1218. In some implementations, the solid waste unit 1218 contains a kicker to remove tubes from the pick and place head of robotic handling system 1208.

In some embodiments, the instrument 1200 includes electroporator cuvettes with sippers that connect to an air displacement pump. In some implementations, cells 1206 and reagent 1204 are aspirated into the electroporation cuvette through a sipper, and the cuvette is moved to one or more modules 1210 of the instrument 1200.

In some implementations, the instrument 1200 is controlled by a processing system 1220 such as the processing system 1310 of FIG. 13. The processing system 1220 may be configured to operate the instrument 100 based on user input. The processing system 1220 may control the timing, duration, temperature and other operations of the various modules 1210 of the instrument 1200. The processing system 1220 may be connected to a power source (not shown) for the operation of the instrument 1200.

In some embodiments, instrument 1200 includes a transformation module 1210c for introduction of, e.g., in the context of editing, nucleic acid(s) into the cells 1206. For example, the robotic handling system 1208 may transfer the reagent 1204 and cells 1206 to the transformation module 1210c. The transformation module 1210 may conduct any cell transformation or transfection techniques routinely used by those of skill in the arts of transfection, transformation and microfluidics. Transformation is intended to include to a variety of art-recognized techniques for introducing an exogenous nucleic acid sequence (e.g., DNA) into a target cell, including those transformation and transfection techniques. Such methods include, but are not limited to, electroporation, lipofection, optoporation, injection, microprecipitation, liposomes, particle bombardment, sonoporation, laser-induced poration, bead transfection, calcium phosphate or calcium chloride co-precipitation, or DEAE-dextran-mediated transfection. Transformation can take place in microfuge tubes, test tubes, cuvettes, multi-well plates, microfibers, or flow instrument s. The processing system 1220 may control temperature and operation of the transformation module 1210c. In some implementations, the processing system 1270 effects operation of the transformation module 1210c according to one or more variable controls set by a user.

In some implementations, the transformation module 1210c is configured to prepare cells for vector uptake by increasing cell competence with a pretreatment solution, 1222, e.g., a sucrose or glycerol wash. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, Molecular Cloning: A Laboratory Manual, 4th, ed., Cold Spring Harbor Laboratory Press, Cold Spring Harbor, N.Y., 2014), and other laboratory manuals.

Following transformation, in some implementations, the cells may be transferred to a recovery module 1210d. In some embodiments, the recovery module 1210d is a combination recovery and induction of editing module. In the recovery module 1210d, the cells may be allowed to recover, express the nucleic acids and, in an inducible nuclease system, a nuclease is introduced to the cells, e.g., by means of temporally-controlled induction such as, in some examples, chemical, light, viral, or temperature induction or the introduction of an inducer molecule 1224 for expression of the nuclease.

Following editing, in some implementations, the cells are transferred to the storage unit 1214, where the cells can be stored as cell output 1212 until the cells are removed for further study or retrieval of an edited cell population, e.g., an edited cell library.

In some implementations the instrument 1200 is designed for recursive genome editing, where multiple edits are sequentially introduced into genomes inside the cells of a cell population. In some implementations, the reagent supply 1204 is replenished prior to accessing cell output 1212 from the storage unit for recursive processing. In other implementations, multiple reagent supplies 1204 and/or large volumes thereof may be introduced into the instrument 1200 such that user interaction is not necessarily required prior to a subsequent processing cycle.

A portion of a cell output 1212a, in some embodiments, is transferred to an automated cell growth module 1210a. For example, all of the cell output 1212a may be transferred, or a only an aliquot may be transferred such that the instrument retains incrementally modified samples. The cell growth module 1210a, in some implementations, measures the OD of the cells during growth to ensure they are at a desired concentration prior to induction of editing. Other measures of cell density and physiological state that can be used include but are not limited to, pH, dissolved oxygen, released enzymes, acoustic properties, and electrical properties.

To reduce the background of cells that have not received a genome edit, in some embodiments, the growth module 1210a performs a selection process to enrich for the edited cells using a selective growth medium 1226. For example, the introduced nucleic acid can include a gene that confers antibiotic resistance or another selectable marker. In some implementations, multiple selective genes or markers 1226 may be introduced into the cells during recursive editing. For example, alternating the introduction of selectable markers for sequential rounds of editing can eliminate the background of unedited cells and allow multiple cycles of the instrument 1200 to select for cells having sequential genome edits. Suitable antibiotic resistance genes include, but are not limited to, genes such as ampicillin-resistance gene, tetracycline-resistance gene, kanamycin-resistance gene, neomycin-resistance gene, canavanine-resistance gene, blasticidin-resistance gene, hygromycin-resistance gene, puromycin-resistance gene, and chloramphenicol-resistance gene.

From the growth module 1210a, the cells may be transferred to a filtration module 110b. The filtration module 1210b or, alternatively, a cell wash and concentration module, may enable media exchange. In some embodiments, removing dead cell background is aided using lytic enhancers such as detergents, osmotic stress, temperature, enzymes, proteases, bacteriophage, reducing agents, or chaotropes. In other embodiments, cell removal and/or media exchange is used to reduce dead cell background. Waste product from the filtration module 1210b, in some embodiments, is collected in a liquid waste unit 1228.

After filtration, the cells may be presented to the transformation module 1210c, and then to the recovery module 1210d and finally to the storage unit 1214 as detailed above.

Turning to FIG. 12B, similar to FIG. 12A, a second example instrument 1240 for performing automated genome cleavage and/or editing in multiple cells in a single cycle includes the deck 1202, the reagent supply receptacle 1204 for introducing one or more nucleic acid components to the instrument 1240, the cell supply receptacle 1206 for introducing cells to the instrument 1240, and the robot handling system 1208 for moving materials between modules (for example, modules 1210a, 1210b, 1210c, 1210f 1210g, 1210m, and 1210h), receptacles (for example, receptacles 1204 1206, 1212, 1214, 1224, 1242, 1244, and 1246), and storage units (e.g., units 1214, 1216, 1218, and 1228) of the instrument 1240 to perform the automated cell processing. Upon completion of processing of the cell supply 1206, in some embodiments, cell output 1212 may be transferred by the robot handling system 1208 to the storage unit 1214 for temporary storage and later retrieval.

In some embodiments, the robotic handling system 1208 uses disposable transfer tips provided in the transfer tip supply 1216 to transfer source materials, a vector backbone 1242, editing oligos 1244, reagents 1204 (e.g., for nucleic acid assembly, nucleic acid purification, to render cells electrocompetent, etc.), and cells 1206 within the instrument 1240, as described in relation to FIG. 12A.

In other embodiments, the instrument 1240 includes electroporator cuvettes with sippers that connect to an air displacement pump. In some implementations, the cells 1206 and the reagent 1204 are aspirated into the electroporation cuvette through a sipper, and the cuvette is moved to one or more modules 1210 of the instrument 1240.

As described in relation to FIG. 12A, in some implementations, the instrument 1240 is controlled by the processing system 1220 such as the processing system 1310 of FIG. 13.

The instrument 1240, in some embodiments, includes a nucleic acid assembly module 1210g, and in certain example automated multi-module cell processing instruments, the nucleic acid assembly module 1210g may include in some embodiments an isothermal nucleic acid assembly. As described above, the isothermal nucleic acid assembly module is configured to perform the Gibson Assembly® molecular cloning method.

In some embodiments, after assembly of the nucleic acids, the nucleic acids (e.g., in the example of an isothermal nucleic acid assembly, the isothermal nucleic acid assembly mix (nucleic acids+isothermal nucleic acid assembly reagents) are transferred to a purification module 1210h. Here, unwanted components of the nucleic acid assembly mixture are removed (e.g., salts, minerals) and, in certain embodiments, the assembled nucleic acids are concentrated. For example, in an illustrative embodiment, in the purification module 1210h, the isothermal nucleic acid assembly mix may be combined with a no-salt buffer and magnetic beads, such as Solid Phase Reversible Immobilization (SPRI) magnetic beads or AMPure beads. The isothermal nucleic acid assembly mix may be incubated for sufficient time (e.g., 30 seconds to 10 minutes) for the assembled nucleic acids to bind to the magnetic beads. In some embodiments, the purification module includes a magnet configured to engage the magnetic beads. The magnet may be engaged so that the supernatant may be removed from the bound assembled nucleic acids and so that the bound assembled nucleic acids can be washed with, e.g., 80% ethanol. Again, the magnet may be engaged and the 80% ethanol wash solution removed. The magnetic bead/assembled nucleic acids may be allowed to dry, then the assembled nucleic acids may be eluted and the magnet may again be engaged, this time to sequester the beads and to remove the supernatant that contains the eluted assembled nucleic acids. The assembled nucleic acids may then be transferred to the transformation module (e.g., electroporator in a preferred embodiment). The transformation module may already contain the electrocompetent cells upon transfer.

In some embodiments, instrument 1240 includes the transformation module 1210c for introduction of the nucleic acid(s) into the cells 1206, as described in relation to FIG. 12A. However, in this circumstance, the assembled nucleic acids 1204, output from the purification module 1210h, are transferred to the transformation module 1210c for combination with the cells 1206.

Following transformation in the transformation module 1210c, in some implementations, the cells may be transferred to a recovery module 1210m. In the recovery module 1210e, the cells may be allowed to recover, express the nucleic acids, and, in an inducible nuclease system, the nuclease is induced, e.g., by means of temporally-controlled induction such as, in some examples, chemical, light, viral, or temperature induction or the introduction of the inducer molecule for expression of the nuclease.

Following recovery, in some implementations, the cells are transferred to an editing module 1210f. The editing module 1210f supplies appropriate conditions to induce editing of the cells' genomes, e.g., through expression of the introduced nucleic acids and the induction of an inducible nuclease. The cells may include an inducible nuclease. The nuclease may be, in some examples, chemically induced, biologically induced (e.g., via inducible promoter) virally induced, light induced, temperature induced, and/or heat induced within the editing module 1210f.

Following editing, in some implementations, the cells are transferred to the storage unit 1214 as described in relation to FIG. 12A.

In some implementations, the instrument 1240 is designed for recursive genome editing, where multiple edits are sequentially introduced into genomes inside the cells of a cell population. In some implementations, the reagent supply 1204 is replenished prior to accessing cell output 1212 from the storage unit for recursive processing. For example, additional vector backbone 1242 and/or editing oligos 1244 may be introduced into the instrument 1240 for assembly and preparation via the nucleic acid assembly module 1210g and the purification module 1210h. In other implementations, multiple vector backbone volumes 1242 and/or editing oligos 1244 may be introduced into the instrument 140 such that user interaction is not necessarily required prior to a subsequent processing cycle. For each subsequent cycle, the vector backbone 1242 and/or editing oligos 1244 may change. Upon preparation of the nucleic acid assembly, the nucleic acid assembly may be provided in the reagent supply 1204 or another storage region.

A portion of a cell output 1212a, in some embodiments, is transferred to the automated cell growth module 1210a, as discussed in relation to FIG. 12A.

To reduce background of cells that have not received a genome edit, in some embodiments, the growth module 1210a performs a selection process to enrich for the edited cells using a selective growth medium 1226, as discussed in relation to FIG. 12A.

From the growth module 1210a, the cells may be transferred to the filtration module 1210b, as discussed in relation to FIG. 12A. As illustrated, eluant from an eluting supply 1246 (e.g. buffer, glycerol) may be transferred into the filtration module 1210b for media exchange.

After filtration, the cells may be presented to the transformation module 1210c for transformation, and then to the recovery module 110m and the editing module 1210f and finally to the storage unit 1214 as detailed above.

In some embodiments, the automated multi-module cell processing instruments of FIGS. 12A and/or 12B contain one or more replaceable supply cartridges and a robotic handling system, as discussed in relation to FIGS. 1A and 1B. Each cartridge may contain one or more of a nucleic acid assembly mix, oligonucleotides, vector, growth media, selection agent (e.g., antibiotics), inducing agent, nucleic acid purification reagents such as Solid Phase Reversible Immobilization (SPRI) beads, ethanol, and 10% glycerol.

Although the example instruments 1200, 1240 are illustrated as including a particular arrangement of modules 1210, these arrangements are for illustrative purposes only. For example, in other embodiments, more or fewer modules 1210 may be included within each of the instruments 1200, 1240. Also, different modules may be included in the instrument, such as, e.g., a module that facilitates cell fusion for providing, e.g., hybridomas, a module that amplifies nucleic acids before assembly, and/or a module that facilitates protein expression and/or secretion. Further, certain modules 1210 may be replicated within certain embodiments, such as the duplicate cell growth modules 110a, 110b of FIG. 1A. Each of the instruments 1200 and 1240, in another example, may be designed to accept a media cartridge such as the cartridges 104 and 106 of FIG. 1A. Further modifications are possible.

Control System for an Automated Multi-Module Cell Processing Instrument

Figure 11:
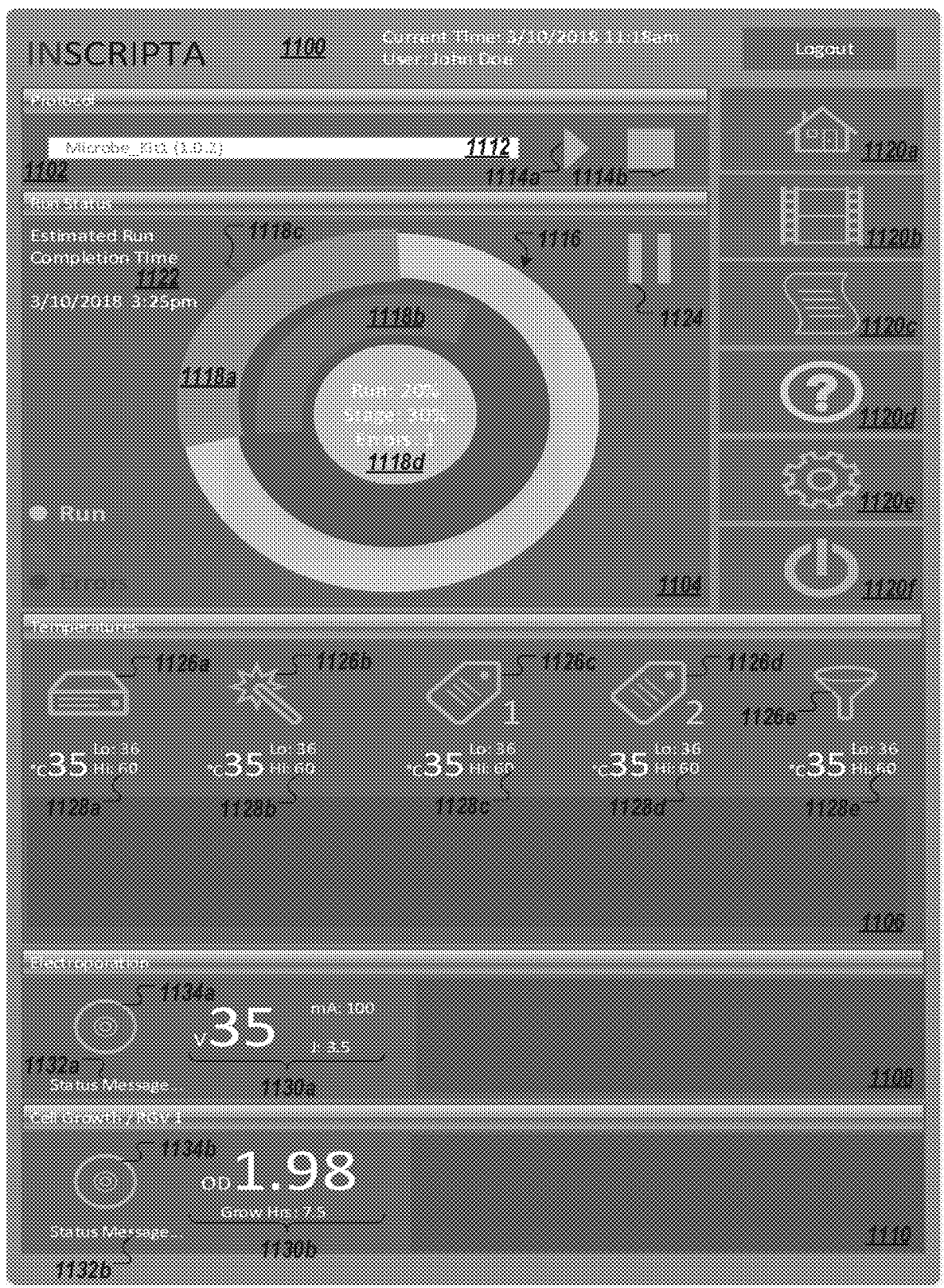
FIG. 11 illustrates an example graphical user interface for providing instructions to and receiving feedback from an automated multi-module cell processing instrument.

Turning to FIG. 11, a screen shot illustrates an example graphical user interface (GUI) 1100 for interfacing with an automated multi-module cell processing instrument. The interface, for example, may be presented on the display 236 of FIGS. 1C and 2D. In one example, the GUI 1100 may be presented by the processing system 1310 of FIG. 13 on the touch screen 1316.

In some implementations, the GUI 1100 is divided into a number of information and data entry panes, such as a protocol pane 1102, a temperature pane 1106, an electroporation pane 1108, and a cell growth pane 1110. Further panes are possible. For example, in some embodiments the GUI 1100 includes a pane for each module, such as, in some examples, one or more of each of a nucleic acid assembly module, a purification module, a cell growth module, a filtration module, a transformation module, an editing module, and a recovery module. The lower panes of the GUI 1100, in some embodiments, represent modules applicable to the present work flow (e.g, as selected in the protocol pane 1102 or as designated within a script loaded through a script interface (not illustrated)). In some embodiments, a scroll or paging feature may allow the user to access additional panes not illustrated within the screen shot of FIG. 11.

The GUI 1100, in some embodiments, includes a series of controls 1120 for accessing various screens such as the illustrated screen shot (e.g., through using a home control 1120a). For example, through selecting an editing control 1120b, the user may be provided the option to provide one, two or a series of cell processing steps. Through selecting a script control 1120c, the user may be provided the opportunity to add a new processing script or alter an existing processing script. The user in some embodiments, may select a help control 1120d to obtain further information regarding the features of the GUI 1100 and the automated multi-module cell processing instrument. In some implementations, the user selects a settings control 1120e to access settings options for desired processes and/or the GUI 1100 such as, in some examples, time zone, language, units, network access options. A power control 1120f, when selected, allows the user to power down the automated multi-module cell processing instrument.

Turning to the protocol pane 1102, in some implementations, a user selects a protocol (e.g., script or work flow) for execution by the automated multi-module cell processing instrument by entering the protocol in a protocol entry field 1112 (or, alternatively, drop-down menu). In other embodiments, the protocol may be selected through a separate user interface screen, accessed for example by selecting the script control 1120b. In another example, the automated multi-module cell processing instrument may select the protocol and present it in the protocol entry field 1112. For example, a processing system of the automated multi-module cell processing instrument may scan machine-readable indicia positioned on one or more cartridges loaded into the automated multi-module cell processing instrument to determine the appropriate protocol. As illustrated, the "Microbe_Kit1 (1.0.2)" protocol has been selected, which may correspond to a kit of cartridges and other disposable supplies purchased for use with the automated multi-module cell processing instrument.

In some implementations, the protocol pane 1102 further includes a start control 1114a and a stop control 1114b to control execution of the protocol presented in the protocol entry field 1112. The GUI 1100 may be provided on a touch screen interface, for example, where touch selection of the start control 1114a starts cell processing, and selection of the stop control 1114b stops cell processing.

Turning to the run status pane 1104, in some implementations, a chart 1116 illustrates stages of the processing of the protocol identified in the protocol pane 1102. For example, a portion of run completion 1118a is illustrated in blue, while a portion of current stage 1118b is illustrated in green, and any errors 1118c are flagged with markers extending from the point in time along the course of the portion of the run completion 1118a where the error occurred. A message region 1118d presents a percentage of run completed, a percentage of stage completed, and a total number of errors. In some embodiments, upon selection of the chart 1116, the user may be presented with greater details regarding the run status such as, in some examples, identification of the type of error, a name of the current processing stage (e.g., nucleic acid assembly, purification, cell growth, filtration, transformation, recovery, editing, etc.), and a listing of processing stages within the run. Further, in some embodiments, a run completion time message indicates a date and time at which the run is estimated to complete. The run, in some examples, may be indicative of a single cell editing process or a series of recursive cell editing processes scheduled for execution without user intervention. In some embodiments (not shown), the run status pane 1104 additionally illustrates an estimated time at which user intervention will be required (e.g., cartridge replacement, solid waste disposal, liquid waste disposal, etc.).

In some implementations, the run status pane 1104 includes a pause control 1124 for pausing cell processing. The user may select to pause the current run, for example, to correct for an identified error or to conduct manual intervention such as waste removal.

The temperature pane 1106, in some embodiments, illustrates a series of icons 1126 with corresponding messages 1128 indicating temperature settings for various apparatus of the automated multi-module cell processing instrument. The icons, from left to right, may represent a transformation module 1126a (e.g., flow-through electroporation cartridge associated with the reagent cartridge 110c of FIG. 1A or the flow-through electroporation devices 534 of FIG. 5B), a purification module 1126b, a first growth module 1126c, a second growth module 1126d, and a filtration module 1126e. The corresponding messages 1128a-e identify a present temperature, low temperature, and high temperature of the corresponding module (e.g., for this stage or this run). In selecting one of the icons 1126, in some embodiments, a graphic display of temperature of time may be reviewed.

Beneath the temperature pane, in some implementations, a series of panes identify present status of a number of modules. For example, the electroporation pane 1108 represents status of a transformation module, while the cell growth pane 1110 represents the status of a growth module. In some embodiments, the panes presented here identify status of a presently operational module (e.g., the module involved in cell processing in the current stage) as well as the status of any modules which have already been utilized during the current run (as illustrated, for example, in the run status pane 1104). Past status information, for example, may present to the user information regarding the parameters used in the prior stage(s) of cell processing.

Turning to the electroporation pane 1108, in some implementations, operational parameters 1130a of volts, milliamps, and joules are presented. Additionally, a status message 1132a may identify additional information regarding the functioning of the transformation module such as, in some examples, an error status, a time remaining for processing, or contents of the module (e.g., materials added to the module). In some implementations, an icon 1134a above the status message 1132a will be presented in an active mode (e.g., colorful, "lit up", in bold, etc.) when the corresponding module is actively processing. Selection of the icon 1134a, in some embodiments, causes presentation of a graphic display of detailed information regarding the operational parameters 1130a.

Turning to the cell growth pane 1110, in some implementations, operational parameters 1130b of OD and hours of growth are presented. Additionally, a status message 1132b may identify additional information regarding the functioning of the growth module such as, in some examples, an error status, a time remaining for processing, or contents of the module (e.g., materials added to the module). In some implementations, an icon 1134b above the status message 1132b will be presented in an active mode (e.g., colorful, "lit up", in bold, etc.) when the corresponding module is actively processing. Selection of the icon 1134b, in some embodiments, causes presentation of a graphic display of detailed information regarding the operational parameters 1130b.

Next, a hardware description of an example processing system and processing environment according to exemplary embodiments is described with reference to FIG. 13. In FIG. 13, the processing system 1310 includes a CPU 1308 which performs a portion of the processes described above. For example, the CPU 1308 may manage the processing stages of the method 900 of FIG. 9 and/or the workflows of FIGS. 10A-C. The process data and, scripts, instructions, and/or user settings may be stored in memory 1302. These process data and, scripts, instructions, and/or user settings may also be stored on a storage medium disk 1304 such as a portable storage medium (e.g., USB drive, optical disk drive, etc.) or may be stored remotely. For example, the process data and, scripts, instructions, and/or user settings may be stored in a location accessible to the processing system 1310 via a network 1328. Further, the claimed advancements are not limited by the form of the computer-readable media on which the instructions of the inventive process are stored. For example, the instructions may be stored in FLASH memory, RAM, ROM, or any other information processing device with which the processing system 1310 communicates, such as a server, computer, smart phone, or other hand-held computing device.

Further, components of the claimed advancements may be provided as a utility application, background daemon, or component of an operating system, or combination thereof, executing in conjunction with CPU 1308 and an operating system such as with other computing systems known to those skilled in the art.

CPU 1308 may be an ARM processor, system-on-a-chip (SOC), microprocessor, microcontroller, digital signal processor (DSP), or may be other processor types that would be recognized by one of ordinary skill in the art. Further, CPU 1308 may be implemented as multiple processors cooperatively working in parallel to perform the instructions of the inventive processes described above.

The processing system 1310 is part of a processing environment 1300. The processing system 1310 in FIG. 13 also includes a network controller 1306 for interfacing with the network 1328 to access additional elements within the processing environment 1300. As can be appreciated, the network 1328 can be a public network, such as the Internet, or a private network such as an LAN or WAN network, or any combination thereof and can also include PSTN or ISDN sub-networks. The network 1328 can be wireless such as a cellular network including EDGE, 3G and 4G wireless cellular systems. The wireless network can also be Wi-Fi, Bluetooth, or any other wireless form of communication that is known.

The processing system 1310 further includes a general purpose I/O interface 1312 interfacing with a user interface (e.g., touch screen) 1316, one or more sensors 1314, and one or more peripheral devices 1318. The peripheral I/O devices 1318 may include, in some examples, a video recording system, an audio recording system, microphone, external storage devices, and/or external speaker systems. The one or more sensors 1314 may include one or more of a gyroscope, an accelerometer, a gravity sensor, a linear accelerometer, a global positioning system, a bar code scanner, a QR code scanner, an RFID scanner, a temperature monitor, and a lighting system or lighting element.

The general purpose storage controller 1324 connects the storage medium disk 1304 with communication bus 1340, such as a parallel bus or a serial bus such as a Universal Serial Bus (USB), or similar, for interconnecting all of the components of the processing system. A description of the general features and functionality of the storage controller 1324, network controller 1306, and general purpose I/O interface 1312 is omitted herein for brevity as these features are known.

The processing system 1310, in some embodiments, includes one or more onboard and/or peripheral sensors 1314. The sensors 1314, for example, can be incorporated directly into the internal electronics and/or a housing of the automated multi-module processing instrument. A portion of the sensors 1314 can be in direct physical contact with the I/O interface 1312, e.g., via a wire; or in wireless contact e.g., via a Bluetooth, Wi-Fi or NFC connection. For example, a wireless communications controller 1326 may enable communications between one or more wireless sensors 1314 and the I/O interface 1312. Furthermore, one or more sensors 1314 may be in indirect contact e.g., via intermediary servers or storage devices that are based in the network 1328; or in (wired, wireless or indirect) contact with a signal accumulator somewhere within the automated multi-module cell processing instrument, which in turn is in (wired or wireless or indirect) contact with the I/O interface 1312.

A group of sensors 1314 communicating with the I/O interface 1312 may be used in combination to gather a given signal type from multiple places in order to generate a more complete map of signals. One or more sensors 1314 communicating with the I/O interface 1312 can be used as a comparator or verification element, for example to filter, cancel, or reject other signals.

In some embodiments, the processing environment 1300 includes a computing device 1338 communicating with the processing system 1310 via the wireless communications controller 1326. For example, the wireless communications controller 1326 may enable the exchange of email messages, text messages, and/or software application alerts designated to a smart phone or other personal computing device of a user.

The processing environment 1300, in some implementations, includes a robotic material handling system 1322. The processing system 1310 may include a robotics controller 1320 for issuing control signals to actuate elements of the robotic material handling system, such as manipulating a position of a gantry, lowering or raising a sipper or pipettor element, and/or actuating pumps and valves to cause liquid transfer between a sipper/pipettor and various vessels (e.g., chambers, vials, etc.) in the automated multi-module cell processing instrument. The robotics controller 1320, in some examples, may include a hardware driver, firmware element, and/or one or more algorithms or software packages for interfacing the processing system 1310 with the robotics material handling system 1322.

In some implementations, the processing environment 1310 includes one or more module interfaces 1332, such as, in some examples, one or more sensor interfaces, power control interfaces, valve and pump interfaces, and/or actuator interfaces for activating and controlling processing of each module of the automated multi-module processing system. For example, the module interfaces 1332 may include an actuator interface for the drive motor 864 of rotating cell growth device 850 (FIG. 8D) and a sensor interface for the detector board 872 that senses optical density of cell growth within rotating growth vial 800. A module controller 1330, in some embodiments, is configured to interface with the module interfaces 1332. The module controller 1330 may include one or many controllers (e.g., possibly one controller per module, although some modules may share a single controller). The module controller 1330, in some examples, may include a hardware driver, firmware element, and/or one or more algorithms or software packages for interfacing the processing system 1310 with the module interfaces 1332.

The processing environment 1310, in some implementations, includes a thermal management system 1336 for controlling climate conditions within the housing of the automated multi-module processing system. The thermal management system 1336 may additional control climate conditions within one or more modules of the automated multi-module cell processing instrument. The processing system 1310, in some embodiments, includes a temperature controller 1334 for interfacing with the thermal management system 1336. The temperature controller 1334, in some examples, may include a hardware driver, firmware element, and/or one or more algorithms or software packages for interfacing the processing system 1310 with the thermal management system 1336.

Production of Cell Libraries Using Automated Editing Methods, Modules, Instruments and Systems In one aspect, the present disclosure provides automated editing methods, modules, instruments, and automated multi-module cell editing instruments for creating a library of cells that vary the expression, levels and/or activity of RNAs and/or proteins of interest in various cell types using various editing strategies, as described herein in more detail. Accordingly, the disclosure is intended to cover edited cell libraries created by the automated editing methods, automated multi-module cell editing instruments of the disclosure. These cell libraries may have different targeted edits, including but not limited to gene knockouts, gene knock-ins, insertions, deletions, single nucleotide edits, short tandem repeat edits, frameshifts, triplet codon expansion, and the like in cells of various organisms. These edits can be directed to coding or non-coding regions of the genome, and are preferably rationally designed.

In other aspects, the present disclosure provides automated editing methods, automated multi-module cell editing instruments for creating a library of cells that vary DNA-linked processes. For example, the cell library may include individual cells having edits in DNA binding sites to interfere with DNA binding of regulatory elements that modulate expression of selected genes. In addition, cell libraries may include edits in genomic DNA that impact on cellular processes such as heterochromatin formation, switch-class recombination and VDJ recombination.

In specific aspects, the cell libraries are created using multiplexed editing of individual cells within a cell population, with multiple cells within a cell population are edited in a single round of editing, i.e., multiple changes within the cells of the cell library are in a single automated operation. The libraries that can be created in a single multiplexed automated operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

In other specific aspects, the cell libraries are created using recursive editing of individual cells within a cell population, with edits being added to the individual cells in two or more rounds of editing. The use of recursive editing results in the amalgamation of two or more edits targeting two or more sites in the genome in individual cells of the library. The libraries that can be created in an automated recursive operation can comprise as many as 500 edited cells, 1000 edited cells, 2000 edited cells, 5000 edited cells, 10,000 edited cells, 50,000 edited cells, 100,000 edited cells, 200,000 edited cells, 300,000 edited cells, 400,000 edited cells, 500,000 edited cells, 600,000 edited cells, 700,000 edited cells, 800,000 edited cells, 900,000 edited cells, 1,000,000 edited cells, 2,000,000 edited cells, 3,000,000 edited cells, 4,000,000 edited cells, 5,000,000 edited cells, 6,000,000 edited cells, 7,000,000 edited cells, 8,000,000 edited cells, 9,000,000 edited cells, 10,000,000 edited cells or more.

Examples of non-automated editing strategies that can be modified based on the present specification to utilize the automated systems can be found, e.g., U.S. Pat. Nos. 8,110,360, 8,332,160, 9,988,624, 20170316353, and 20120277120.

In specific aspects, recursive editing can be used to first create a cell phenotype, and then later rounds of editing used to reverse the phenotype and/or accelerate other cell properties.

In some aspects, the cell library comprises edits for the creation of unnatural amino acids in a cell.

In specific aspects, the disclosure provides edited cell libraries having edits in one or more regulatory elements created using the automated editing methods, automated multi-module cell editing instruments of the disclosure. The term "regulatory element" refers to nucleic acid molecules that can influence the transcription and/or translation of an operably linked coding sequence in a particular environment and/or context. This term is intended to include all elements that promote or regulate transcription, and RNA stability including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include, but are not limited to, promoters, operator sequences and a ribosome binding sites. Regulatory elements that are used in eukaryotic cells may include, but are not limited to, promoters, enhancers, insulators, splicing signals and polyadenylation signals.

Preferably, the edited cell library includes rationally designed edits that are designed based on predictions of protein structure, expression and/or activity in a particular cell type. For example, rational design may be based on a system-wide biophysical model of genome editing with a particular nuclease and gene regulation to predict how different editing parameters including nuclease expression and/or binding, growth conditions, and other experimental conditions collectively control the dynamics of nuclease editing. See, e.g., Farasat and Salis, PLoS Comput Biol., 29:12 (1):e1004724 (2016).

In one aspect, the present disclosure provides the creation of a library of edited cells with various rationally designed regulatory sequences created using the automated editing instrumentation, systems and methods of the invention. For example, the edited cell library can include prokaryotic cell populations created using set of constitutive and/or inducible promoters, enhancer sequences, operator sequences and/or ribosome binding sites. In another example, the edited cell library can include eukaryotic sequences created using a set of constitutive and/or inducible promoters, enhancer sequences, operator sequences, and/or different Kozak sequences for expression of proteins of interest.

In some aspects, the disclosure provides cell libraries including cells with rationally designed edits comprising one or more classes of edits in sequences of interest across the genome of an organism. In specific aspects, the disclosure provides cell libraries including cells with rationally designed edits comprising one or more classes of edits in sequences of interest across a subset of the genome. For example, the cell library may include cells with rationally designed edits comprising one or more classes of edits in sequences of interest across the exome, e.g., every or most open reading frames of the genome. For example, the cell library may include cells with rationally designed edits comprising one or more classes of edits in sequences of interest across the kinome. In yet another example, the cell library may include cells with rationally designed edits comprising one or more classes of edits in sequences of interest across the secretome. In yet other aspects, the cell library may include cells with rationally designed edits created to analyze various isoforms of proteins encoded within the exome, and the cell libraries can be designed to control expression of one or more specific isoforms, e.g., for transcriptome analysis.

Importantly, in certain aspects the cell libraries may comprise edits using randomized sequences, e.g., randomized promoter sequences, to reduce similarity between expression of one or more proteins in individual cells within the library. Additionally, the promoters in the cell library can be constitutive, inducible or both to enable strong and/or titratable expression.

In other aspects, the present disclosure provides automated editing methods, automated multi-module cell editing instruments for creating a library of cells comprising edits to identify optimum expression of a selected gene target. For example, production of biochemicals through metabolic engineering often requires the expression of pathway enzymes, and the best production yields are not always achieved by the highest amount of the target pathway enzymes in the cell, but rather by fine-tuning of the expression levels of the individual enzymes and related regulatory proteins and/or pathways. Similarly, expression levels of heterologous proteins sometimes can be experimentally adjusted for optimal yields.

The most obvious way that transcription impacts on gene expression levels is through the rate of Pol II initiation, which can be modulated by combinations of promoter or enhancer strength and trans-activating factors (Kadonaga, et al., Cell, 116(2):247-57 (2004). In eukaryotes, elongation rate may also determine gene expression patterns by influencing alternative splicing (Cramer et al., PNAS USA, 94(21):11456-60 (1997). Failed termination on a gene can impair the expression of downstream genes by reducing the accessibility of the promoter to Pol II (Greger, et al., 2000 PNAS USA, 97(15):8415-20 (2000). This process, known as transcriptional interference, is particularly relevant in lower eukaryotes, as they often have closely spaced genes.

In some embodiments, the present disclosure provides methods for optimizing cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination).

Site Directed Mutagenesis

Cell libraries can be created using the automated editing methods, modules, instruments and systems employing site-directed mutagenesis, i.e., when the amino acid sequence of a protein or other genomic feature may be altered by deliberately and precisely by mutating the protein or genomic feature. These cell lines can be useful for various purposes, e.g., for determining protein function within cells, the identification of enzymatic active sites within cells, and the design of novel proteins. For example, site-directed mutagenesis can be used in a multiplexed fashion to exchange a single amino acid in the sequence of a protein for another amino acid with different chemical properties. This allows one to determine the effect of a rationally designed or randomly generated mutation in individual cells within a cell population. See, e.g., Berg, et al. Biochemistry, Sixth Ed. (New York: W.H. Freeman and Company) (2007).

In another example, edits can be made to individual cells within a cell library to substitute amino acids in binding sites, such as substitution of one or more amino acids in a protein binding site for interaction within a protein complex or substitution of one or more amino acids in enzymatic pockets that can accommodate a cofactor or ligand. This class of edits allows the creation of specific manipulations to a protein to measure certain properties of one or more proteins, including interaction with other cofactors, ligands, etc. within a protein complex.

In yet another examples, various edit types can be made to individual cells within a cell library using site specific mutagenesis for studying expression quantitative trait loci (eQTLs). An eQTL is a locus that explains a fraction of the genetic variance of a gene expression phenotype. The libraries of the invention would be useful to evaluate and link eQTLs to actual diseased states.

In specific aspects, the edits introduced into the cell libraries of the disclosure may be created using rational design based on known or predicted structures of proteins. See, e.g., Chronopoulou EG and Labrou, Curr Protoc Protein Sci.; Chapter 26:Unit 26.6 (2011). Such site-directed mutagenesis can provide individual cells within a library with one or more site-directed edits, and preferably two or more site-directed edits (e.g., combinatorial edits) within a cell population.

In other aspects, cell libraries of the disclosure are created using site-directed codon mutation "scanning" of all or substantially all of the codons in the coding region of a gene. In this fashion, individual edits of specific codons can be examined for loss-of-function or gain-of-function based on specific polymorphisms in one or more codons of the gene. These libraries can be a powerful tool for determining which genetic changes are silent or causal of a specific phenotype in a cell or cell population. The edits of the codons may be randomly generated or may be rationally designed based on known polymorphisms and/or mutations that have been identified in the gene to be analyzed. Moreover, using these techniques on two or more genes in a single in a pathway in a cell may determine potential protein:protein interactions or redundancies in cell functions or pathways.

For example, alanine scanning can be used to determine the contribution of a specific residue to the stability or function of given protein. See, e.g., Lefévre, et al., Nucleic Acids Research, Volume 25(2):447-448 (1997). Alanine is often used in this codon scanning technique because of its non-bulky, chemically inert, methyl functional group that can mimic the secondary structure preferences that many of the other amino acids possess. Codon scanning can also be used to determine whether the side chain of a specific residue plays a significant role in cell function and/or activity. Sometimes other amino acids such as valine or leucine can be used in the creation of codon scanning cell libraries if conservation of the size of mutated residues is needed.

In other specific aspects, cell libraries can be created using the automated editing methods, automated multi-module cell editing instruments of the invention to determine the active site of a protein such as an enzyme or hormone, and to elucidate the mechanism of action of one or more of these proteins in a cell library. Site-directed mutagenesis associated with molecular modeling studies can be used to discover the active site structure of an enzyme and consequently its mechanism of action. Analysis of these cell libraries can provide an understanding of the role exerted by specific amino acid residues at the active sites of proteins, in the contacts between subunits of protein complexes, on intracellular trafficking and protein stability/half-life in various genetic backgrounds.

Saturation Mutagenesis

In some aspects, the cell libraries created using the automated editing methods, automated multi-module cell editing instruments of the disclosure may saturation mutagenesis libraries, in which a single codon or set of codons is randomized to produce all possible amino acids at the position of a particular gene or genes of interest. These cell libraries can be particularly useful to generate variants, e.g., for directed evolution. See, e.g., Chica, et al., Current Opinion in Biotechnology 16 (4): 378-384 (2005); and Shivange, Current Opinion in Chemical Biology, 13 (1): 19-25.

In some aspects, edits comprising different degenerate codons can be used to encode sets of amino acids in the individual cells in the libraries. Because some amino acids are encoded by more codons than others, the exact ratio of amino acids cannot be equal. In certain aspects, more restricted degenerate codons are used. 'NNK' and 'NNS' have the benefit of encoding all 20 amino acids, but still encode a stop codon 3% of the time. Alternative codons such as 'NDT', 'DBK' avoid stop codons entirely, and encode a minimal set of amino acids that still encompass all the main biophysical types (anionic, cationic, aliphatic hydrophobic, aromatic hydrophobic, hydrophilic, small).

In specific aspects, the non-redundant saturation mutagenesis, in which the most commonly used codon for a particular organism is used in the saturation mutagenesis editing process.

Promoter Swaps and Ladders

One mechanism for analyzing and/or optimizing expression of one or more genes of interest is through the creation of a "promoter swap" cell library, in which the cells comprise genetic edits that have specific promoters linked to one or more genes of interest. Accordingly, the cell libraries created using the methods, automated multi-module cell editing instruments of the disclosure may be promoter swap cell libraries, which can be used, e.g., to increase or decrease expression of a gene of interest to optimize a metabolic or genetic pathway. In some aspects, the promoter swap cell library can be used to identify an increase or reduction in the expression of a gene that affects cell vitality or viability, e.g., a gene encoding a protein that impacts on the growth rate or overall health of the cells. In some aspects, the promoter swap cell library can be used to create cells having dependencies and logic between the promoters to create synthetic gene networks. In some aspects, the promoter swaps can be used to control cell to cell communication between cells of both homogeneous and heterogeneous (complex tissues) populations in nature.

The cell libraries can utilize any given number of promoters that have been grouped together based upon exhibition of a range of expression strengths and any given number of target genes. The ladder of promoter sequences vary expression of at least one locus under at least one condition. This ladder is then systematically applied to a group of genes in the organism using the automated editing methods, automated multi-module cell editing instruments of the disclosure.

In specific aspects, the cell library formed using the automated editing processes, modules and systems of the disclosure include individual cells that are representative of a given promoter operably linked to one or more target genes of interest in an otherwise identical genetic background. Examples of non-automated editing strategies that can be modified to utilize the automated systems can be found, e.g., in U.S. Pat. No. 9,988,624.

In specific aspects, the promoter swap cell library is produced by editing a set of target genes to be operably linked to a pre-selected set of promoters that act as a "promoter ladder" for expression of the genes of interest. For example, the cells are edited so that one or more individual genes of interest are edited to be operably linked with the different promoters in the promoter ladder. When an endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context.

The promoters are generally selected to result in variable expression across different loci, and may include inducible promoters, constitutive promoters, or both.

The set of target genes edited using the promoter ladder can include all or most open reading frames (ORFs) in a genome, or a selected subset of the genome, e.g., the ORFs of the kinome or a secretome. In some aspects, the target genes can include coding regions for various isoforms of the genes, and the cell libraries can be designed to expression of one or more specific isoforms, e.g., for transcriptome analysis using various promoters.

The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

Editing of other functional genetic elements, including insulator elements and other genomic organization elements, can also be used to systematically vary the expression level of a set of target genes, and can be introduced using the methods, automated multi-module cell editing instruments of the disclosure. In one aspect, a population of cells is edited using a ladder of enhancer sequences, either alone or in combination with selected promoters or a promoter ladder, to create a cell library having various edits in these enhancer elements. In another aspect, a population of cells is edited using a ladder of ribosome binding sequences, either alone or in combination with selected promoters or a promoter ladder, to create a cell library having various edits in these ribosome binding sequences.

In another aspect, a population of cells is edited to allow the attachment of various mRNA and/or protein stabilizing or destabilizing sequences to the 5' or 3' end, or at any other location, of a transcript or protein.

In certain aspects, a population of cells of a previously established cell line may be edited using the automated editing methods, modules, instruments, and systems of the disclosure to create a cell library to improve the function, health and/or viability of the cells. For example, many industrial strains currently used for large scale manufacturing have been developed using random mutagenesis processes iteratively over a period of many years, sometimes decades. Unwanted neutral and detrimental mutations were introduced into strains along with beneficial changes, and over time this resulted in strains with deficiencies in overall robustness and key traits such as growth rates. In another example, mammalian cell lines continue to mutate through the passage of the cells over periods of time, and likewise these cell lines can become unstable and acquire traits that are undesirable. The automated editing methods, automated multi-module cell editing instruments of the disclosure can use editing strategies such as SNP and/or STR swapping, indel creation, or other techniques to remove or change the undesirable genome sequences and/or introducing new genome sequences to address the deficiencies while retaining the desirable properties of the cells.

When recursive editing is used, the editing in the individual cells in the edited cell library can incorporate the inclusion of "landing pads" in an ectopic site in the genome (e.g., a CarT locus) to optimize expression, stability and/or control.

In some embodiments, each library produced having individual cells comprising one or more edits (either introducing or removing) is cultured and analyzed under one or more criteria (e.g., production of a chemical or product of interest). The cells possessing the specific criteria are then associated, or correlated, with one or more particular edits in the cell. In this manner, the effect of a given edit on any number of genetic or phenotypic traits of interest can be determined. The identification of multiple edits associated with particular criteria or enhanced functionality/robustness may lead to cells with highly desirable characteristics.

Knock-Out or Knock-In Libraries

In certain aspects, the present disclosure provides automated editing methods, modules, instruments and systems for creating a library of cells having "knock-out" (KO) or "knock-in" (KI) edits of various genes of interest. Thus, the disclosure is intended to cover edited cell libraries created by the automated editing methods, automated multi-module cell editing instruments of the disclosure that have one or more mutations that remove or reduce the expression of selected genes of interest to interrogate the effect of these edits on gene function in individual cells within the cell library.

The cell libraries can be created using targeted gene KO (e.g., via insertion/deletion) or KOs (e.g., via homologous directed repair). For example, double strand breaks are often repaired via the non-homologous end joining DNA repair pathway. The repair is known to be error prone, and thus insertions and deletions may be introduced that can disrupt gene function. Preferably the edits are rationally designed to specifically affect the genes of interest, and individual cells can be created having a KI or KI of one or more locus of interest. Cells having a KO or KI of two or more loci of interest can be created using automated recursive editing of the disclosure.

In specific aspects, the KO or KI cell libraries are created using simultaneous multiplexed editing of cells within a cell population, and multiple cells within a cell population are edited in a single round of editing, i.e., multiple changes within the cells of the cell library are in a single automated operation. In other specific aspects, the cell libraries are created using recursive editing of individual cells within a cell population, and results in the amalgamation of multiple edits of two or more sites in the genome into single cells.

SNP or Short Tandem Repeat Swaps

In one aspect, cell libraries are created using the automated editing methods, automated multi-module cell editing instruments of the disclosure by systematic introducing or substituting single nucleotide polymorphisms ("SNPs") into the genomes of the individual cells to create a "SNP swap" cell library. In some embodiments, the SNP swapping methods of the present disclosure include both the addition of beneficial SNPs, and removing detrimental and/or neutral SNPs. The SNP swaps may target coding sequences, non-coding sequences, or both.

In another aspect, a cell library is created using the automated editing methods, modules, instruments, instruments, and systems of the disclosure by systematic introducing or substituting short tandem repeats ("STR") into the genomes of the individual cells to create an "STR swap" cell library. In some embodiments, the STR swapping methods of the present disclosure include both the addition of beneficial STRs, and removing detrimental and/or neutral STRs. The STR swaps may target coding sequences, non-coding sequences, or both.

In some embodiments, the SNP and/or STR swapping used to create the cell library is multiplexed, and multiple cells within a cell population are edited in a single round of editing, i.e., multiple changes within the cells of the cell library are in a single automated operation. In other embodiments, the SNP and/or STR swapping used to create the cell library is recursive, and results in the amalgamation of multiple beneficial sequences and/or the removal of detrimental sequences into single cells. Multiple changes can be either a specific set of defined changes or a partly randomized, combinatorial library of mutations. Removal of detrimental mutations and consolidation of beneficial mutations can provide immediate improvements in various cellular processes. Removal of genetic burden or consolidation of beneficial changes into a strain with no genetic burden also provides a new, robust starting point for additional random mutagenesis that may enable further improvements.

SNP swapping overcomes fundamental limitations of random mutagenesis approaches as it is not a random approach, but rather the systematic introduction or removal of individual mutations across cells.

Splice Site Editing

RNA splicing is the process during which introns are excised and exons are spliced together to create the mRNA that is translated into a protein. The precise recognition of splicing signals by cellular machinery is critical to this process. Accordingly, in some aspects, a population of cells is edited using a systematic editing to known and/or predicted splice donor and/or acceptor sites in various loci to create a library of splice site variants of various genes. Such editing can help to elucidate the biological relevance of various isoforms of genes in a cellular context. Sequences for rational design of splicing sites of various coding regions, including actual or predicted mutations associated with various mammalian disorders, can be predicted using analysis techniques such as those found in Nalla and Rogan, Hum Mutat, 25:334-342 (2005); Divina, et al., Eur J Hum Genet, 17:759-765 (2009); Desmet, et el., Nucleic Acids Res, 37:e67 (2009); Faber, et al., BMC Bioinformatics, 12 (suppl 4):S2 (2011).

Start/Stop Codon Exchanges and Incorporation of Nucleic Acid Analogs

In some aspects, the present disclosure provides for the creation of cell libraries using the automated editing methods, modules, instruments and systems of the disclosure, where the libraries are created by swapping start and stop codon variants throughout the genome of an organism or for a selected subset of coding regions in the genome, e.g., the kinome or secretome. In the cell library, individual cells will have one or more start or stop codons replacing the native start or stop codon for one or more gene of interest.

For example, typical start codons used by eukaryotes are ATG (AUG) and prokaryotes use ATG (AUG) the most, followed by GTG (GUG) and TTG (UUG). The cell library may include individual cells having substitutions for the native start codons for one or more genes of interest.

In some aspects, the present disclosure provides for automated creation of a cell library by replacing ATG start codons with TTG in front of selected genes of interest. In other aspects, the present disclosure provides for automated creation of a cell library by replacing ATG start codons with GTG. In other aspects, the present disclosure provides for automated creation of a cell library by replacing GTG start codons with ATG. In other aspects, the present disclosure provides for automated creation of a cell library by replacing GTG start codons with TTG. In other aspects, the present disclosure provides for automated creation of a cell library by replacing TTG start codons with ATG. In other aspects, the present disclosure provides for automated creation of a cell library by replacing TTG start codons with GTG.

In other examples, typical stop codons for *S. cerevisiae* and mammals are TAA (UAA) and TGA (UGA), respectively. The typical stop codon for monocotyledonous plants is TGA (UGA), whereas insects and *E. coli* commonly use TAA (UAA) as the stop codon (Dalphin. et al., Nucl. Acids Res., 24: 216-218 (1996)). The cell library may include individual cells having substitutions for the native stop codons for one or more genes of interest.

In some aspects, the present disclosure provides for automated creation of a cell library by replacing TAA stop codons with TAG. In other aspects, the present disclosure provides for automated creation of a cell library by replacing TAA stop codons with TGA. In other aspects, the present disclosure provides for automated creation of a cell library by replacing TGA stop codons with TAA. In other aspects, the present disclosure provides for automated creation of a cell library by replacing TGA stop codons with TAG. In other aspects, the present disclosure provides for automated creation of a cell library by replacing TAG stop codons with TAA. In other aspects, the present invention teaches automated creation of a cell library by replacing TAG stop codons with TGA.

Terminator Swaps and Ladders

One mechanism for identifying optimum termination of a pre-spliced mRNA of one or more genes of interest is through the creation of a "terminator swap" cell library, in which the cells comprise genetic edits that have specific terminator sequences linked to one or more genes of interest. Accordingly, the cell libraries created using the methods, modules, instruments and systems of the disclosure may be terminator swap cell libraries, which can be used, e.g., to affect mRNA stability by releasing transcripts from sites of synthesis. In other embodiments, the terminator swap cell library can be used to identify an increase or reduction in the efficiency of transcriptional termination and thus accumulation of unspliced pre-mRNA (e.g., West and Proudfoot, Mol Cell.; 33(3-9); 354-364 (2009) and/or 3' end processing (e.g., West, et al., Mol Cell. 29(5):600-10 (2008)). In the case where a gene is linked to multiple termination sites, the edits may edit a combination of edits to multiple terminators that are associated with a gene. Additional amino acids may also be added to the ends of proteins to determine the effect on the protein length on terminators.

The cell libraries can utilize any given number of edits of terminators that have been selected for the terminator ladder based upon exhibition of a range of activity and any given number of target genes. The ladder of terminator sequences vary expression of at least one locus under at least one condition. This ladder is then systematically applied to a group of genes in the organism using the automated editing methods, modules, instruments and systems of the disclosure.

In some aspects, the present disclosure provides for the creation of cell libraries using the automated editing methods, modules, instruments and systems of disclosure, where the libraries are created to edit terminator signals in one or more regions in the genome in the individual cells of the library. Transcriptional termination in eukaryotes operates through terminator signals that are recognized by protein factors associated with the RNA polymerase II. For example, the cell library may contain individual eukaryotic cells with edits in genes encoding polyadenylation specificity factor (CPSF) and cleavage stimulation factor (CstF) and or gene encoding proteins recruited by CPSF and CstF factors to termination sites. In prokaryotes, two principal mechanisms, termed Rho-independent and Rho-dependent termination, mediate transcriptional termination. For example, the cell library may contain individual prokaryotic cells with edits in genes encoding proteins that affect the binding, efficiency and/or activity of these termination pathways.

In certain aspects, the present disclosure provides methods of selecting termination sequences ("terminators") with optimal properties. For example, in some embodiments, the present disclosure teaches provides methods for introducing and/or editing one or more terminators and/or generating variants of one or more terminators within a host cell, which exhibit a range of activity. A particular combination of terminators can be grouped together as a terminator ladder, and cell libraries of the disclosure include individual cells that are representative of terminators operably linked to one or more target genes of interest in an otherwise identical genetic background. Examples of non-automated editing strategies that can be modified to utilize the automated instruments can be found, e.g., in U.S. Pat. No. 9,988,624 to Serber et al., entitled "Microbial strain improvement by a HTP genomic engineering platform."

In specific aspects, the terminator swap cell library is produced by editing a set of target genes to be operably linked to a pre-selected set of terminators that act as a "terminator ladder" for expression of the genes of interest. For example, the cells are edited so that the endogenous promoter is operably linked to the individual genes of interest are edited with the different promoters in the promoter ladder. When the endogenous promoter does not exist, its sequence is unknown, or it has been previously changed in some manner, the individual promoters of the promoter ladder can be inserted in front of the genes of interest. These produced cell libraries have individual cells with an individual promoter of the ladder operably linked to one or more target genes in an otherwise identical genetic context. The terminator ladder in question is then associated with a given gene of interest.

The terminator ladder can be used to more generally affect termination of all or most ORFs in a genome, or a selected subset of the genome, e.g., the ORFs of a kinome or a secretome. The set of target genes can also be genes known or suspected to be involved in a particular cellular pathway, e.g. a regulatory pathway or signaling pathway. The set of target genes can be ORFs related to function, by relation to previously demonstrated beneficial edits (previous promoter swaps or previous SNP swaps), by algorithmic selection based on epistatic interactions between previously generated edits, other selection criteria based on hypotheses regarding beneficial ORF to target, or through random selection. In specific embodiments, the target genes can comprise non-protein coding genes, including non-coding RNAs.

While certain embodiments have been described, these embodiments have been presented by way of example only, and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

We claim:

1. An automated stand-alone multi-module cell editing instrument comprising:
 a receptacle configured to receive cells;
 one or more receptacles configured to receive expression vectors, wherein the expression vectors introduce a desired DNA change to the target region and remove a proto-spacer motif (PAM) region from the target region;
 a growth module for growing the cells for transformation;
 a cell concentration module to concentrate the cells;
 a transformation module configured to introduce nucleic acids into the cells by bead transfection;
 a selection module;
 a nuclease-directed editing module configured to allow the introduced nucleic acids to edit nucleic acids in the cells using an RNA-guided nuclease;
 a processor configured to operate the automated multi-module cell editing instrument based on user input and/or selection of a pre-programmed script; and
 an automated liquid handling system to move liquids from the receptacle to the growth module, from the growth module to the cell concentration module, from the cell concentration module to the transformation module, from the transformation module to the selection module, and from the selection module to the nuclease-directed editing module, without user intervention.

2. The automated stand-alone multi-module cell editing instrument of claim 1, wherein the nuclease-directed editing module is also a selection module.

3. The automated stand-alone multi-module cell editing instrument of claim 1, wherein the selection module is separate from the nuclease-directed editing module.

4. The automated stand-alone multi-module cell editing instrument of claim 1, wherein the selection module comprises an antibiotic.

5. The automated stand-alone multi-module cell editing instrument of claim 1, wherein the nuclease-directed editing module is also a recovery module.

6. The automated stand-alone multi-module cell editing instrument of claim 1, wherein the nuclease-directed editing module further comprises a recovery module.

7. The automated stand-alone multi-module cell editing instrument of claim 1, wherein the RNA-guided nuclease is MAD7.

8. The automated stand-alone multi-module cell editing instrument of claim 1, wherein the RNA-guided nuclease editing system is an inducible system.

9. The automated stand-alone multi-module cell editing instrument of claim 1, wherein the growth module is also the cell concentration module.

10. The automated stand-alone multi-module cell editing instrument of claim 1, wherein the growth module is separate from the cell concentration module.

11. The automated stand-alone multi-module cell editing instrument of claim 1, wherein the cell concentration module is also the cell transformation module.

12. The automated stand-alone multi-module cell editing instrument of claim 1, wherein the cell concentration module is separate from the cell transformation module.

13. The automated stand-alone multi-module cell editing instrument of claim 1, wherein the growth module, transformation module and nuclease-directed editing module are combined.

14. The automated stand-alone multi-module cell editing instrument of claim 13, wherein the cell concentration module is combined with the growth module, transformation module and the nuclease-directed editing module.

15. An automated stand-alone multi-module cell editing instrument for RNA-guided editing of mammalian cells comprising:
 a receptacle configured to receive mammalian cells;
 one or more receptacles configured to receive expression vectors, wherein the expression vectors introduce a desired DNA change to the target region and remove a proto-spacer motif (PAM) region from the target region;
 a growth module for growing the mammalian cells for transformation;
 a cell concentration module to concentrate the mammalian cells;
 a transformation module configured to introduce nucleic acids into the mammalian cells by bead transfection;
 a nuclease-directed editing module configured to allow the introduced nucleic acids to edit nucleic acids in the cells using an RNA-guided nuclease;
 a processor configured to operate the automated multi-module cell editing instrument based on user input and/or selection of a pre-programmed script; and
 an automated liquid handling system to move liquids from the receptacle to the growth module, from the growth module to the cell concentration module, from the cell concentration module to the transformation module, and from the transformation module to the nuclease-directed editing module, without user intervention.

16. The automated stand-alone multi-module cell editing instrument of claim 15, wherein the nuclease-directed editing module is also a selection module.

17. The automated stand-alone multi-module cell editing instrument of claim 15, wherein the receptacle configured to receive mammalian cells is also the growth module.

18. The automated stand-alone multi-module cell editing instrument of claim 15, wherein the nuclease-directed editing module is also a recovery module.

19. The automated stand-alone multi-module cell editing instrument of claim 15, wherein the nuclease-directed editing module further comprises a recovery module.

20. The automated stand-alone multi-module cell editing instrument of claim 15, wherein the RNA-guided nuclease is MAD7.

21. The automated stand-alone multi-module cell editing instrument of claim 15, wherein the RNA-guided nuclease editing system is an inducible system.

22. The automated stand-alone multi-module cell editing instrument of claim 21, wherein the RNA-guided nuclease editing system is a chemically-inducible system.

23. The automated stand-alone multi-module cell editing instrument of claim 15, wherein the growth module is also the cell concentration module.

24. The automated stand-alone multi-module cell editing instrument of claim 15, wherein the growth module is separate from the cell concentration module.

25. The automated stand-alone multi-module cell editing instrument of claim 15, wherein the cell concentration module is also the cell transformation module.

26. The automated stand-alone multi-module cell editing instrument of claim 15, wherein the cell concentration module is separate from the cell transformation module.

27. The automated stand-alone multi-module cell editing instrument of claim 15, wherein the growth module, transformation module and nuclease-directed editing module are combined.

28. The automated stand-alone multi-module cell editing instrument of claim 15, wherein the receptacle configured to receive mammalian cells is combined with the growth module, transformation module and the nuclease-directed editing module.

29. The automated stand-alone multi-module cell editing instrument of claim 15, wherein the automated liquid handling system comprises a sipper or pipettor.

30. The automated stand-alone multi-module cell editing instrument of claim 15, wherein the housing is configured to house all of the modules.

\* \* \* \* \*